Figure 2:
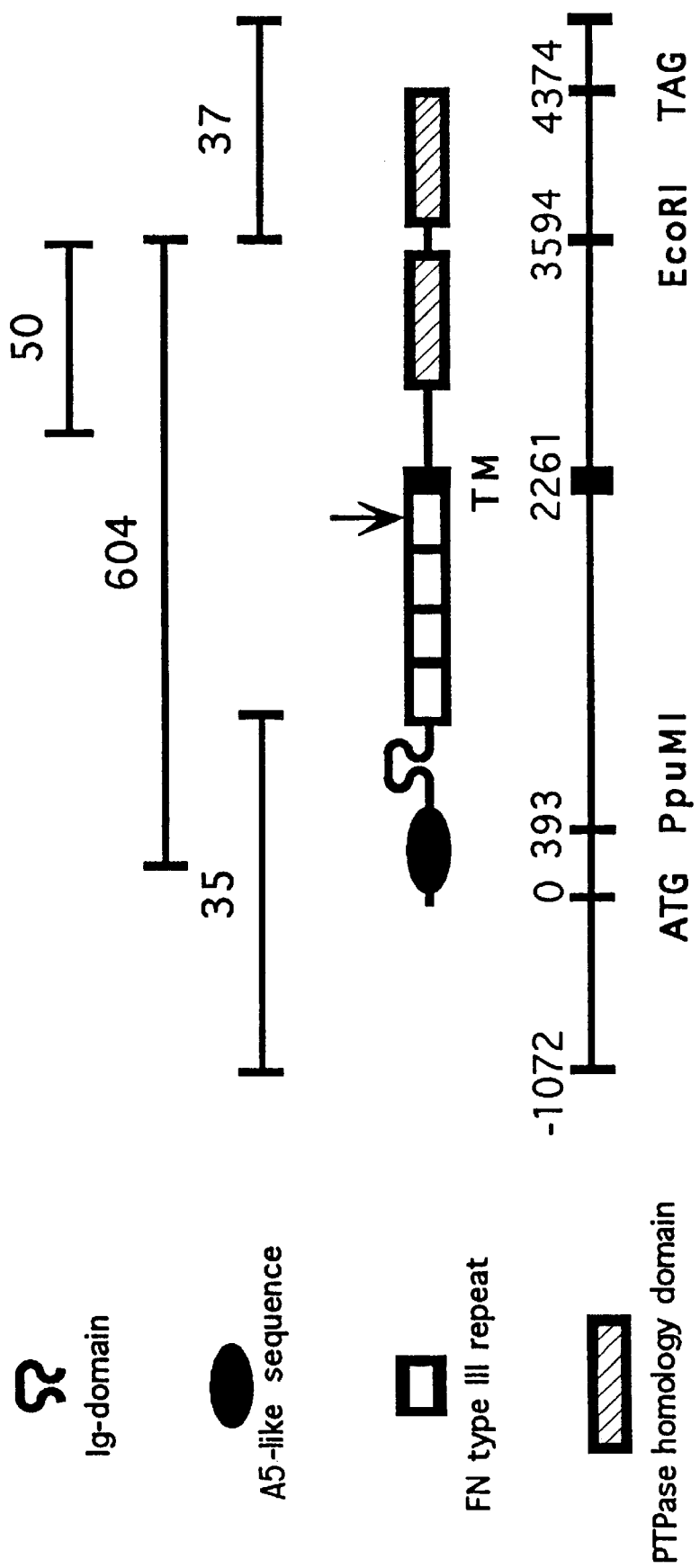

US005863755A

United States Patent [19]
Schlessinger et al.

[11] Patent Number: 5,863,755
[45] Date of Patent: Jan. 26, 1999

[54] NUCLEIC ACID ENCODING NOVEL RECEPTOR-TYPE PHOSPHOTYROSINE PHOSPHATASE-κ

[75] Inventors: Joseph Schlessinger; Jan M. Sap, both of New York, N.Y.; Axel Ullrich, München, Germany; Wolfgang Vogel, Germering, Germany; Miriam Fuchs, Starnberg, Germany

[73] Assignees: Max Planck Gessellschaft, Gottingen, Germany; New York University Medical Center, New York, N.Y.

[21] Appl. No.: 87,244

[22] Filed: Jul. 1, 1993

Related U.S. Application Data

[63] Continuation-in-part of Ser. No. 49,384, Apr. 21, 1993, abandoned.
[51] Int. Cl.$^6$ .......................... C12N 15/52; C07K 14/705
[52] U.S. Cl. ................ 435/69.1; 435/252.3; 435/254.11; 435/320.1; 435/325; 435/196; 536/23.5; 536/24.31
[58] Field of Search ................................. 536/23.1, 23.5, 536/24.31; 435/69.1, 240.1, 320.1, 325, 252.3, 254.11, 196; 530/395

[56] References Cited

FOREIGN PATENT DOCUMENTS

WO92/01050  1/1992  WIPO .

OTHER PUBLICATIONS

Jiang et al., Molecular and Cellular Biology, vol. 13, p. 2942, 1993.
LaForgia et al., Receptor protein–tyrosine phosphatase gamma is a candidate tumor suppressor gene at human chromosome region 3p21. Proc. Natl. Acad. Sci. USA 88:5036–5040, (1991).
Daum et al., Characterization of a human recombinant receptor–linked protein tyrosine phosphatase, J. Biol. Chem., 266: 12211–12215 (1991).
Gebbink et al., Cloning, expression and chromosomal localization of a new putative receptor–like protein tyrosine phosphatase, FEBS Lett. 290: 123–130 (1991).
Kaplan et al., Cloning of three human tyrosine phosphatases reveals a multigene family of receptor–linked protein–tyrosine–phosphatases expressed in brain, Proc. Natl. Acad. Sci. USA 87: 7000–7004 (1990).
Sap et al., Cloning and expression of a widely expressed receptor tyrosine phosphatase, Proc. Natl. Acad. Sci. USA 87: 6112–6116 (1990).
George and Parker, Preliminary characterization of phosphotyrosine phosphatase activities in human peripheral blood lymphocytes: Identification of CD45 as a phosphotyrosine phosphatase, J. Cell Biochem. 42: 71–81 (1990).
Nishi et al., Novel putative protein tyrosine phosphatases identified by the polymerase chain reaction. FEBS Lett. 271:178–180. (1990).

Jirik et al., Cloning of a novel receptor–linked protein tyrosine phosphatase from a human hepatoblastoma cell line, FASEB J. 4A: 2082 (Abstr. 2253) (1990).
Jirik et al., Cloning and chromosomal assignment of a widely expressed human receptor–like protein–tyrosine phosphatase, FEBS Lett. 273: 239–242 (1990).
Krueger et al., Structural diversity and evolution of human receptor–like protein tyrosine phosphatases, EMBO J. 9: 3241–3252 (1990).
Matthews et al., Identification of an additional member of the protein–tyrosine–phosphatase family: Evidence for alternative splicing in the tyrosine phosphatase domain, Proc. Natl. Acad. Sci. USA 87: 4444–4448 (1990).
Ohagi et al., Sequence of a cDNA encoding human LRP (leukocyte common antigen–related peptide), Nucl. Acids Res. 18: 7159 (1990).
Streuli et al., Distinct functional roles of the two intracellular phosphatase like domains of the receptor–linked protein tyrosine phosphatases LCA and LAR, EMBO J. 9: 2399–2407 (1990).
Streuli et al., A new member of the immunoglobulin superfamily that has a cytoplasmic region homologous to the leukocyte common antigen, J. Exp. Med. 168: 1523–1530 (1988).
Tonks et al., Demonstration that the leukocyte common antigen CD45 is a protein tyrosine phosphatase, Biochemistry 27: 8695–8701 (1988).
Charbonneau et al., The leukocyte common antigen (CD45): A putative receptor–linked protein tyrosine phosphatase, Proc. Natl. Acad. Sci. USA 85: 7182–7186 (1988).
Ralph et al., Structural variants of human T200 glycoprotein (leukocyte–common antigen), EMBO J. 6: 1251–1257 (1987).
Tian et al., Three receptor–linked protein–tyrosine phosphates are selectively expressed on central nervous system axons in the Drosophila embryo. Cell 67:675–685 (1991).
Yang et al., Two Drosophila receptor–like tyrosine phosphatase genes are expressed in a subset of developing axons and pioneeer neurons in the embryonic CNS. Cell 67:661–673 (1991).
Hariharan et al., Cloning and characterization of a receptor––class phosphotyrosine phosphatase gene expressed on central nervous system axons in *Drosophila melanogaster*, Proc. Natl. Acad. Sci. USA 88: 11266–11270 ( 1991).
Streuli et al., A family of receptor–linked protein tyrosine phosphatases in humans and Drosophila, Proc. Natl. Acad. Sci. USA 86: 8698–8702 (1989).

(List continued on next page.)

*Primary Examiner*—Sally Teng
*Attorney, Agent, or Firm*—Pennie & Edmonds LLP

[57] ABSTRACT

A novel receptor-type protein tyrosine phosphatase-κ (RPTPκ) protein or glycoprotein and the DNA coding therefor is expressed in a wide variety of mammalian tissues. The RPTPκ protein or glycoprotein may be produced by recombinant means. Antibodies to the protein, methods for measuring the quantity of the protein, methods for screening compounds, such as drugs, which can bind to the protein and inhibit or stimulate their enzymatic activity, are provided. Further, methods for inhibiting homophilic binding of Type II RPTP, especially RPTPκ molecules are provided.

19 Claims, 37 Drawing Sheets

OTHER PUBLICATIONS

Yi et al., Protein tyrosine phosphatase containing SH2 domains: charaterization, preferential expression in hematopoietic cells, and localization to human chromosome 12p12–p13, Mol. and Cell. Biol. 12: 836–846 (1992).

Gu et al., Identification, cloning, and expression of a cytosolic megakaryocyte protein–tyrosine–phosphatase with sequence homology to cytoskeletal protein 4.1, Proc. Natl. Acad. Sci. USA 88: 5867–5871 (1991).

Chernoff et al., Cloning of a cDNA for a major human protein–tyrosine–phophatase, Proc. Natl. Acad. Sci. USA 87: 2735–2739 (1990).

Guan et al., Cloning and expression of a protein–tyrosine–phosphatase, Proc. Natl. Acad. Sci. USA 87: 1501–1505 (1990).

Charbonneau et al., Human placenta protein–tyrosine–phosphatase: Amino acid sequence and relationship to a family of receptor–like proteins. Proc. Natl. Acad. Sci. USA 86:5252–5256 (1989).

Cool et al., cDNA isolated from a human T–cell library encodes a member of the protein–tyrosine–phosphatase family, Proc. Natl. Acad. Sci. USA 86: 5257–5261 (1989).

Pallen et al., Purification of a phosphotyrosine phosphatase that dephosphorylates the epidermal growth–factor receptor autophosphorylation sites, Ann. N.Y. Acad. Sci. 551: 299–308 (1988).

Zheng et al., Cell transformation and activation of $pp60^{c-src}$ by overexpression of a protein tyrosine phosphatase. Nature 359:336–339 (1992).

Haughn et al., Association of tyrosine kinase $p56^{lck}$ with CD4 inhibits the induction of growth through the $\alpha\beta$ T–cell receptor. Nature 358:328–331 (1992).

Mustelin et al., Rapid activation of the T–cell tyrosine protein kinase pp56lck by the CD45 phosphotyrosine phosphatase, Proc. Natl. Acad. Sci. USA 86: 6302–6306 (1989).

Ostergaard et al., Expression of CD45 alters phosphrylation of the Ick–encoded tyrosine protein kinase in murine lymphoma T–cell lines, Proc. Natl. Acad. Sci. USA 86: 8959–8963 (1989).

Klarlund, Transformation of cells by an inhibitor of phosphatases acting on phosphotryrosine in proteins, Cell 41: 707–717 (1985).

Beckmann and Bork, An adhevsive domain detected in functionally diverse receptors, trends Biochm.Sci. 18:40–41 (1993).

O'Bryan et al., axl, a transforming gene islated from primary human myeloid leukemia cells, encodes a novel receptor tyrosine kinase. Mol. Cell. Biol. 11:5016–5031 (1991).

Rescigno et al., A putative receptor tyrosine kinase with unique structural topology. Oncogene 6:1909–1913 (1991).

Burgoon et al., Structure of chicken neuron–glia cell adhesion molecule, Ng–CAM: origin of the polypeptides and relation to the Ig superfamily. J. Cell. Biol. 112:1017–1029 (1991).

Bieber et al., Drosophila neuroglian: a member of the immunoglobulin superfamily with extensive homology to the vertebrate neural adhesion molecule L1. Cell 59:447–460 (1989).

Takagi et al., The A5 antigen, a candidate for the neuronal recognition molecule, has homologies to complement components and coagulation factors. Neuron 7:295–307 (1991).

Blaschuk et al., Identification of a conserved region common to cadherins and Influenza strain A hemagglutinins. J. Mol. Biol. 211:679–682 (1990).

Hosaka et al., Arg–X–Lys/Arg–Arg motif as a signal for precursor cleavage catalyzed by furin within the constitutive secretory pathway. J. Biol. Chem. 266:12127–12130 (1991).

Kornblihtt et al., Primary structure of human fibronectin: differential spllicing may generate at least 10 polypeptides from a single gene. EMBO J. 4:1755–1759 (1985).

Schlessinger and Ullrich, Growth factor signaling by receptor tyrosine kinases. Neuron 9:383–391 (1992).

Pot and Dixon, A thousand and two protein tyrosine phosphatases, Biochem. Biophys. Acta. 1136: 35–43 (1992).

Fischer et al., Protein tyrosine phosphatases: A diverse family of intracellular and trasnmembrane enzymes, Science 253: 401–406 (1991).

Saito et al., Molecular characterization of protein ryrosine phosphatase, Cell Growth Differ. 2:59–65 (1991).

Klausner and Samelson, T cell antigen receptor activation pathways: The tyrosine kinase connection. Cell 64:875–878 (1991).

Kjellen and Lindahl, Proteoglycans: structures and interactions. Ann. Rev. Biochem. 60:443–475 (1991).

Ullrich and Schlessinger, Signal transduction by receptors with tyrosine kinase activity. Cell. 61:203–212 (1990).

Hunter, Protein–tyrosine phosphatases: The other side of the coin, Cell 58: 1013–1016 (1989).

Thomas, The leukocyte common antigen family, Ann. Rev. Immunol. 7: 339–369 (1989).

Yarden and Ullrich, growth factor receptor tyrosine kinases. Ann. Rev. Biochem. 57:443–478 (1988).

| | | |
|---|---|---|
| SIGNAL PEPTIDE | 1 atggatgtggcggccgctgcgttgcctgcttttgtagctctctggcttctgtacccgtgg<br>1 [M D V A A A A L P A F V A L W L L Y P W | 60<br>20 |
| | 61 cctctcctggggtcggcccttggccagttctcagcaggtggctgtacttttgatgatggg<br>21 P L L G S] A L G Q F S A [G G C T F D D G | 120<br>40 |
| A5 HOMOLOGY REGION | 121 ccaggggcttgtgactaccaccaggatttatacgatgactttgagtgggtccatgtcagt<br>41 P G A C D Y H Q D L Y D D F E W V H V S | 180<br>60 |
| | 181 gcgcaggaacctcattacctgccccccgaaatgcctcaaggttcctatatggttgtggac<br>61 A Q E P H Y L P P E M P Q G S Y M V V D | 240<br>80 |
| | 241 tcctcaaatcatgatcctggagaaaaagccagacttcagctgcctaccatgaaggagaat<br>81 S S N H D P G E K A R L Q L P T M K E N | 300<br>100 |
| | 301 gacacccactgcattgatttcagttacctgttatatagccagaaggggttgaaccctggc<br>101 D T H C I D F S Y L L Y S Q K G L N P G | 360<br>120 |
| | 361 actttgaatatcctagttagggtgaataaaggacctcttgctaatccaatttggaatgta<br>121 T L N I L V R V N K G P L A N P I W N V | 420<br>140 |
| | 421 actggattcactggtcgtgattggcttcgggctgaactagctgtgagcacctttggccc<br>141 T G F T G R D W L R A E L A V S T F W P | 480<br>160 |
| | 481 aatgaataccaggtaatatttgaagctgaagtctcaggagggagaagtggttatattgcc<br>161 N E Y Q V I F E A E V S G G R S G Y I A | 540<br>180 |
| | 541 attgatgacatccaagtcctgagttatccttgcgataaatctcctcattttctccgcctt<br>181 I D D I Q V L S Y] P C D K S P H F L R L | 600<br>200 |

FIG.1A

```
601  ggtgatgtggaggtcaatgctgggcagaatgctacatttcagtgcattgctacagggaga  660
201   G  D  V  E  V  N  A  G  Q  N  A  T  F  Q  C  I  A  T  G  R   220

661  gatgctgtgcataacaagttatggctgcagagacgcaatggagaagacatacccgtagcc  720
221   D  A  V  H  N  K  L  W  L  Q  R  R  N  G  E  D  I  P  V  A   240

721  cagactaagaacataaatcacagaagatttgctgcctctttcagattgcaagaagtgaca  780
241   Q  T  K  N  I  N  H  R  R  F  A  A  S  F  R  L  Q  E  V  T   260

781  aaaactgaccaggatttgtaccgctgcgtaactcagtcagaacgaggttctggggttttcc  840
261   K  T  D  Q  D  L  Y  R  C  V  T  Q  S  E  R  G  S  G  V  S   280

841  aattttgctcaactcattgtgagagaaccacctagacccattgctcctccccagctgctt  900
281   N  F  A  Q  L  I  V  R  E  P  P  R  P  I  A  P  P  Q  L  L   300

901  ggtgttgggcctacttacttgctgatccaactaaatgccaactctattattggcgatggc  960
301   G  V  G  P  T  Y  L  L  I  Q  L  N  A  N  S  I  I  G  D  G   320

961  cccatcatcctgaaagaagtagagtatcgaatgacatcaggatcttggacagaaacccat  1020
321   P  I  I  L  K  E  V  E  Y  R  M  T  S  G  S  W  T  E  T  H   340

1021 gcagtcaacgcaccaacatataagttgtggcatttagacccagatacagaatacgagatc  1080
341   A  V  N  A  P  T  Y  K  L  W  H  L  D  P  D  T  E  Y  E  I   360

1081 cgcgtcctgcttaccagacctggcgaaggggggaactgggctgccaggaccaccactgatc  1140
361   R  V  L  L  T  R  P  G  E  G  G  T  G  L  P  G  P  P  L  I   380

1141 actagaacgaagtgtgcagaacctatgcggacaccaaagactttaaagattgctgaaatc  1200
381   T  R  T  K  C  A  E  P  M  R  T  P  K  T  L  K  I  A  E  I   400
```

FIG.1B

```
1201  caggcaaggcgcattgcagtggactggggagtccttgggctacaacatcactcgttgccac  1260
 401   Q   A   R   R   I   A   V   D   W   E   S   L   G   Y   N   I   T   R   C   H      420

1261  actttcaacgtcactatctgctaccattacttccgtggccacaatgagagcagggcagac  1320
 421   T   F   N   V   T   I   C   Y   H   Y   F   R   G   H   N   E   S   R   A   D      440

1321  tgcttggacatggaccccaaagcccctcagcatgttgtgaaccatctgccaccttacaca  1380
 441   C   L   D   M   D   P   K   A   P   Q   H   V   V   N   H   L   P   P   Y   T      460

1381  aatgtcagcctcaagatgatcctaaccaacccagaggggaaggaaggagagcgaagagaca  1440
 461   N   V   S   L   K   M   I   L   T   N   P   E   G   R   K   E   S   E   E   T      480

1441  atcatccaaactgatgaagatgtgcccgggcctgtgccagtcaaatccctccaaggaaca  1500
 481   I   I   Q   T   D   E   D   V   P   G   P   V   P   V   K   S   L   Q   G   T      500

1501  tcctttgaaaacaagatcttcctgaactggaaagagccactggaaccgaatggaattatc  1560
 501   S   F   E   N   K   I   F   L   N   W   K   E   P   L   E   P   N   G   I   I      520

1561  actcagtatgaggtgagctatagcagcataagatcatttgaccctgctgttccagtggct  1620
 521   T   Q   Y   E   V   S   Y   S   S   I   R   S   F   D   P   A   V   P   V   A      540

1621  gggcccccacagactgtatcaaatttatggaatagtacacaccatgtatttatgcatctt  1680
 541   G   P   P   Q   T   V   S   N   L   W   N   S   T   H   H   V   F   M   H   L      560

1681  caccctggaaccacctaccagttttttataagagccagcactgtcaaaggctttggacca  1740
 561   H   P   G   T   T   Y   Q   F   F   I   R   A   S   T   V   K   G   F   G   P      580

1741  gcaacagccatcaatgtgaccacaaatatctcagctccaagcttacctgactatgaagga  1800
 581   A   T   A   I   N   V   T   T   N   I   S   A   P   S   L   P   D   Y   E   G      600
```

FIG.1C

```
1801 gttgatgcctctctgaatgaaactgccaccaccatcacagtactattgaggcctgcacaa 1860
601   V  D  A  S  L  N  E  T  A  T  T  I  T  V  L  L  R  P  A  Q  620

1861 gccaaaggtgctcctatcagtgcttatcaaattgttgtggagcagctacacccacatcga 1920
621   A  K  G  A  P  I  S  A  Y  Q  I  V  V  E  Q  L  H  P  H  R  640

1921 acgaagcgtgaagcaggggccatggaatgctaccaggtaccggttacataccagaacgcc 1980
641   T  K  R  E  A  G  A  M  E  C  Y  Q  V  P  V  T  Y  Q  N  A  660

1981 ctaagtgggggcgcgccctattactttgccgcagaacttccccctgggaatcttcccgag 2040
661   L  S  G  G  A  P  Y  Y  F  A  A  E  L  P  P  G  N  L  P  E  680

2041 cctgctcccttcaccgtgggtgacaaccggacctataaaggcttttggaaccctcccctg 2100
681   P  A  P  F  T  V  G  D  N  R  T  Y  K  G  F  W  N  P  P  L  700

2101 gcccccccgcaaaggatacaacatctatttccaagcgatgagcagtgtggagaaggaaact 2160
701   A  P  R  K  G  Y  N  I  Y  F  Q  A  M  S  S  V  E  K  E  T  720

2161 aaaacccaatgtgtacgaattgctacaaaagcagcagcaacagaagaaccagaagtgatc 2220
721   K  T  Q  C  V  R  I  A  T  K  A  A  A  T  E  E  P  E  V  I  740

2221 ccagacccggcaaagcagacagacagagtggtgaaaatcgcgggcatcagtgctggcatc 2280
741   P  D  P  A  K  Q  T  D  R  V  V  K [I  A  G  I  S  A  G  I  760

2281 ctagtgttcatccttctcctgctggttgtcatagtaattgtgaaaaagagcaagcttgct 2340
761   L  V  F  I  L  L  L  V  V  I  V  I  V] K  K  S  K  L  A  780

2341 aagaagcgcaaagatgcaatggggaacacacgtcaggagatgacccacatggtgaatgct 2400
781   K  K  R  K  D  A  M  G  N  T  R  Q  E  M  T  H  M  V  N  A  800
```

TRANS-
MEMBRANE (bracket at residues 751-773)

FIG.1D

```
           2401  atggaccgaagttatgctgaccagagcaccctgcatgcagaagacccccttccctcacc  2460
            801   M  D  R  S  Y  A  D  Q  S  T  L  H  A  E  D  P  L  S  L  T   820

2461  ttcatggaccaacataacttcagtccaagattgcccaatgatccacttgtgccgactgcc  2520
            821   F  M  D  Q  H  N  F  S  P  R  L  P  N  D  P  L  V  P  T  A   840

2521  gtgttagatgagaaccacagtgccacagcagagtctagtcgtctcctggatgttcctcga  2580
            841   V  L  D  E  N  H  S  A  T  A  E  S  S  R  L  L  D  V  P  R   860

2581  tacctctgcgaagggacagagtcccttatcagacaggacagctgcacccagccatcagg  2640
            861   Y  L  C  E  G  T  E  S  P  Y  Q  T  G  Q  L  H  P  A  I  R   880

2641  gtggccgacttactgcagcacattaacctcatgaagacatcagacagctatgggttcaaa  2700
            881   V  A  D  L  L  Q  H  I  N  L  M  K  T  S  D  S  Y  G  F  K   900

2701  gaggaatacgagagcttctttgaaggccagtcagcctcttgggatgtggctaaaaaggat  2760
            901   E  E  Y  E  S  F  F  E  G  Q  S  A  S  W  D  V  A  K  K  D   920

PTPase     2761  caaaacagagcaaagaaccgatacggaaacattatcgcatatgatcactccagagtcatc  2820
DOMAIN I    921   Q  N  R  A  K [N  R  Y  G  N  I  I  A  Y  D  H  S  R  V  I   940

2821  ctgcaacctgtggaagatgacccttcttcagattacattaatgccaactacatcgacatt  2880
            941   L  Q  P  V  E  D  D  P  S  S  D  Y  I  N  A  N  Y  I  D  I   960

2881  tggctgtacagggatggctaccagagaccaagccactacattgcaactcaaggcccagtt  2940
            961   W  L  Y  R  D  G  Y  Q  R  P  S  H  Y  I  A  T  Q  G  P  V   980

2941  catgaaaccgtatatgattttggaggatggtgtggcaagagcagtctgcctgtattgtg  3000
            981   H  E  T  V  Y  D  F  W  R  M  V  W  Q  E  Q  S  A  C  I  V  1000
```

FIG.1E

```
3001  atggtcactaatttagtggaagttggccgggtgaaatgctataaatattggcctgatgat  3060
1001   M  V  T  N  L  V  E  V  G  R  V  K  C  Y  K  Y  W  P  D  D   1020

3061  actgaggtttatggtgacttcaaagtcacctgcgtagaaatggagccacttgctgagtat  3120
1021   T  E  V  Y  G  D  F  K  V  T  C  V  E  M  E  P  L  A  E  Y   1040

3121  gtcgttaggacattcaccttggaaaggaggggctataatgaaatccgtgaagtcaaacag  3180
1041   V  V  R  T  F  T  L  E  R  R  G  Y  N  E  I  R  E  V  K  Q   1060

3181  ttccacttcactggctggcctgaccatggtgttccataccacgcaacagggctcctgtca  3240
1061   F  H  F  T  G  W  P  D  H  G  V  P  Y  H  A  T  G  L  L  S   1080

3241  tttatccggagagtcaagctatctaacccctcccagtgctgggcccattgtcgtacactgc  3300
1081   F  I  R  R  V  K  L  S  N  P  P  S  A  G  P  I  V  V  H  C   1100

3301  agtgctggtgctgggcgcacaggctgttacattgttattgacataatgctggacatggct  3360
1101   S  A  G  A  G  R  T  G  C  Y  I  V  I  D  I  M  L  D  M  A   1120

3361  gaaagagagggtgtggttgacatctacaactgtgtgaaagccttacgatctcggcgcatt  3420
1121   E  R  E  G  V  V  D  I  Y  N  C  V  K  A  L  R  S  R  R  I   1140

3421  aatatggtacagacagaggaacagtacattttttattcatgatgccatttttagaagcctgc  3480
1141   N  M  V  Q  T  E  E  Q  Y  I  F  I  H  D  A  I  L  E] A  C   1160

3481  ttatgtggagaaactgccatccctgtgtgtgaatttaaagctgcatattttgatatgatt  3540
1161   L  C  G  E  T  A  I  P  V  C  E  F  K  A  A  Y  F  D  M  I   1180

3541  cgaatagactctcagactaactcctctcatctcaaagatgaatttcagactctgaattcg  3540
1161   L  C  G  E  T  A  I  P  V  C  E  F  K  A  A  Y  F  D  M  I   1180
```

FIG.1F

```
              3541 cgaatagactctcagactaactcctctcatctcaaagatgaatttcagactctgaattcg 3600
              1181  R  I  D  S  Q  T  N  S  S  H  L  K  D  E  F  Q  T  L  N  S  1200

PTPase        3601 gtcacccctcgactacaagctgaagactgcagcatagcctgcctgccaaggaaccatgac 3660
DOMAIN II     1201  V  T  P  R  L  Q  A  E  D  C  S  I  A  C  L  P  R [N  H  D  1220

3661 aagaaccgtttcatggatatgctcccacctgacagatgtctgcctttttttaattacaatt 3720
              1221  K  N  R  F  M  D  M  L  P  P  D  R  C  L  P  F  L  I  T  I  1240

3721 gatggggagagcagtaactacatcaatgctgctcttatggatagctataggcagccagca 3780
              1241  D  G  E  S  S  N  Y  I  N  A  A  L  M  D  S  Y  R  Q  P  A  1260

3781 gctttcatcgtcacacaataccccactgccaaacactgtgaaagacttctggagattagta 3840
              1261  A  F  I  V  T  Q  Y  P  L  P  N  T  V  K  D  F  W  R  L  V  1280

3841 tatgattacggatgtacctccatcgtgatgctaaatgaagtggacctgtctcagggctgc 3900
              1281  Y  D  Y  G  C  T  S  I  V  M  L  N  E  V  D  L  S  Q  G  C  1300

3901 ccacagtactggccagaagaaggaatgctgcgatatggtcctatccaagtggaatgtatg 3960
              1301  P  Q  Y  W  P  E  E  G  M  L  R  Y  G  P  I  Q  V  E  C  M  1320

3961 tcttgttcaatggactgtgatgtgatcaatcgaatttttagaatatgcaacctaacgaga 4020
              1321  S  C  S  M  D  C  D  V  I  N  R  I  F  R  I  C  N  L  T  R  1340

4021 ccacaggagggctatctgatggtacaacagttccagtacctaggctgggcttctcatcga 4080
              1341  P  Q  E  G  Y  L  M  V  Q  Q  F  Q  Y  L  G  W  A  S  H  R  1360

4081 gaagtgcctggctccaaacgctcgttttttgaaattgatactgcaggtggaaaaatggcaa 4140
              1361  E  V  P  G  S  K  R  S  F  L  K  L  I  L  Q  V  E  K  W  Q  1380
```

FIG.1G

```
4141 gaggaatgtgaagaaggggaaggccggacaatcatccactgcttgaatggcggtgggcgc 4200
1381  E  E  C  E  E  G  E  G  R  T  I  I  H  C  L  N  G  G  R     1400

4201 agtggcatgttctgtgccataggcattgttgtggagatggtgaagcggcaaaatgtggtg 4260
1401  S  G  M  F  C  A  I  G  I  V  V  E  M  V  K  R  Q  N  V  V  1420

4261 gatgttttccatgcagtaaaagacgctgaggaacagcaagccaaacatggtggaagccccg 4320
1421  D  V  F  H  A  V  K  T  L  R  N  S  K  P  N  M  V  E  A  P  1440

4321 gagcagtatcgttttgctatgatgtggcgttagagtacctggagtcctcatag 4374
1441  E  Q  Y  R  F  C  Y  D  V  A  L  E  Y  L  E] S  S  *  1458
```

FIG.1H

FIG.3

```
                    *        *             *           *         *       *  *        *          *      *      *    * **    *  *
I   (296)  P PQL L GVGPTYLLIQLNANS I IGDGPIILKEVE Y RMTSGSWTETHAVNAPTYKLWHLDPDTE YEIRVLL T R RG EG G TGLPGPPLITRT
II  (392)  P .KT L KIAEIQA..RRIAVD W ESLGYNITRCHT F NVTICYHYFRGHNESRADCLDMDPKA...PQHVVNH L P PY TN V SLKMIL.TNPEG
III (493)  P VKS L QCTSFE...NKIFLN W KEPLEPNGIITQ Y EVSYSSIRSFDPAVPVAGPPQTVSNLWNSTHHVFMH L H PG TT Y QFFIRASTVKGF
IV  (596)  P DYE G VDASLNETATTITVL L RPAQAKGAPISA Y QIVWEQLHPHRTKR.EAGAMECYQV.....PVTYQNA L S GG AP Y YFAAELPPGNLP
FBN-III(7) P PTN L HLEANPDT.GVLTVS W ERSTIPD..ITG Y RITITPTNGQQGNSLEEVVHADQ.......SSCTFDN L S PG LE Y NVSVY..TVKDD
```

FIG.4

```
PTP-κ(34)   GGCTFDDGPGACDYHQDLYDDFEWVHVSAQE.PHYLPPEMPQGSYMVVDSSNHDPGEKARLQLPTMKEN.DTHCIDFSYLLYSQK
PTP-μ(26)   GGCLFDEPYSTCGYSQADEDDFNMEQVNTLTKPT.SDPWMPSGSFMLVNTSGKPEGQRAHLLLPQLKEN.DTHCIDFHYFVSSKS
A5  (651)   CKFGWGSQKTVCNWQHDISSDLKWAVLNSKTGP..VQDHTGDGNF IYSEADERHEGRAARLMSPVVSSSRSAHCLTFWYHM...D
Consensus   ——————————C————D——W————N——T—P——————G—F——————————EG——ARL——P————————HC——F—Y——

PTP-κ       GLNPCTLNILVRVN.KGPLANPIWNVTGFTGRDWLRAELAVSTFWPNEYQVIFEAEVSGGRSGYIAIDDIQVLSY
PTP-μ       NAAPGLLNVYVKVN.NGPLGNPIWNISGDPTRTMHRAELAISTFWPNFYQVIFEV.VTSGHQGYLAIDEVKVLGH
A5          GSHVGTLSIKLKYEMEEDFDQTLWTVSGNQGDQWKEARVVLHKTMKQ.YQVIVEGTVGKGSAGGIAVDDIIIANH
Consensus   G———GTL—I—K————————W—VSG—G——W—A—————YQVI—E——V——G—IA—DDI———H
```

FIG.5

```
  1 ATGGATACGACTGCGGCGGCGGCGCTGCCTGCTTTTGTGGCGCTCTTGCTCCTCTCTCCTTGGCCTCTCCTGGGATCGGC  80
  1 M  D  T  T  A  A  A  A  L  P  A  F  V  A  L  L  L  L  S  P  W  P  L  L  G  S  A   27

81 CCAAGGCCAGTTCTCCGCAGGTGGCTGTACTTTTGATGATGGTCCAGGGGCCTGTGATTACCACCAGGATCTGTATGATG 160
 27 Q  G  Q  F  S  A  G  G  C  T  F  D  D  G  P  G  A  C  D  Y  H  Q  D  L  Y  D  D   53

161 ACTTTGAATGGGTGCATGTTAGTGCTCAAGAGCCTCATTATCTACCACCCGAGATGCCCCAAGGTTCCTATATGATAGTG 240
 54 F  E  W  V  H  V  S  A  Q  E  P  H  Y  L  P  P  E  M  P  Q  G  S  Y  M  I  V      80

241 GACTCTTCAGATCACGACCCTGGAGAAAAAGCCAGACTTCAGCTGCCTACAATGAAGGAGAACGACACTCACTGCATTGA 320
 81 D  S  S  D  H  D  P  G  E  K  A  R  L  Q  L  P  T  M  K  E  N  D  T  H  C  I  D  107

321 TTTCAGTTACCTATTATATAGCCAGAAAGGACTGAATCCTGGCACTTTGAACATATTAGTTAGGGTGAATAAAGGACCTC 400
107 F  S  Y  L  L  Y  S  Q  K  G  L  N  P  G  T  L  N  I  L  V  R  V  N  K  G  P  L  133

401 TTGCCAATCCAATTTGGAATGTGACTGGATTCACGGGTAGAGATTGGCTTCGGGCTGAGCTAGCAGTGAGCACCTTTTGG 480
134 A  N  P  I  W  N  V  T  G  F  T  G  R  D  W  L  R  A  E  L  A  V  S  T  F  W      160

481 CCCAATGAATATCAGGTAATATTTGAAGCTGAAGTCTCAGGAGGGAGAAGTGGTTATATTGCCATTGATGACATCCAAGT 560
161 P  N  E  Y  Q  V  I  F  E  A  E  V  S  G  G  R  S  G  Y  I  A  I  D  D  I  Q  V  187

561 ACTGAGTTATCCTTGTGATAAATCTCCTCATTTCCTCCGTCTAGGGGATGTAGAGGTGAATGCAGGGCAAAACGCTACAT 640
187 L  S  Y  P  C  D  K  S  P  H  F  L  R  L  G  D  V  E  V  N  A  G  Q  N  A  T  F  213

641 TTCAGTGCATTGCCACAGGGAGAGATGCTGTGCATAACAAGTTATGGCTCCAGAGACGAAATGGAGAAGATATACCAGTA 720
214 Q  C  I  A  T  G  R  D  A  V  H  N  K  L  W  L  Q  R  R  N  G  E  D  I  P  V      240

721 GCCCAGACTAAGAACATCAATCATAGAAGGTTTGCCGCTTCCTTCAGATTGCAAGAAGTGACAAAAACTGACCAGGATTT 800
241 A  Q  T  K  N  I  N  H  R  R  F  A  A  S  F  R  L  Q  E  V  T  K  T  D  Q  D  L  267

801 GTATCGCTGTGTAACTCAGTCAGAACGAGGTTCCGGTGTGTCCAATTTTGCTCAACTTATTGTGAGAGAACCGCCAAGAC 880
267 Y  R  C  V  T  Q  S  E  R  G  S  G  V  S  N  F  A  Q  L  I  V  R  E  P  P  R  P  293

881 CCATTGCTCCTCCTCAGCTTCTTGGTGTTGGGCCTACATATTTGCTGATCCAACTAAATGCCAACTCGATCATTGGCGAT 960
294 I  A  P  P  Q  L  L  G  V  G  P  T  Y  L  L  I  Q  L  N  A  N  S  I  I  G  D     320

961 GGTCCTATCATCCTGAAAGAAGTAGAGTACCGAATGACATCAGGATCCTGGACAGAAACCCATGCAGTCAATGCTCCAAC 1040
321 G  P  I  I  L  K  E  V  E  Y  R  M  T  S  G  S  W  T  E  T  H  A  V  N  A  P  T  347
```

FIG.15A

```
1041 TTACAAATTATGGCATTTAGATCCAGATACCGAATATGAGATCCGAGTTCTACTTACAAGACCTGGTGAAGGTGGAACGG 1120
 347   Y  K  L  W  H  L  D  P  D  T  E  Y  E  I  R  V  L  L  T  R  P  G  E  G  G  T  G  373

1121 GGCTCCCAGGACCTCCACTAATCACCAGAACAAAATGTGCAGAACCTATGAGAACCCCAAAGACATTAAAGATTGCTGAA 1200
 374   L  P  G  P  P  L  I  T  R  T  K  C  A  E  P  M  R  T  P  K  T  L  K  I  A  E  400

1201 ATACAGGCAAGACGGATTGCTGTGGACTGGGAATCCTTGGGTTACAACATTACGCGTTGCCACACTTTTAATGTCACTAT 1280
 401   I  Q  A  R  R  I  A  V  D  W  E  S  L  G  Y  N  I  T  R  C  H  T  F  N  V  T  I  427

1281 CTGCTACCATTACTTCCGTGGTCACAACGAGAGCAAGGCAGACTGTTTGGACATGGACCCCAAAGCCCCTCAGCATGTTG 1360
 427   C  Y  H  Y  F  R  G  H  N  E  S  K  A  D  C  L  D  M  D  P  K  A  P  Q  H  V  V  453

1361 TGAACCATCTGCCACCTTATACAAATGTCAGCCTCAAGATGATCCTAACCAATCCAGAGGGAAGGAAGGAGAGTGAAGAG 1440
 454   N  H  L  P  P  Y  T  N  V  S  L  K  M  I  L  T  N  P  E  G  R  K  E  S  E  E  480

1441 ACAATTATTCAAACTGATGAAGATGTGCCTGGTCCCGTACCAGTAAAATCTCTTCAAGGAACATCCTTTGAAAATAAGAT 1520
 481   T  I  I  Q  T  D  E  D  V  P  G  P  V  P  V  K  S  L  Q  G  T  S  F  E  N  K  I  507

1521 CTTCTTGAACTGGAAAGAACCTTTGGATCCAAATGGAATCATCACTCAATATGAGATCAGCTATAGCAGTATAAGATCAT 1600
 507   F  L  N  W  K  E  P  L  D  P  N  G  I  I  T  Q  Y  E  I  S  Y  S  S  I  R  S  F  533

1601 TTGATCCTGCAGTCCCAGTGGCTGGACCTCCCCAGACTGTATCAAATTTATGGAACAGTACACACCATGTCTTTATGCAT 1680
 534   D  P  A  V  P  V  A  G  P  P  Q  T  V  S  N  L  W  N  S  T  H  H  V  F  M  H  560

1681 CTCCACCCTGGAACCACGTACCAGTTTTTCATAAGAGCCAGCACGGTCAAAGGCTTTGGTCCAGCCACAGCCATCAATGT 1760
 561   L  H  P  G  T  T  Y  Q  F  F  I  R  A  S  T  V  K  G  F  G  P  A  T  A  I  N  V  587

1761 CACCACCAATATCTCAGCTCCAACTTTACCTGACTATGAAGGAGTTGATGCCTCTCTCAATGAAACTGCCACCACAATAA 1840
 587   T  T  N  I  S  A  P  T  L  P  D  Y  E  G  V  D  A  S  L  N  E  T  A  T  T  I  T  613

1841 CTGTATTGTTGAGACCAGCACAAGCCAAAGGTGCTCCTATCAGTGCTTATCAGATTGTTGTGGAAGAACTGCACCCACAC 1920
 614   V  L  L  R  P  A  Q  A  K  G  A  P  I  S  A  Y  Q  I  V  V  E  E  L  H  P  H  640

1921 CGAACCAAGAGAGAAGCCGGAGCCATGGAATGCTACCAGGTTCCTGTCACATACCAAAATGCCATGAGTGGGGGTGCACC 2000
 641   R  T  K  R  E  A  G  A  M  E  C  Y  Q  V  P  V  T  Y  Q  N  A  M  S  G  G  A  P  667

2001 GTATTACTTTGCTGCAGAACTACCCCCGGGAAACCTACCTGAGCCTGCCCCGTTCACTGTGGGTGACAATCGGACCTACC 2080
 667   Y  Y  F  A  A  E  L  P  P  G  N  L  P  E  P  A  P  F  T  V  G  D  N  R  T  Y  Q  693

2081 AAGGCTTTTGGAACCCTCCTTTGGCTCCGCGCAAAGGATACAACATCTATTTCCAGGCGATGAGCAGTGTGGAGAAGGAA 2160
 694   G  F  W  N  P  P  L  A  P  R  K  G  Y  N  I  Y  F  Q  A  M  S  S  V  E  K  E  720
```

FIG.15B

```
2161  ACTAAAACCCAGTGCGTACGCATTGCTACAAAAGCAGCAACAGAAGAACCAGAAGTGATCCCAGATCCCGCCAAGCAGAC  2240
 721   T  K  T  Q  C  V  R  I  A  T  K  A  A  T  E  E  P  E  V  I  P  D  P  A  K  Q  T   747

2241  AGACAGAGTGGTGAAAATAGCAGGAATTAGTGCTGGAATTTTGGTGTTCATCCTCCTTCTCCTAGTTGTCATATTAATTG  2320
 747   D  R  V  V  K  I  A  G  I  S  A  G  I  L  V  F  I  L  L  L  L  V  V  I  L  I  V   773

2321  TAAAAAAGAGCAAACTTGCTAAAAAACGCAAAGATGCCATGGGGAATACCCGGCAGGAGATGACTCACATGGTGAATGCA  2400
 774    K  K  S  K  L  A  K  K  R  K  D  A  M  G  N  T  R  Q  E  M  T  H  M  V  N  A    800

2401  ATGGATCGAAGTTATGCTGATCAGAGCACTCTGCATGCAGAAGATCCTCTTTCCATCACCTTCATGGACCAACATAACTT  2480
 801   M  D  R  S  Y  A  D  Q  S  T  L  H  A  E  D  P  L  S  I  T  F  M  D  Q  H  N  F   827

2481  TAGTCCAAGATATGAGAACCACAGTGCTACAGCAGAGTCCAGTCGCCTTCTAGACGTACCTCGCTACCTCTGTGAGGGGA  2560
 827   S  P  R  Y  E  N  H  S  A  T  A  E  S  S  R  L  L  D  V  P  R  Y  L  C  E  G  T   853

2561  CGGAATCCCCTTACCAGACAGGACAGCTGCATCCAGCCATCAGGGTAGCTGATTTACTGCAGCACATTAATCTCATGAAG  2640
 854    E  S  P  Y  Q  T  G  Q  L  H  P  A  I  R  V  A  D  L  L  Q  H  I  N  L  M  K    880

2641  ACATCAGACAGCTATGGGTTCAAAGAGGAATATGAGAGCTTTTTTGAAGGACAGTCAGCATCTTGGGATGTAGCTAAAAA  2720
 881   T  S  D  S  Y  G  F  K  E  E  Y  E  S  F  F  E  G  Q  S  A  S  W  D  V  A  K  K   907

2721  AGATCAAAATAGAGCAAAAAACCGATATGGAAACATTATAGCATATGATCACTCCAGAGTGATTTTGCAACCCGTAGAGG  2800
 907   D  Q  N  R  A  K  N  R  Y  G  N  I  I  A  Y  D  H  S  R  V  I  L  Q  P  V  E  D   933

2801  ATGATCCTTCCTCAGATTATATTAATGCCAACTATATTGATGGCTACCAGAGACCAAGTCATTACATTGCAACCCAAGGT  2880
 934    D  P  S  S  D  Y  I  N  A  N  Y  I  D  G  Y  Q  R  P  S  H  Y  I  A  T  Q  G    960

2881  CCCGTTCATGAAACAGTGTATGATTTCTGGAGGATGATTTGGCAAGAACAATCTGCTTGCATTGTGATGGTTACAAATTT  2960
 961   P  V  H  E  T  V  Y  D  F  W  R  M  I  W  Q  E  Q  S  A  C  I  V  M  V  T  N  L   987

2961  AGTTGAGGTTGGCCGGGTTAAATGCTATAAATATTGGCCTGATGATACTGAAGTTTATGGTGACTTCAAAGTAACGTGTG  3040
 987   V  E  V  G  R  V  K  C  Y  K  Y  W  P  D  D  T  E  V  Y  G  D  F  K  V  T  C  V  1013

3041  TAGAAATGGAACCACTTGCTGAATATGTAGTTAGGACATTCACCCTGGAAAGGAGGGGGTACAATGAAATCCGTGAAGTT  3120
1014    E  M  E  P  L  A  E  Y  V  V  R  T  F  T  L  E  R  R  G  Y  N  E  I  R  E  V   1040

3121  AAACAGTTCCATTTCACGGGCTGGCCTGACCATGGAGTGCCCTACCATGCTACAGGGCTGCTTTCCTTTATCCGGCGAGT  3200
1041   K  Q  F  H  F  T  G  W  P  D  H  G  V  P  Y  H  A  T  G  L  L  S  F  I  R  R  V  1067
```

FIG.15C

```
3201 CAAGTTATCAAACCCTCCCAGTGCTGGCCCCATCGTTGTACATTGCAGTGCTGGTGCTGGACGAACTGGCTGCTACATTG 3280
1067   K  L  S  N  P  P  S  A  G  P  I  V  V  H  C  S  A  G  A  G  R  T  G  C  Y  I  V  1093

3281 TGATTGACATCATGCTAGACATGGCTGAAAGAGAGGGTGTTGTTGATATTTACAATTGTGTCAAAGCCTTAAGATCTCGG 3360
1094   I  D  I  M  L  D  M  A  E  R  E  G  V  V  D  I  Y  N  C  V  K  A  L  R  S  R  1120

3361 CGTATTAATATGGTCCAGACAGAGGAACAGTACATTTTTATTCATGATGCCATTTTAGAAGCCTGCTTATGTGGAGAAAC 3440
1121   R  I  N  M  V  Q  T  E  E  Q  Y  I  F  I  H  D  A  I  L  E  A  C  L  C  G  E  T  1147

3441 TGCCATACCTGTCTGTGAATTTAAAGCTGCATATTTTGATATGATTAGAATAGACTCCCAGACTAACTCTTCACATCTCA 3520
1147   A  I  F  V  C  E  F  K  A  A  Y  F  D  M  I  R  I  D  S  Q  T  N  S  S  H  L  K  1173

3521 AGGATGAATTTCAGACTCTGAATTCAGTCACCCCTCGACTACAAGCTGAAGACTGCAGTATAGCGTGCCTGCCAAGGAAC 3600
1174    D  E  F  Q  T  L  N  S  V  T  P  R  L  Q  A  E  D  C  S  I  A  C  L  P  R  N  1200

3601 CATGACAAGAACCGTTTCATGGACATGCTGCCACCTGACAGATGTCTGCCTTTTTTAATTACAATTGATGGGGAGAGCAG 3680
1201   H  D  K  N  R  F  M  D  M  L  P  P  D  R  C  L  P  F  L  I  T  I  D  G  E  S  S  1227

3681 TAACTACATCAATGCTGCTCTTATGGACAGCTACAGGCAACCAGCTGCTTTCATCGTCACACAATACCCTCTGCCAAACA 3760
1227   N  Y  I  N  A  A  L  M  D  S  Y  R  Q  P  A  A  F  I  V  T  Q  Y  P  L  P  N  T  1253

3761 CTGTAAAAGACTTCTGGAGATTAGTGTATGATTATGGCTGTACCTCCATTGTGATGTTAAACGAAGTCGACTTGTCCCAG 3840
1254    V  K  D  F  W  R  L  V  Y  D  Y  G  C  T  S  I  V  M  L  N  E  V  D  L  S  Q  1280

3841 GGCTGCCCTCAGTACTGGCCAGAGGAAGGGATGCTACGATATGGCCCCATCCAAGTGGAATGTATGTCTTGTTCAATGGA 3920
1281   G  C  P  Q  Y  W  P  E  E  G  M  L  R  Y  G  P  I  Q  V  E  C  M  S  C  S  M  D  1307

3921 CTGTGATGTGATCAACCGGATTTTTAGGATATGCAATCTAACAAGACCACAGGAAGGTTATCTGATGGTGCAACAGTTTC 4000
1307   C  D  V  I  N  R  I  F  R  I  C  N  L  T  R  P  Q  E  G  Y  L  M  V  Q  Q  F  Q  1333

4001 AGTACCTAGGATGGGCTTCTCATCGAGAAGTGCCTGGATCCAAAAGGTCATTCTTGAAACTGATACTTCAGGTGGAAAAG 4080
1334    Y  L  G  W  A  S  H  R  E  V  P  G  S  K  R  S  F  L  K  L  I  L  Q  V  E  K  1360

4081 TGGCAGGAGGAATGCGAGGAAGGGGAAGGCCGGACGATTATCCACTGCCTAAATGGTGGCGGGCGAAGTGGCATGTTCTG 4160
1361 W  Q  E  E  C  E  E  G  E  G  R  T  I  I  H  C  L  N  G  G  R  S  G  M  F  C  1387

4161 TGCTATAGGCATCGTTGTTGAAATGGTGAAACGGCAAAATGTTGTCGATGTTTTCCATGCAGTAAAGACACTGAGGAACA 4240
1387   A  I  G  I  V  V  E  M  V  K  R  Q  N  V  V  D  V  F  H  A  V  K  T  L  R  N  S  1413
```

FIG.15D

```
4241  GCAAGCCAAACATGGTGGAAGCCCCGGAGCAATACCGTTTCTGCTATGATGTAGCTTTGGAGTACCTGGAATCATCTTAG  4320
1414    K  P  N  M  V  E  A  P  E  Q  Y  R  F  C  Y  D  V  A  L  E  Y  L  E  S  S  *    1439
                                                                          SEQ. ID NO: 2
4321  TTGGGTGAGACTCTTTAAAGTGCATCCATGAAGAAACCTGTCCATCTATTGAGCCAGCAGCTGTTGTACCTGTTACACTT  4400
4401  GTGCAGAAAGATTTTAATGTGGGGGGTGGGAGACTTTTACATTTGAGAGGTAAAAGTATTTTTTTTATGAAGTTGTGTAT  4480
4481  CTTAATAAAAAGAACTGAATTAGTTTTTATTACTATATTAAAGCATCAACATTTCATGCCACATAAAATTATATTTAATA  4560
4561  AGAACCAGATTGAAATGAGAACGTATTGGTGTTTGTACAGTGAACATGCCACCTTTTTCCATGGTTTCAGGTAGTGCAGC  4640
4641  TACCACATGTT  4651
           SEQ. ID NO: 4
```

FIG.15E

```
                                                                            ********
MCP7    MDTTAAAALPAPVALLLLSPMPLLGSAQQQPSAGGCTFDDGPCACDYHQDLYDDFEWHVSAQEPHYLPPEMPQGSYMIV    80
hRPTPμ  -MRLGTC-TLG     -TAAGET  -  L  EPYST G S SEG   N EQ NILTKPTSD W S L L           71

MCP7    DSSDHDPGEKARLQLPTMKENDTHCIDFSYLLYSQKGLNPGTLNILVRVNKGPLANPIWNVTGFTGRDWLRAELAVSTFW  160
hRPTPμ  NA GRPE QR H L  QL       H FVS KSNSP  L  VY K N  G     IS DPT T N       I        151

MCP7    PNEYQVIFEAEVSGGRSGYIAIDDIQVLSYPCDKSPHFLRLGDVEVNAGQNATFQCIATGRDAVHNKLWLQRRNGEDIPV  240
hRPTPμ  F    V-ITS HQ  L  EVK GH TRT     ICN     P    SI  TVAGDR    GIDVR A L           230

MCP7    AQTKNINHRRFAASFRLQEVTKTDQDLYRCVIQSERGSGVSNFAQLIVREPRRPIAPPQLLGVGPTYLLIQLNANSIIGD  320
hRPTPμ  KEI VTSS   I   NVVNT R AGK  MIRT G V I Y EV K V       AS A  W          N         310

MCP7    GPIILKEVEYRMTSGSWTETHAVNAPTYKLWHLDPDTEYEIRVLLTRPGEGGTGLPGPPLITRTKCAEPMRTPKTLKIAE  400
hRPTPμ  VAR    CTA   NDRQP DSTS  IG         S            S A R       D   G RK EVV        390

MCP7    IQARRIAVDMWESLGYNITRCHTFNVTICYHYFRGHNE--SKADCLDMDPKAPQHVVNHLPPYTNVSLKMILTNPEGRKES  478
hRPTPμ  VKS Q TIR PF   V   SY L VH C  QV GQ QVREEVSW TENSH   TITN S        V L M          470

MCP7    EETIIQTDEDVPGPVPVKSLQGTSFENKIFLMWKEPLDPNGIITQYEISYSSIRSFDPAVPVAGPPQTVSNLWNSTHHVF  558
hRPTPμ  QLV  L  A   TE I ST E     QR TQIY V L  T KAVS     EIDLSNQSGR  K G E  FL          550

MCP7    MHLHPGTTYQFFIRASTVKGFGPATAINVTNISAPTLPDYEGVDASLNETATTITVLLRPAQAKGAPISAYQIVWEELH  638
hRPTPμ  PG Y   ST   A    PATNQF K  SM A  -LETP  Q DN V M K HSR   V V        ER         629

MCP7    PHRTKREAGAMECYQVPVTYQNAMSGGAPYYFAAELPPGNLPEPAPFTVGDNRTYQGFMNPPLAPRKGYNIYFQAMSSVE  718
hRPTPμ  R   KITEILK  P  IHF   SLLNSQ      F ADS QAAQ    I K N Y T L Y S R    A RAN      709

FIG.16A
```

FIG. 16B

```
MCP7    KETKTQCVRIATKAATEEPEVIPDPAKQTDRVVKIAGISAGILVFILLLLVVILIVKKSKLAKKRKDAMGNTRQEMTHMV    798
hRPTPμ  G  ID QV  G A-T KPV E E    HT    VI   L VIIF G V VM  R           ET SS      V     788

MCP7    NAMDRSYADQSTLHAEDPLSITFMDQHNFSPRY———————————ENHSATAESSRLLDVPRY-LCE                  852
hRPTPμ  S  K  E G -NCDEAF  —  T  LNG SVSSPSSFTMKTNTLSTSVPNSYYPD T TMASDT S VQSHT  KKR     865

MCP7    GTESPYQTGQLHPAIRVADILQHINLMKTSDSYGFKEYESFFEGQSASMDVAKKDQNRAKNRYGNIIAYDHSRVILQPV     932
hRPTPμ  PADV          TQ CAEG                    P  S      E   M              R  TI      945

MCP7    EDDPSSDYINANYIDGYQRPSHYIATQGPVHETVYDFWRMIWQESACIVMVTNLVEVGRVKCYKYWPDDTEVYGDFKVT     1012
hRPTPμ  G TN   G      H N      MQ  I       VHNTSI       C              I K I            1025

MCP7    CVEMEPLAEYVVRTFTLERRGYNEIREVKQFHFTGWPDHGVPYHATGLLSFIRRVKLSNPPSAGPIVVHCSAGAGRTGCY    1092
hRPTPμ  LITL    I    AV K VH    IR                        GVQ SKS       L            F   1105

MCP7    IVIDIMLDMAEREGVVDIYNCVKALRSRRINMVQTEEQYIFIHDAILEACLCGETAIPVCEFKAAYFDMIRIDSQTNSSH    1172
hRPTPμ               RE   V     V              D SV ASQVRSL Y  NKL  P      Q            1185

MCP7    LKDEFQTLNSVTPRLQAEDCSIACLPRNHDKNRFMDMLPPDRCLPFLITIDGESSNYINAALMDSYRQPAAFIVTQYPLP    1252
hRPTPμ  IE R    M   T RV         L    E C I                             K S       H      1265

MCP7    NTVKDFWRLVYDGCTSIVMLNEVDLSQGCPQYWPEEGMLRYGPIQVECMSCSMDCDVINRIFRICNLTRPQEGYLMVQQ     1332
hRPTPμ           L   H  V    D PA L      N VH H        FV ADLEE I S     YAA   D R         1345

MCP7    FQYLGWASHREVPGSKRSFLKLILQVEKMQEECEEGEGRTIIHCLNGGGRSGMFCAIGIVVEMVKRQNVDVFHAVKTLR     1412
hRPTPμ  F    PMY DT V       R  D     YNG  P VV               T     S C  LRH RT            1425

MCP7    NSKPNMVEAPEQYRFCYDVALEYLESS*                                                        1439
hRPTPμ  N   DLLD K      E         NG*                                                      1452
```

κ⁻(dil)+κ⁺

κ⁻+κ⁺(dil)

κ⁺+κ⁺(dil)

NUCLEIC ACID ENCODING NOVEL RECEPTOR-TYPE PHOSPHOTYROSINE PHOSPHATASE-κ

CROSS REFERENCE TO RELATED APPLICATION

This application is a continuation-in-part application of U.S. application Ser. No. 08/049,384 filed Apr. 21, 1993, now abandoned.

TABLE OF CONTENTS

1. INTRODUCTION
2. BACKGROUND OF THE INVENTION
   2.1. PTKases
   2.2. PTPases
3. SUMMARY OF THE INVENTION
4. DESCRIPTION OF THE FIGURES
5. DETAILED DESCRIPTION OF THE INVENTION
6. EXAMPLE: ISOLATION AND ANALYSIS OF MURINE RPTPκ cDNA CLONES
   6.1. LIBRARY SCREENING
   6.2. NUCLEOTIDE SEQUENCE DETERMINATION
   6.3. SEQUENCE ALIGNMENTS
   6.4. RESULTS AND DISCUSSION
      6.4.1. ISOLATION AND SEQUENCE ANALYSIS OF cDNA CLONES ENCODING MURINE RPTPκ
7. EXAMPLE: EXPRESSION AND TISSUE DISTRIBUTION OF RPTPκ
   7.1. TISSUE EXPRESSION AND NORTHERN ANALYSIS
      7.1.1. EXPRESSION OF THE RPTPκ PROTEIN
      7.1.2. GENERATION OF ANTISERA SPECIFIC FOR EPITOPES OF RPTPκ
      7.1.3. TRANSFECTION, LABELING AND IMMUNOPRECIPITATION
      7.1.4. PROTEIN TYROSINE PHOSPHATASE ENZYMATIC ASSAY
      7.1.5. ENDOGLYCOSIDASE F TREATMENT
      7.1.6. SITE-DIRECTED MUTAGENESIS
      7.1.7. IN SITU HYBRIDIZATION OF RPTPκ cDNA TO RAT TISSUES
   7.2. RESULTS AND DISCUSSION
      7.2.1. EXPRESSION OF RPTPκ IN ADULT TISSUES
      7.2.2. TRANSIENT EXPRESSION AND ENZYMATIC ACTIVITY OF RPTPκ
      7.2.3. IN SITU HYBRIDIZATION ANALYSIS OF RPTPκ EXPRESSION IN THE DEVELOPING AND ADULT CENRAL NERVOUS SYSTEM
8. EXAMPLE: CHROMOSOMAL LOCALIZATION OF THE MURINE RPTPκ
9. EXAMPLE:
10. EXAMPLE: ISOLATION AND ANALYSIS OF HUMAN RPTPκ (MCP7) cDNA CLONES
    10.1. PCR AND cDNA CLONING METHODS
    10.2. RESULTS
    10.3. DISCUSSION
11. EXAMPLE: TISSUE DISTRIBUTION OF HUMAN RPTPκ
    11.1. RNA EXTRACTION AND NORTHERN BLOT ANALYSIS
    11.2. RESULTS
12. EXAMPLE: TRANSIENT EXPRESSION OF HUMAN RPTPκ
    12.1. METHODS
    12.2. RESULTS
13. EXAMPLE: EXAMINATION OF PTPase ENZYMATIC ACTIVITY OF HUMAN RPTPκ
14. EXAMPLE: CORRELATION BETWEEN HUMAN RPTPκ EXPRESSION AND CELL DENSITY
15. Example: Homophilic Binding by a Receptor Tyrosine Phosphatase
    15.1. Discussion

1. INTRODUCTION

The invention in the field of biochemistry and cell and molecular biology relates to novel receptor-type protein tyrosine phosphatase protein or glycoprotein, termed RPTPκ (also known as RPTPase-κ), DNA coding therefore, methods for production and identification of the protein, methods for screening compounds capable of binding to and inhibiting or stimulating PTPase enzymatic activity, methods for inhibiting homophilic binding of RPTPκ, and methods for identifying compounds which are capable of inhibiting homophilic RPTPκ binding.

2. BACKGROUND OF THE INVENTION

Tyrosine phosphorylation of proteins is involved in an increasing number of cellular signalling events. It was originally implicated in signalling by paracrine- or autocrine-acting growth factors, and endocrine hormones such as insulin (see Yarden, Y. et al., Annu. Rev. Biochem. 57:443–478 (1988) for review). It is now clear that this posttranslational modification is also involved in diverse processes such as the activation of cells of the immune system by antigens (Klausner, R. D. et al., Cell 64:875–878), signalling by lymphokines (Hatakeyama, M. et al., 1991 Science 252:1523–1528 (1991); Mills, G. B. et al., J. Biol. Chem. 265:3561–3567 (1990)), and cellular differentiation and survival (Fu, X.-Y. 1992 Cell 70:323–335; Schlessinger, J. et al. 1992 Neuron 9:1–20; Velazquez, L. et al., 1992 Cell 70:313–322). In view of the diversity of processes in which tyrosine phosphorylation is involved, it is not surprising that links are also emerging with the process of cell adhesion and cell—cell contact.

The identification of several growth factor receptors and retroviral oncogenes as tyrosine-specific protein kinases indicated that protein phosphorylation on tyrosine residues plays a key role in cellular growth control. This notion has recently received support by the observation that the level of tyrosine phosphorylation of enzymes thought to play an important role in signal transduction (such as phospholipase C) correlates with their increased activity upon growth factor stimulation, thus establishing a functional role for tyrosine phosphorylation (Ullrich, A., et al., *Cell* 61:203–212 (1990)).

Most of the processes in which tyrosine phosphorylation is implicated involve the transduction of a signal through the cell membrane. In its best understood fashion, this can occur through dimerization-mediated activation of members of the receptor tyrosine kinase family by soluble ligands (reviewed in Ullrich, A. et al. 1990 Cell 61:203–212). However, modulation of receptor tyrosine kinase activity can also occur by membrane-bound ligands on neighboring cells, as in the case of the interaction between the sevenless kinase and the bride of sevenless protein (Rubin, G. M. 1991, Trends in Genetics 7:372–376). Recently, receptor-like tyrosine kinases were described with an extracellular domain similar to that of cell adhesion molecules of the CAM-family (e.g. Axl and Ark (O'Bryan, J. P. et al., 1991 Mol. Cell. Biol. 11:5016–5031; Rescigno, J. et al., 1991

Oncogene 6:1909–1913)). Such observations may implicate tyrosine phosphorylation as a more broadly used direct downstream effector mechanism for precise cell—cell recognition and signalling events. Members of the non-receptor family of tyrosine kinases have also in several instances been shown to be associated with other proteins with a trans-membrane topology, examples being the association of the Lck and Fyn kinases with the CD4 protein and T-cell receptor complex components respectively (Haughn, L. et al., 1992 Nature 358:328–331; Samelson, L. E. et al., 1992 Proc. Natl. Acad. Sci. USA 87:4358–4362; Veillette, A. et al., 1988 Cell 55:301–308). However, the mechanism by which kinase activity is modulated in these instances is not understood.

The degree and pattern of phosphorylation of tyrosine residues on cellular proteins are regulated by the opposing activities of protein-tyrosine kinases (PTKases; ATP:protein-tyrosine O-phosphotransferase, EC 2.7.1.112) and protein-tyrosine-phosphatases (PTPases; protein-tyrosine-phosphate phosphohydrolase, EC 3.1.3.48). The structural characteristics and evolution of PTKases as well as their role in the regulation of cell growth have been reviewed (Hunter, T., et al., Annu. Rev. Biochem. 54:897–930 (1985); Ullrich, A., et al., supra).

2.1. PTKases

Tyrosine kinases comprise a discrete family of enzymes having common ancestry with, but major differences from, serine/threonine-specific protein kinases (Hanks, S. K. et al., (1988) Science 241:42–52). The mechanisms leading to changes in activity of tyrosine kinases are best understood for receptor-type tyrosine kinases which have a transmembrane topology (Ullrich, A. et al., supra). With such kinases, the binding of specific ligands to the extracellular domain of these enzymes is thought to induce their oligomerization leading to an increase in tyrosine kinase activity and activation of the signal transduction pathways (Ullrich, A. et al., supra). The importance of this activity is supported by the knowledge that dysregulation of kinase activity through mutation or over-expression is a mechanism for oncogenic transformation (Hunter, T. et al., supra; Ullrich, A. et al., 1990, supra).

2.2. PTPases

The protein phosphatases are composed of at least two separate and distinct families (Hunter, T. Cell, 58:1013–1016 (1989)), the protein serine/threonine phosphatases and the protein tyrosine phosphatases. This is in contrast to protein kinases, which show clear sequence similarity between serine/threonine-specific and tyrosine-specific enzymes.

There appear to be two basic types of PTPase molecules. The first group is comprised of small, soluble enzymes that contain a single conserved phosphatase catalytic domain, and include (1) placental PTPase 1B (Charbonneau, H. et al., Proc. Natl. Acad. Sci. 86:5252–5256 (1989); Chernoff, J. et al., Proc. Natl. Acad. Sci. USA 87:2735–2789 (1990)), (2) T-cell PTPase (Cool, D. E. et al., Proc. Natl. Acad. Sci. USA 86:5257–5261 (1989)), and (3) rat brain PTPase (Guan, K., et al., Proc. Natl. Acad. Sci. USA, 87:1501–1505 (1990).

The identification of a tyrosine phosphatase homology domain has raised new interest in the potential of PTPases to act as modulators of tyrosine phosphorylation (Kaplan, R. et al. 1990 Proc. Natl. Acad. Sci. USA 87:7000–7004; Krueger, N. X. et al., 1990 EMBO J. 9:3241–3252; see, for review, Fischer, E. H. et al., 1991 Science 253:401–406).

The second group of PTPases is made up of the more complex, receptor-linked PTPases, termed R-PTPases or RPTPs, which are of high molecular weight and contain two tandemly repeated conserved domains separated by 56–57 amino acids. RPTPs may be further subdivided into four types based on structural motifs within their extracellular segments.

One example of RPTPs are the leukocyte common antigens (LCA) (Ralph, S. J., EMBO J., 6:1251–1257 (1987); Charbonneau, H., et al., Proc. Natl. Acad. Sci. USA, 85:7182–7186 (1988)). LCA, also known as CD45, T200 and Ly-5 (reviewed in Thomas, M. L., Ann. Rev. Immunol. 7:339–369 (1989)) comprises a group of membrane glycoproteins expressed exclusively in hemopoietic (except late erythroid) cells, derived from a common gene by alternative splicing events involving the amino terminus of the proteins.

Other examples of RPTPs are the LCA-related protein, LAR (Streuli, M. et al., J. Exp. Med., 168:1523–1530 (1988)), and the LAR-related Drosophila proteins DLAR and DPTP (Streuli, M., et al., Proc. Natl. Acad. Sci. USA, 86:8698–8702 (1989)). Jirik et al. screened a cDNA library derived from the human hepatoblastoma cell line, HepG2, with a probe encoding the two PTPase domains of LCA (FASEB J. 4:A2082 (1990), abstr. 2253) and discovered a cDNA clone encoding a new RPTP, named He-PTP. The HePTP gene appeared to be expressed in a variety of human and murine cell lines and tissues.

A large number of members of the RPTP family, called type II RPTPs, display an extracellular domain containing a combination of Ig-domains and fibronectin type III repeats (Fn-III), features typically encountered in cell adhesion molecules (CAMs) (Gebbink, M. F. B. G. et al., 1991 FEBS Lett. 290:123–130; Streuli, M. et al., 1988 J. Exp. Med. 168: 1523–1530). An analysis of the expression patten of several R-PTPases in the developing Drosophila CNS suggests some function of these molecules in aspects of axon guidance and outgrowth (Tian, S. S. et al., 1991 Cell 67:675–685; Yang, X. et al., 1991. Cell 67:661–673), an observation winch might be related to the ability of R-PTPases to control the activity of src-family tyrosine kinases (Mustelin, T. et al., 1989 Proc. Natl. Acad. Sci. USA 86:6302–6306; Ostergaard, H. L. et al., 1989 Proc. Natl. Acad. Sci. USA 86:8959–8963; Zheng, X. M. et al., 1992 Nature 359:336–339). Other studies have raised the possibility that certain R-PTPases may function as tumor suppressor genes, e.g. by controlling contact inhibition (LaForgia, S. et al., 1991 Proc. Natl. Acad. Sci. USA 88:5036–5040). Elevation of cellular phosphotyrosine may occur through mechanisms other than the activation of a tyrosine kinase itself. For instance, expression of the v-crk oncogene, though not a tyrosine kinase, induces the phosphorylation of tyrosine residues through a poorly understood mechanism (Mayer, B. J. et al. (1988) Nature 332, 272–275). Potentially, such an outcome could result from either mutation of the substrate or through a general decrease in cellular phosphatase activity, especially in view of the normally high turnover rate of cellular tyrosine-phosphate (Sefton, B. M. et al. (1980) Cell 20:807–816). The latter possibility is suggested by the demonstration that tyrosine phosphatase inhibitors can "reversibly transform" cells (Klarlund, J. K. Cell 41: 707–717 (1985)). PTPases could therefor act as recessive oncogenes.

While we are beginning to understand more about the structure and diversity of the PTPases, much remains to be learned about their cellular functions. Thus, a better understanding of, and an ability to control, phosphotyrosine metabolism, requires knowledge not only the role of PTKase activity, but the action of PTPase enzymes as well. It is clear in the art that further delineation of structure-function relationships among these PTPases and RPTP membrane receptors are needed to gain important understanding of the mechanisms of cell growth, differentiation, and oncogenesis.

3. SUMMARY OF THE INVENTION

The present inventors have conceived of a role for RPTPs in cellular control mechanisms, both as potential anti-oncogenes, and as effectors in a newly discovered mechanism of transmembrane signalling. They therefore undertook a search for individual RPTP genes and proteins in mammals, including humans, which are potentially involved in such processes, and describe herein the identification of a novel, widely expressed member of the RPTP family, RPTPκ, in both mice and in humans which has a transmembrane topology. The novel human RPTPκ disclosed herein consists of two associated subunits whose expression is modulated by cell-to-cell contact, and, in a manner analogous to receptor tyrosine kinases, is subject to direct regulation by extracellular ligands which bind to the extracellular portion. Further, as is demonstrated in the Working Example presented in Section 15, infra, RPTPκ is shown to homophilically bind other RPTPκ molecules.

The present invention thus provides a mammalian, preferably a human, receptor-type protein tyrosine phosphatase-κ (RPTPκ) protein or glycoprotein molecule, a functional derivative of the RPTPκ, or a homolog of the RPTPκ in another mammalian species. When the RPTPκ molecule is of natural origin, it is substantially free of other proteins or glycoproteins with which it is natively associated. RPTPκ is naturally expressed in mammalian brain and is developmentally and anatomically regulated. It is also expressed in other mammalian tissues. The RPTPκ molecule of the present invention may also be prepared by chemical synthesis or by or recombinant means. Thus, the substantially pure RPTPκ protein or glycoprotein of the present invention may be produced by biochemical purification of the protein or glycoprotein of natural origin or by production using chemical synthesis or by recombinant expression in prokaryotic or eukaryotic hosts.

Figure 3:
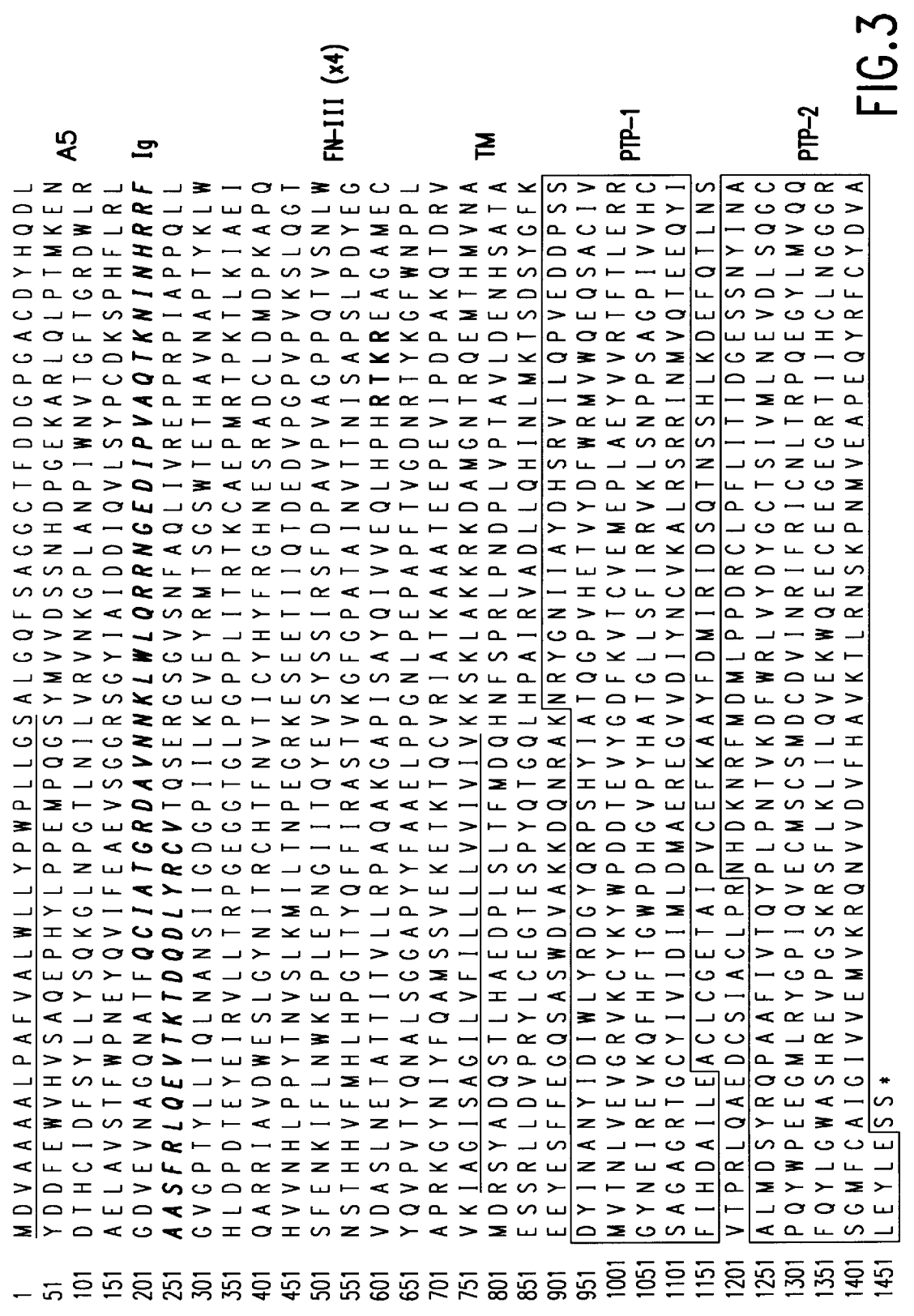

In particular, the invention is directed to a mammalian RPTPκ protein or glycoprotein having the amino acid sequence of RPTPκ shown in FIG. 3 (SEQ ID NO:1). In another embodiment is provided a functional derivative thereof. Preferably, the RPTPκ is of human origin, and has the amino acid sequence SEQ ID NO:2, as shown in FIGS. 15A–15F.

The invention is further directed to a nucleic acid molecule, preferably DNA, which may consist essentially of a nucleotide sequence encoding a mammalian RPTPκ having the nucleotide sequence SEQ ID NO:3 (FIGS. 1(1)–1(5). Preferably, the nucleic acid molecule consists essentially of a nucleotide sequence encoding human RPTPκ and having the nucleotide sequence SEQ ID NO:4 or encodes a functional derivative thereof. The DNA molecule is preferably cDNA or genomic DNA. The invention is further directed to the DNA molecule in the form of an expression vehicle, as well as prokaryotic and eukaryotic hosts transformed or transfected with the DNA molecule.

Also included in the present invention is a process for preparing a RPTPκ protein or glycoprotein, or a functional derivative thereof, comprising:
 (a) culturing a host capable of expressing the protein, glycoprotein or functional derivative under culturing conditions,
 (b) expressing the protein, glycoprotein or functional derivative; and
 (c) recovering the protein, glycoprotein or functional derivative from the culture.

This invention is also directed to an antibody, either polyclonal, monoclonal, or chimeric, which is specific for the RPTPκ protein or glycoprotein.

This invention is also directed to a method for detecting the presence of nucleic acid encoding a normal or mutant RPTPκ in a cell or in a subject, comprising:
 (a) contacting a cell or an extract thereof from the subject with an oligonucleotide probe encoding at least a portion of a normal or mutant RPTPκ under hybridizing conditions; and
 (b) measuring the hybridization of the probe to the nucleic acid of the cell, thereby detecting the presence of the nucleic acid, preferably DNA.

The DNA can be selectively amplified, using the polymerase chain reaction, prior to assay.

The invention is further directed to a method for detecting the presence, or measuring the quantity of RPTPκ in a cell or cells, comprising:
 (a) contacting said cell or an extract thereof with an antibody specific for an epitope of RPTPκ; and
 (b) detecting the binding of the antibody to the cell or extract thereof, or measuring the quantity of antibody bound,
thereby detecting the presence or measuring the quantity of the RPTPκ.

The present invention is also directed to methods for identifying and isolating a compound capable of binding to RPTPκ from a chemical or biological preparation comprising:
 (a) attaching RPTPκ, or the ligand-binding portion thereof, to a solid phase matrix;
 (b) contacting the chemical or biological preparation with the solid phase matrix allowing the compound to bind, and washing away any unbound material;
 (c) detecting the presence of the compound bound to the solid phase matrix; and, for purposes of isolation,
 (d) eluting the bound compound, thereby isolating the compound.

Further, the present invention includes a method for identifying an agent capable of stimulating or inhibiting the phosphatase enzymatic activity of RPTPκ, comprising:
 (a) contacting the agent with the RPTPκ in pure form, in a membrane preparation, or in a whole live or fixed cell;
 (b) incubating the mixture in step (a) for a sufficient interval;
 (c) measuring the enzymatic activity of the RPTPκ;
 (d) comparing the enzymatic activity to that of the RPTPκ incubated without the agent,
thereby determining whether the agent stimulates or inhibits the enzymatic activity.

Still further, the invention provides methods for inhibiting the homophilic binding of Type II RPTP, preferably the homophilic binding of RPTPκ, provides methods for identifying agents capable of inhibiting such Type II RPTP homophilic binding, and methods for inhibiting endogenous Type II RPTP homophilic binding in mammalian subjects.

4. DESCRIPTION OF THE FIGURES

FIGS. 1A–1H shows the complete nucleotide sequence [SEQ ID NO:3] and amino acid sequence [SEQ ID NO:1] of murine RPTPκ. The signal peptide, A5 homology region, transmembrane domain, and PTPase domains are designated by brackets.

FIG. 2 is a schematic representation of the various RPTPκ cDNA clones isolated, and the proposed domain structure of the RPTPκ protein. Translational start and stop codons as well as restriction sites mentioned in the text are indicated. The vertical arrow indicates the position of the furin cleavage site. TM: transmembrane segment.

FIG. 3 shows the predicted amino acid sequence [SEQ ID NO:1] of the RPTPκ precursor protein. The putative signal peptide and transmembrane (TM) segment are underlined. The two tandem phosphatase domains are boxed (PTP-1, PTP-2). The proteolytic cleavage site (RTKR 640–643) is printed in bold, and the Ig-like domain (Ig, 214–270) shown in bold italic characters. A5: homology to A5 surface protein (Takagi, S. et al., 1991 Neuron 7:295–307); FN-III: fibronectin type III repeats. The Genbank accession number for the cDNA sequence is L10106.

FIG. 4 shows a proposed alignment of the four FN-III repeats of RPTPκ [SEQ ID NO:1] and domain 7 of human fibronectin [SEQ ID NO:5] (Kornblihtt, A. R. et al., 1985 EMBO J. 4:1755–1759). Residues most typically conserved in FN-III repeats are highlighted in bold. Residues identical in three or more out of the five aligned sequences are indicated with an asterisk. This region of the protein also contains clearly detectable homology to LAR, Drosophila PTPase 10D, and Drosophila neuroglian, all of which have been reported to contain FN-III repeats.

FIG. 5 shows an alignment of the N-terminal domains of RPTPκ [SEQ ID NO:1] and mRPTPμ [SEQ ID NO:6] with the cell surface protein A5 [SEQ ID NO:7] (Takagi et al., supra). Numbers indicate the first residue of the respective proteins shown in the alignment. Residues marked as consensus are identical between A5 and RPTPκ, or between A5 and mRPTPμ. Conservative substitutions are present but not shown. Residues in bold (C,W) define a possible Ig-like domain structure.

Figure 6:
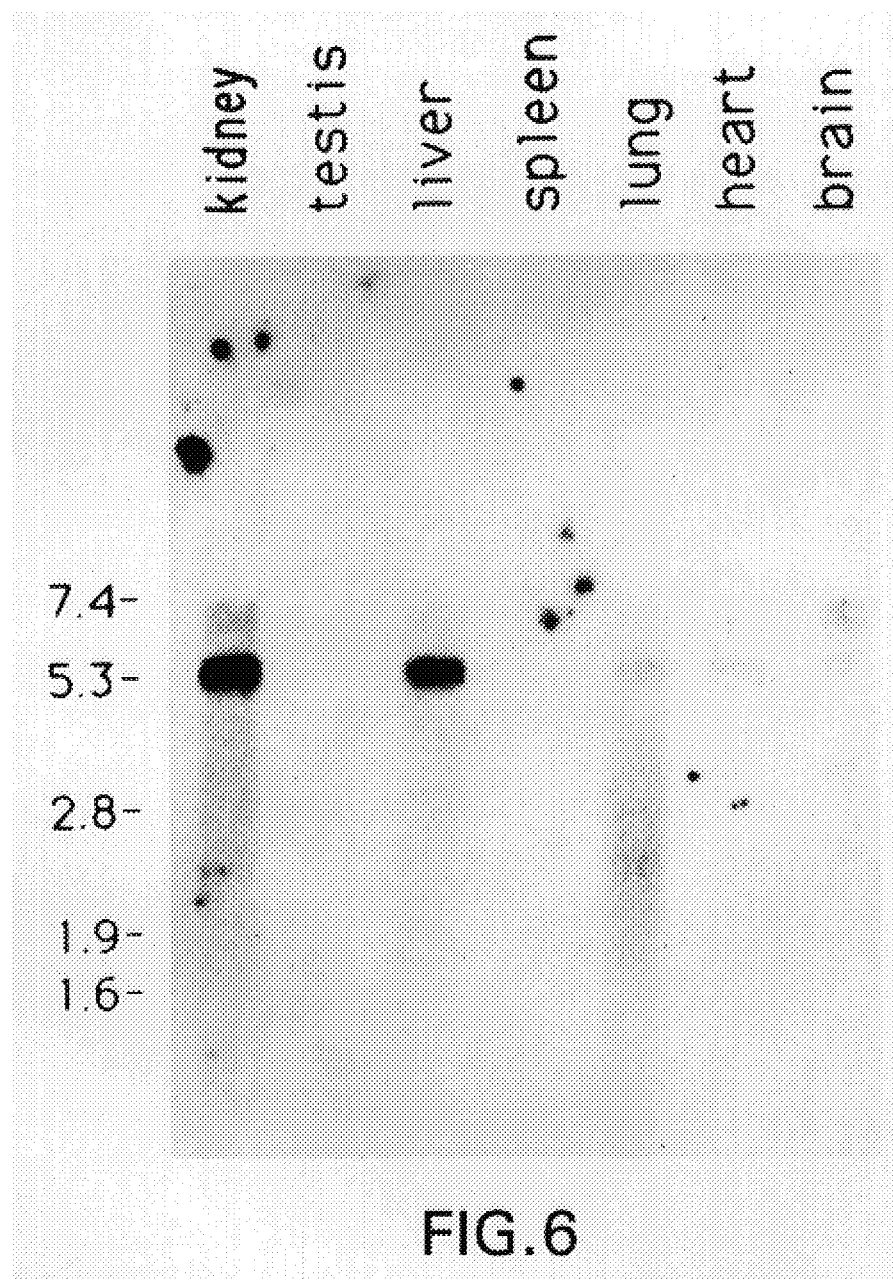

FIG. 6 shows the expression of RPTPκ mRNA in adult tissues using Northern blot analysis of poly(A)+RNA from various mouse tissues. The entire cDNA fragment from clone λ-604 was used as a probe. A similar pattern of hybridization was seen using as a probe the λ-50 cDNA clone and the N-terminal half of the λ-35 cDNA clone. Positions of RNA molecular weight markers, in kb, are indicated on the left side.

Figure 7:
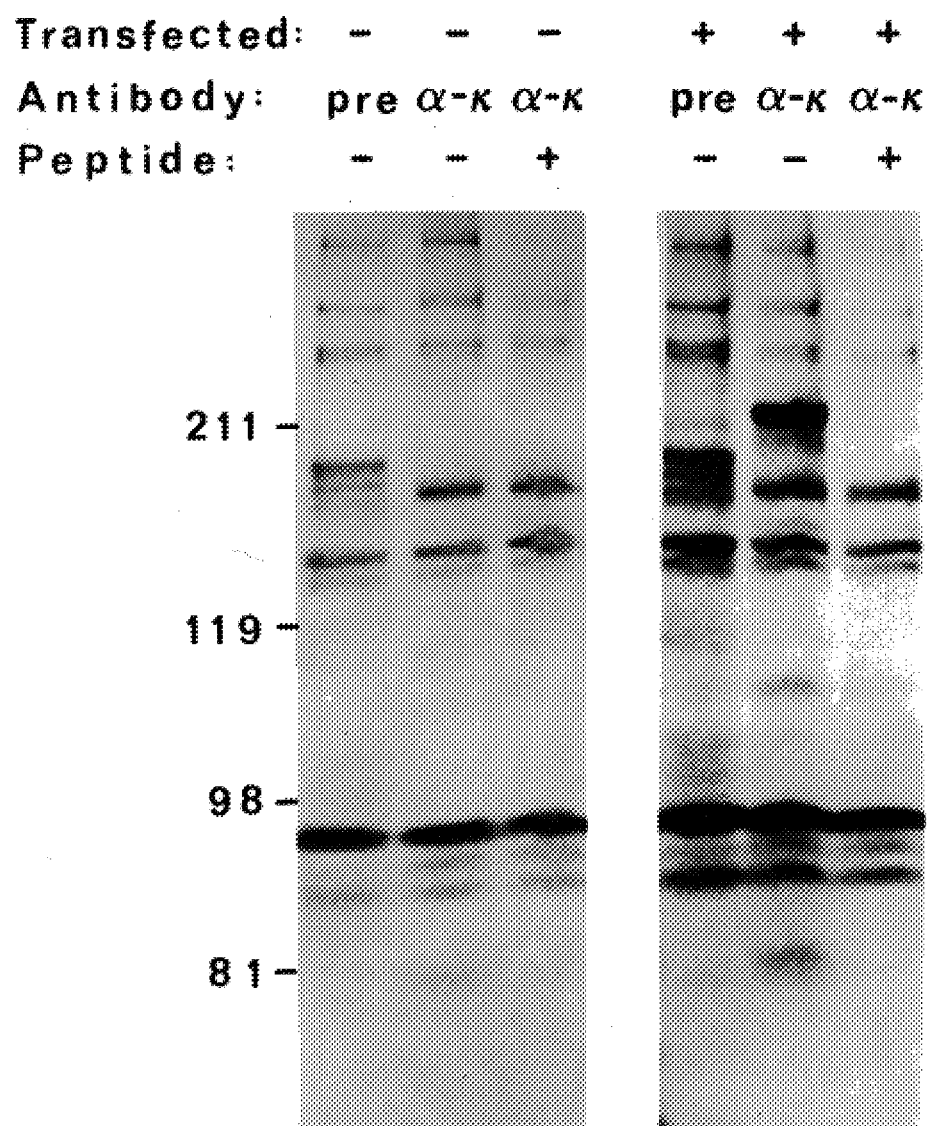

FIG. 7 is a gel pattern showing the immunoprecipitation of the RPTPκ protein. HeLa cells transiently transfected by the calcium phosphate technique with an RPTP-ic expression vector (+) or an empty expression vector (−) were analyzed by radio-immunoprecipitation using antiserum 116 directed against a synthetic peptide corresponding to residues 60 to 76 in the extracellular domain. The immunoprecipitation was performed in the absence (−) or presence (+) of 20 μg of the immunogenic peptide (a-κ: anti RPTPκ antiserum 116; pre: corresponding preimmune serum). Positions of protein molecular weight standards (expressed in kDa) are indicated on the left side of the autoradiogram.

Figure 8:
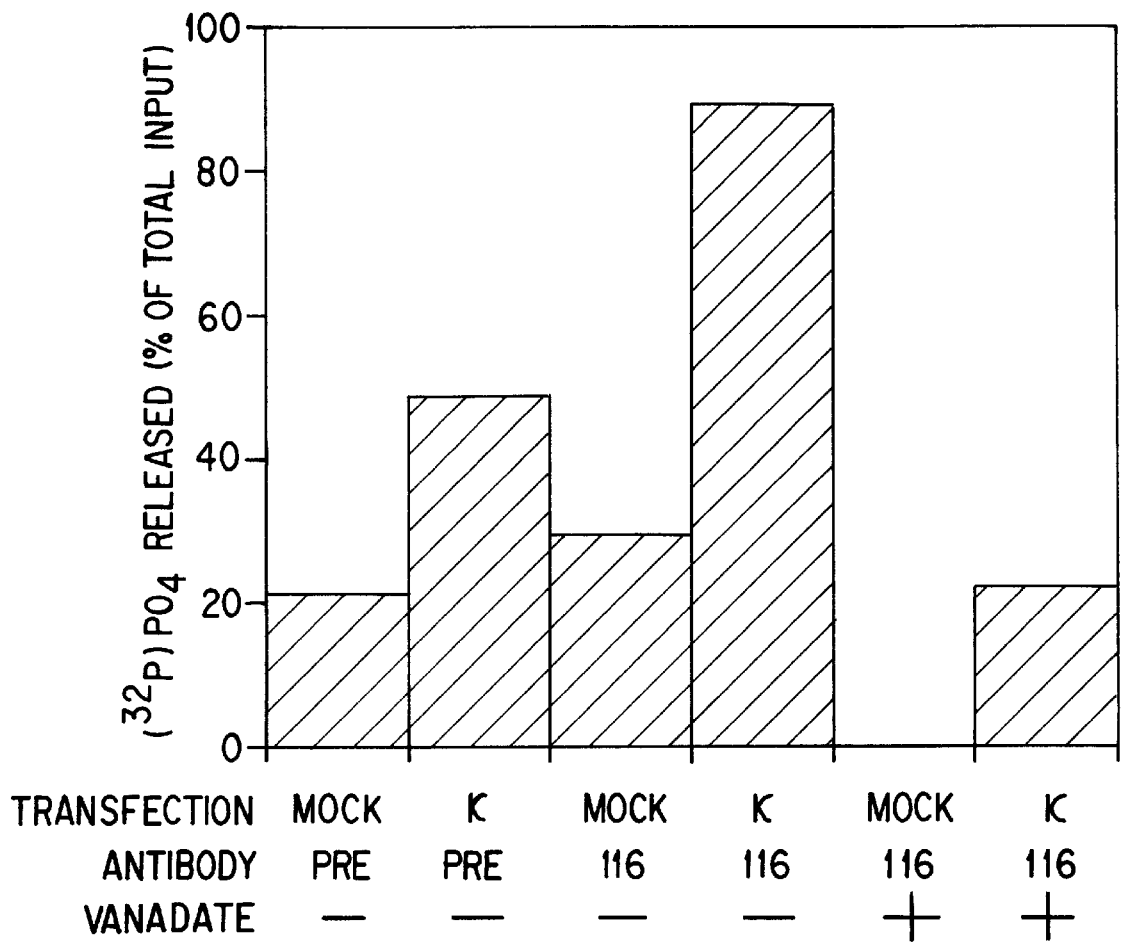

FIG. 8 shows the protein tyrosine phosphatase activity of anti-RPTPκ immunoprecipitates. The RPTPκ protein was immunoprecipitated from transiently transfected COS cells using anti-N-terminal antibody 116 or corresponding preimmune serum. The PTPase activity in the immune complexes was analyzed in the absence (−) or presence (+) of vanadate. The amount of radioactivity released as inorganic phosphate is expressed as the percentage of the total input radioactivity. A representative of several experiments is shown.

Figure 9:
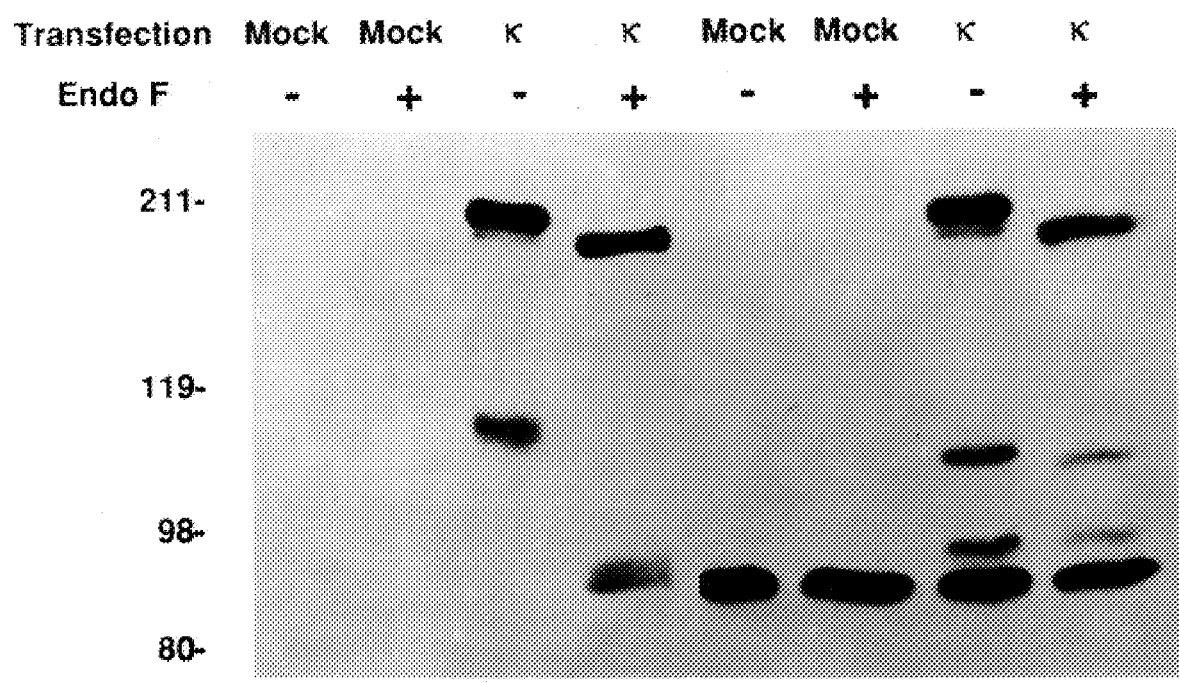

FIG. 9 shows RPTPκ immunoreactive species in COS cells, and effect of Endo F treatment on SDS-PAGE mobility. Total lysates from mock or RPTPκ transfected COS cells were treated or not with Endo F. The lysates were resolved by SDS-PAGE and immunoblotted with anti-N-terminal antibody 116 (left panel) or anti-cytoplasmic antibody 122 (right panel). The 95 kDa band in panel B also seen in mock-transfected cells is presumably due to fortuitous reactivity of antiserum 122 and not relevant to the analysis. No such protein species was detectable using an antiserum raised against the same antigen in a different rabbit.

Figure 10:
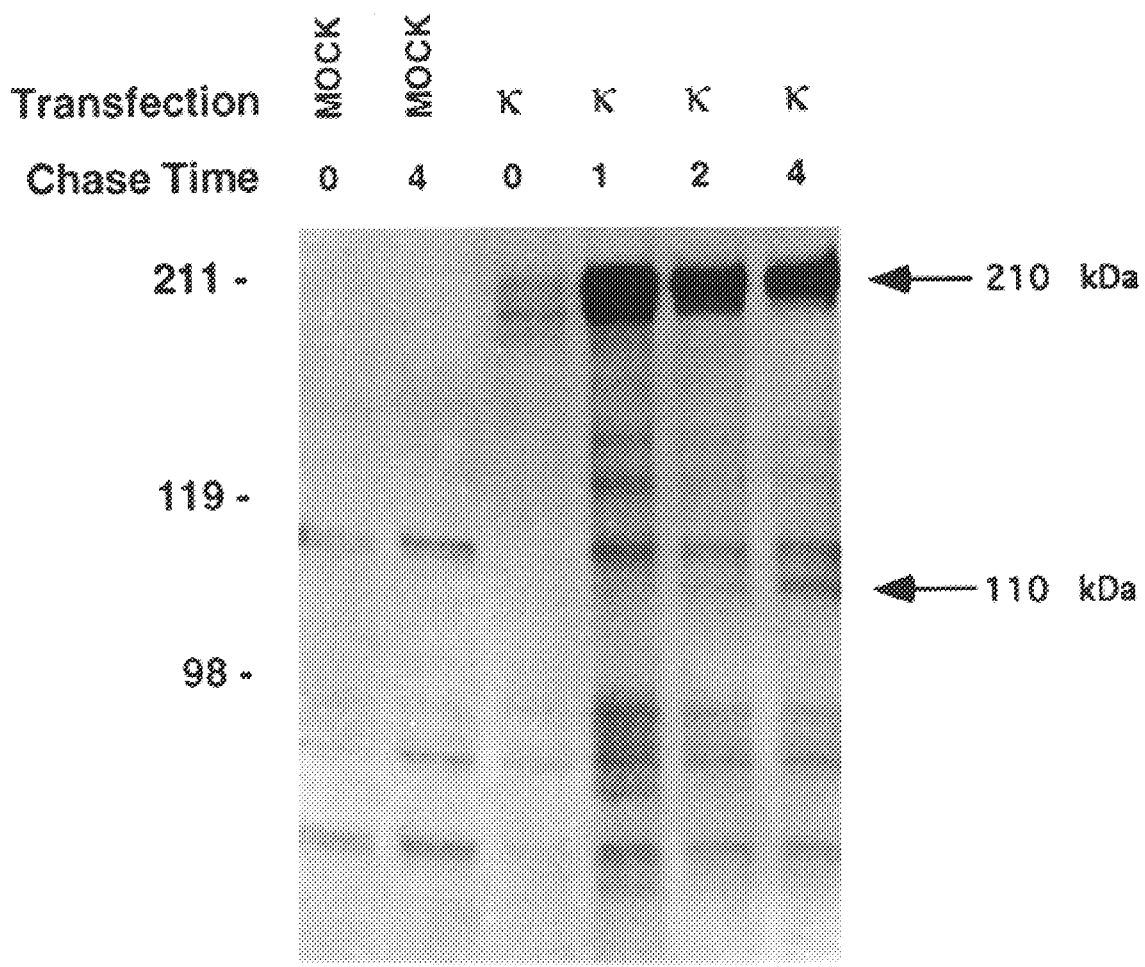

FIG. 10 shows results of a pulse-chase analysis of RPTPκ processing. Mock-transfected cells (lanes 1 and 2) and cells transfected with a wild type RPTPκ expression vector (lanes 3 to 6) were metabolically labeled with [$^{35}$S]-methionine (200 [μCi/ml] for 15 minutes ("pulse") and chased for the time-periods indicated. Immunoprecipitation was performed using antiserum 116. Arrows indicate the positions of the 210 kDa RPTPκ precursor and the 110 kDa N-terminal cleavage product.

Figure 11:
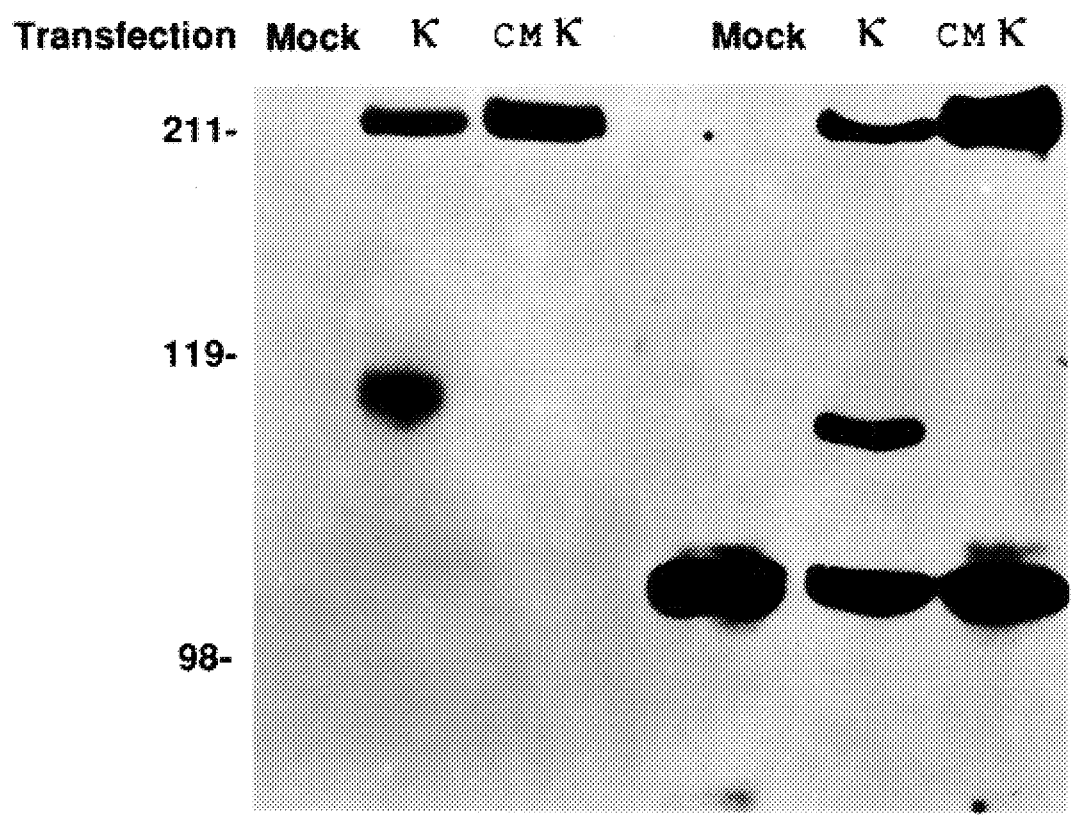

FIG. 11 shows the effect of mutagenesis of the furin cleavage motif RTKR on RPTPκ processing. Total lysates from mock-transfected COS cells, cells expressing wt RPTPκ, or RPTP(κ) carrying a mutation in the furin cleavage motif RTKR (CM κ) were resolved by SDS-PAGE. Immunoblotting was performed using anti-N-terminal antiserum 116 (left panel), or anti-cytoplasmic antiserum 122 (right panel).

Figure 12:
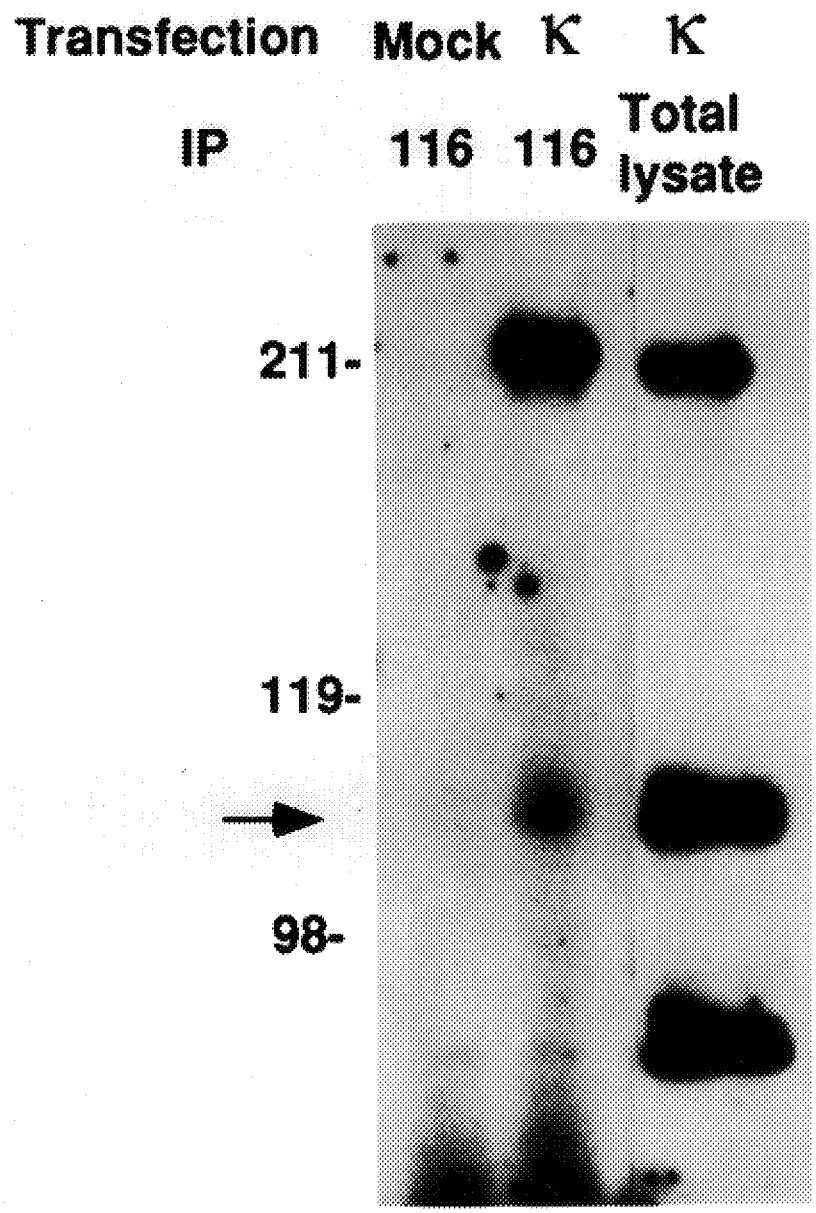

FIG. 12 shows the co-immunoprecipitation of the RPTPκ processing products. Total lysate from mock or wild type RPTPκ transfected COS cells was subjected to immunoprecipitation using anti-N-terminal antiserum 116, and the precipitate inununoblotted with anti-cytoplasmic antiserum 122. As a control, total lysate from RPTPκ transfected cells was loaded in the right lane on the immunoblot.

Figure 13A:
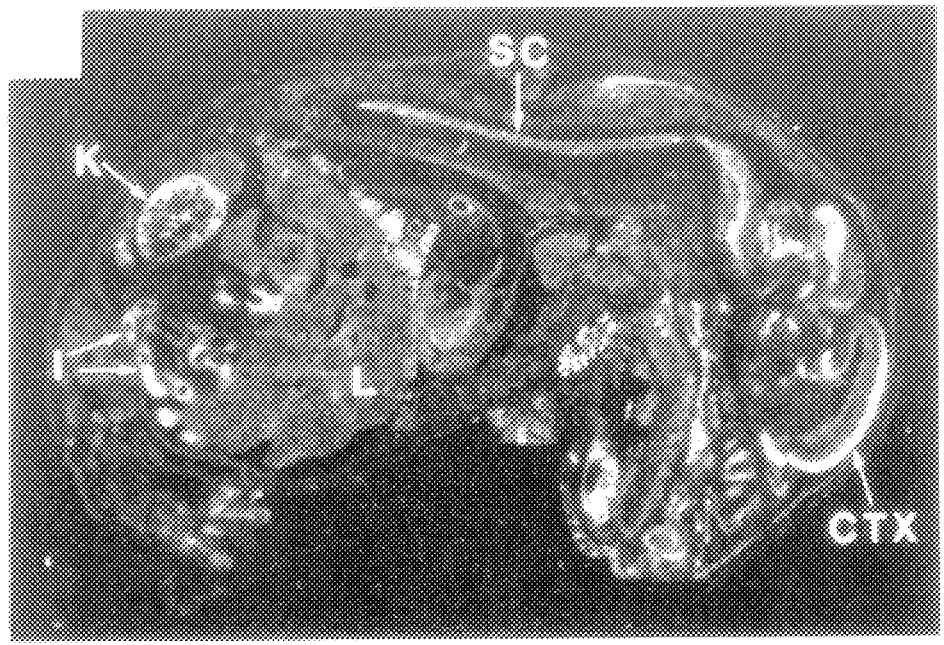
Figure 13B:
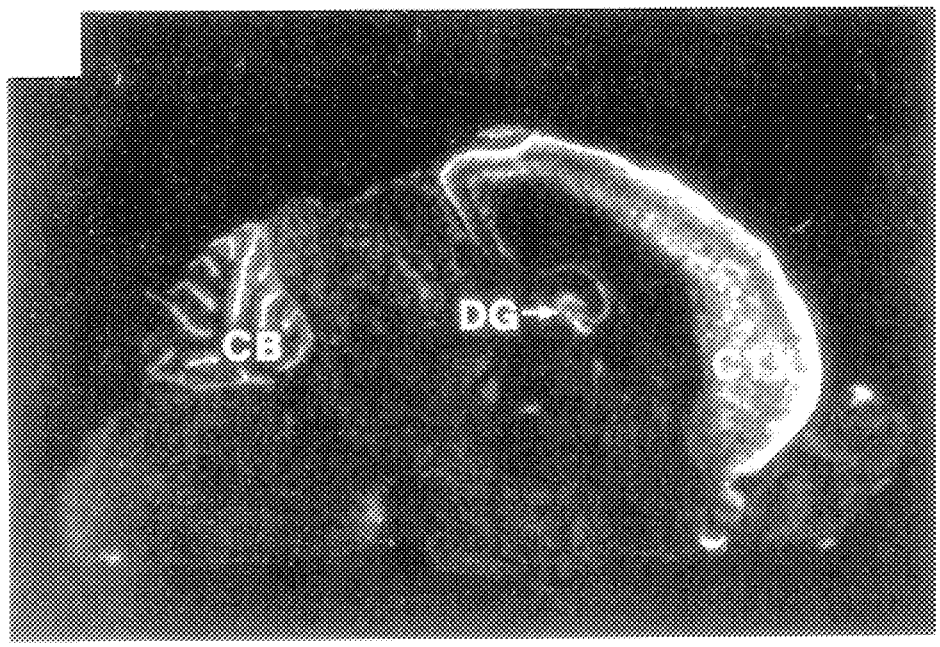

FIGS. 13A–13B is a series of micrographs showing the in situ hybridization analysis of RPTPκ expression during development and in the adult CNS. 13A panel shows localization of RPTPκ mRNA in the rat at embryonic day 18. CTX, cerebral cortex; MB, midbrain; SC, spinal cord; L, liver; K, kidney; I, intestine. 13B panel shows localization of RPTPκ mRNA in a sagittal section of rat brain at postnatal day 6. CTX, cerebral cortex; CB, cerebellum; DG, dentate gyrus. In the cerebral cortex, particularly in the occipital region, the labeling is not uniform in all the cortical cell layers. In the hippocampal formation labeling is more intense in the dentate gyrus and in CA3. In the cerebellum, the most intense labeling is seen in the external granular cell layer.

Figure 14:
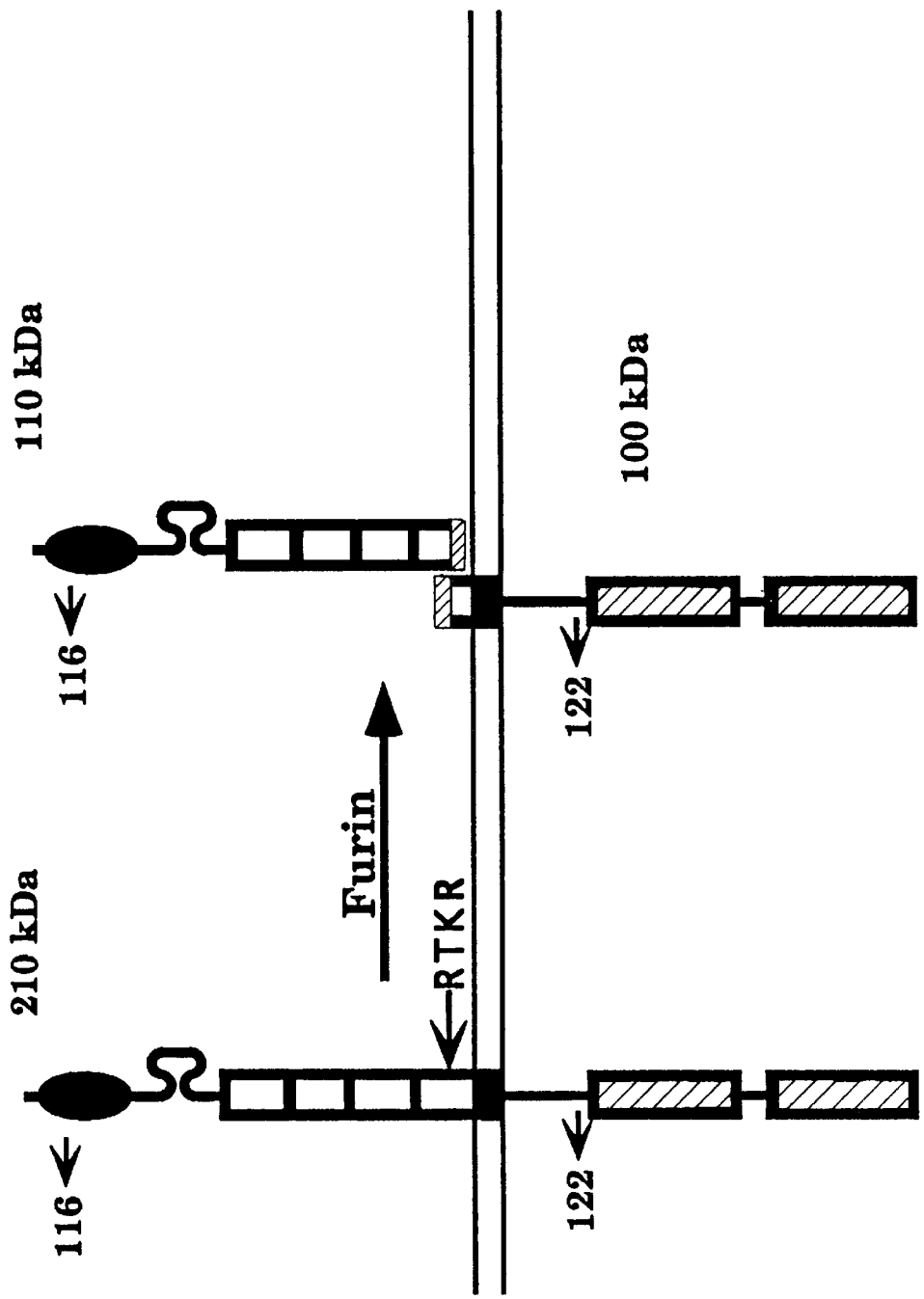

FIG. 14 is a molecular model describing the processing of the R-PTP-κ precursor protein. A furin-like endoprotease cleaves the 210 kDa precursor protein, after which both cleavage products (110 and 100 kDa) remain associated. No suggestions as to the mechanism of association are intended. The numerals 116 and 122 designate the sites of epitopes recognized by antisera described in the text.

FIGS. 15A–15E shows the nucleotide sequence of the human RPTPκ (SEQ ID NO:4), designated MCP7, and its derived amino acid sequence (SEQ ID NO:2).

FIGS. 16A–16B. A comparison of the amino acid sequence of RPTPκ [SEQ ID NO:2] to the amino acid sequence of hRPTPμ [SEQ ID NO:8]. Lack of designation of an amino acid in hRPTPμ indicates identity to the MCP7 sequence. The putative signal peptide is overlined and dotted; the MAM domain is boxed with white background; the Ig-like domain is overlined with a shaded bar; the FN-III repeats are indicated with brackets above them; the RTKR cleavage site is underlined; the transmembrane domain is indicated with asterisks; and the PTPase domains are boxed. Both PTPase domains are shown with a shaded background.

Figure 17:
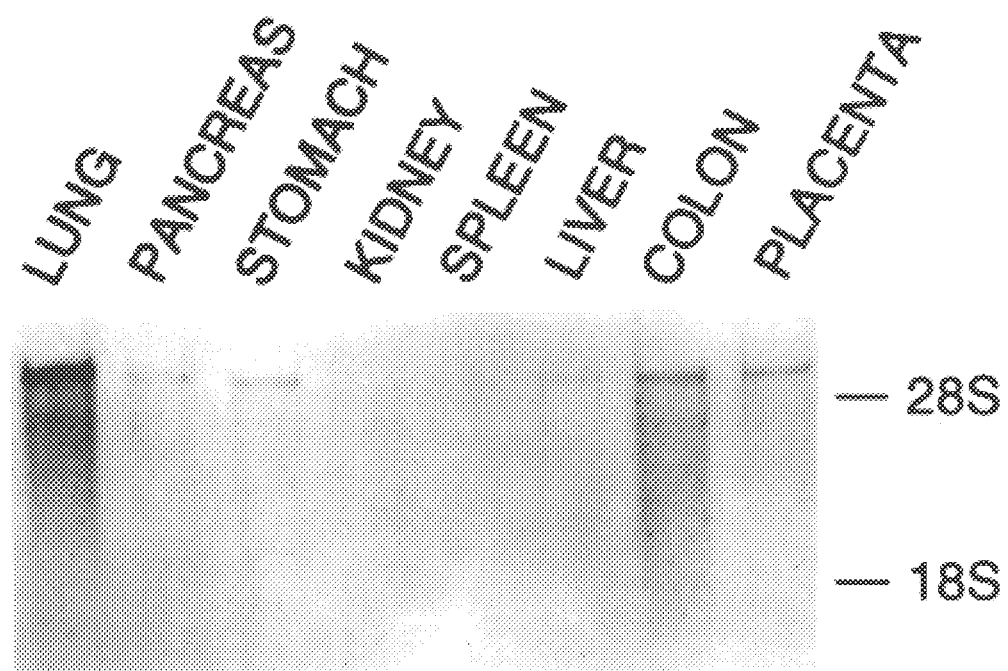

FIG. 17 shows a Northern blot analysis of MCP7 mRNA from human tissues. Poly(A)+ RNA (4 μg per lane) prepared from the indicated tissues was probed with a $^{32}$p-labeled fragment corresponding to the extracellular domain of MCP7. The blots were applied for a 5 day exposure using an intensifying screen.

Figure 18:
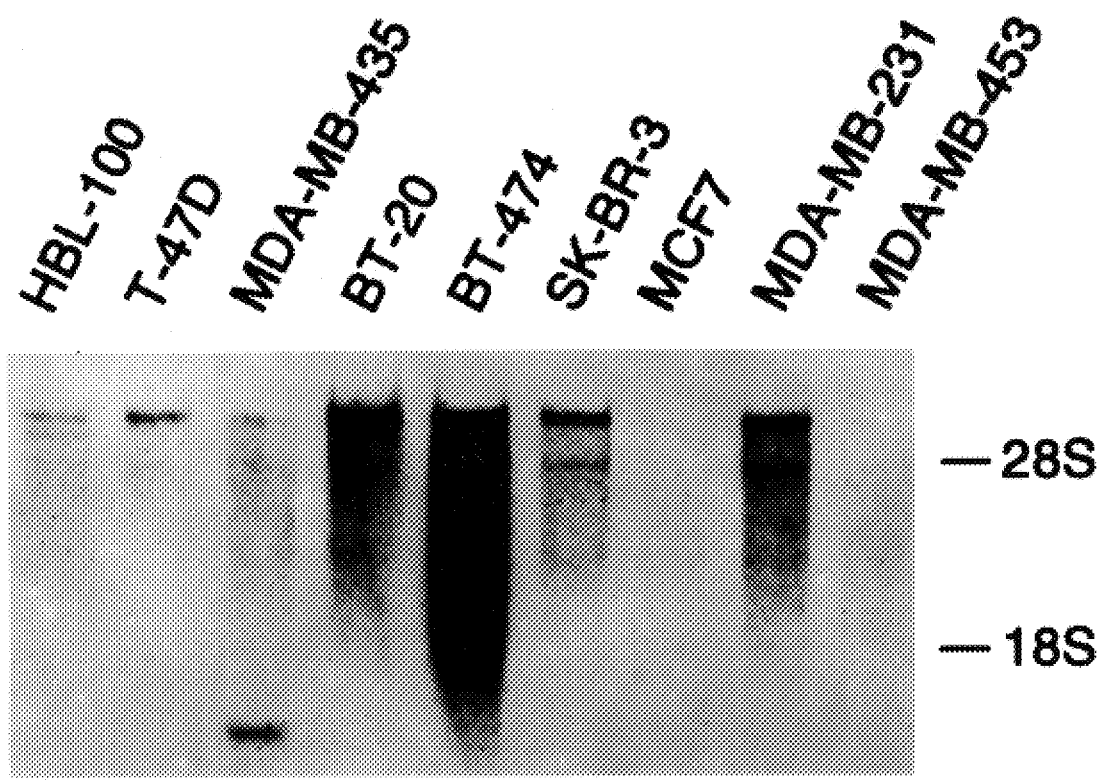

FIG. 18 shows a Northern blot analysis of MCP7 mRNA from several different human breast cancer cell lines. Poly (A)+ RNA (4 μg per lane) prepared from the indicated cell line was probed as in FIG. 17 and the blots similarly exposed.

Figure 19A:
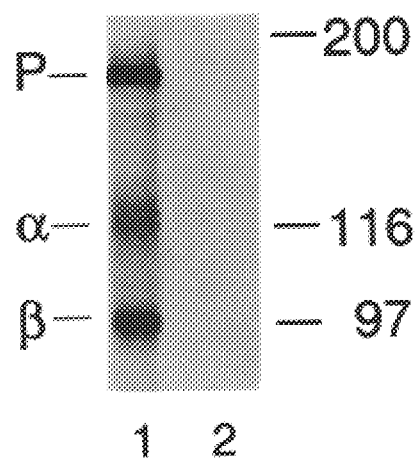
Figure 19B:
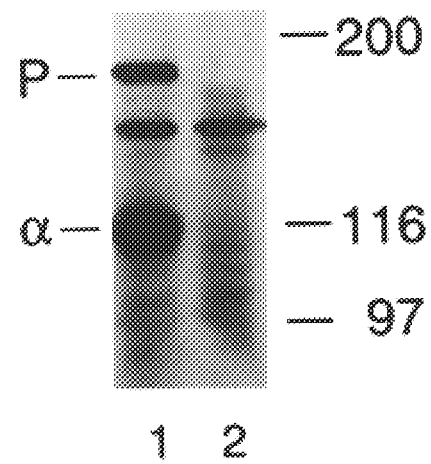

FIGS. 19A–19B shows gel patterns indicating the transient expression of MCP7 mRNA in transfected cells. Cells of the 293 line were transfected with a MCP7 expression vector (or an empty vector as a control), metabolically labeled for 24 hours with [$^{35}$S] methionine and incubated with an anti-N-terminal antiserum 116. Cells were washed, lysed and protein-antibody complexes were removed by protein-A sepharose. Left panel shows a SDS-PAGE gel of immunoprecipitates. 19B panel shows Western blots of SDS-PAGE gels of lysates of cells transfected by MCP7-CMV (lane 1) or "empty" CMV (lane 2) and immunoblotted with the anti-N-terminal antiserum 116.

Figure 20A:
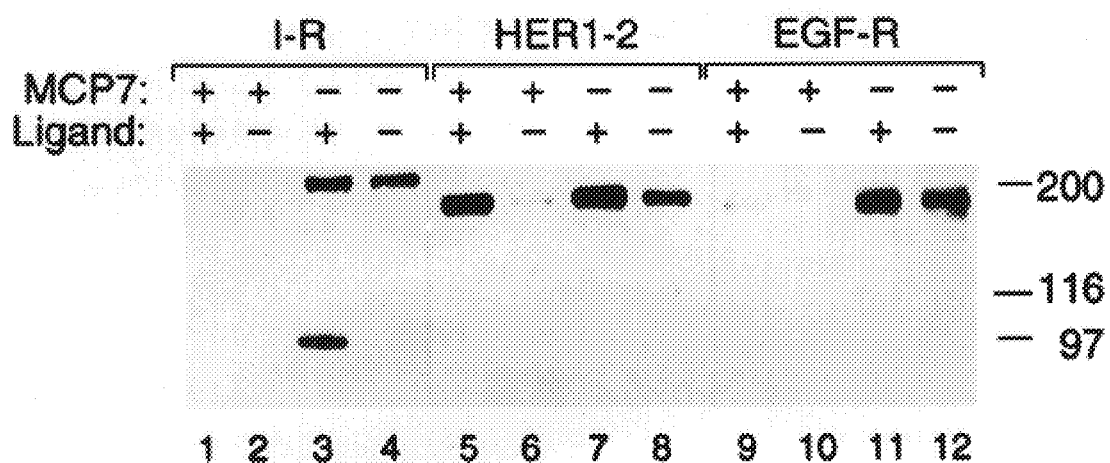
Figure 20B:
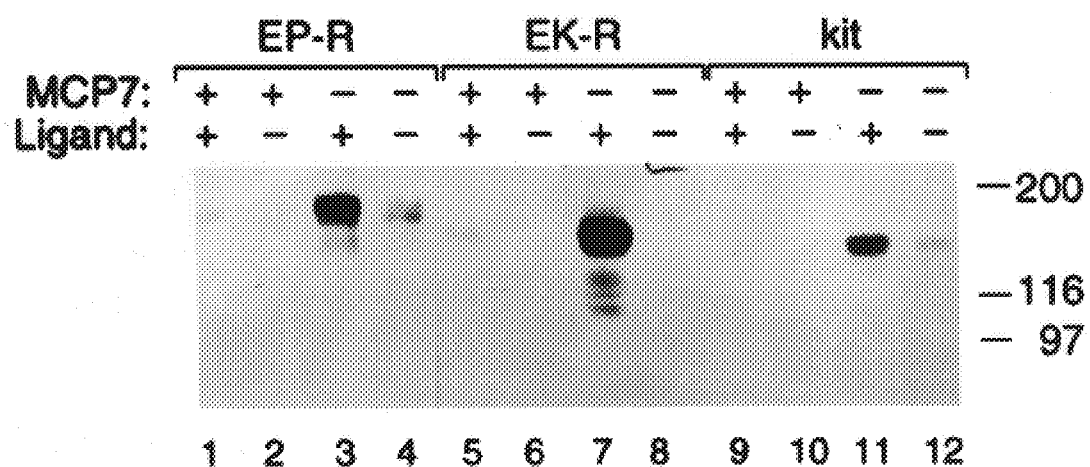

FIGS. 20A–20B shows Western blot patterns indicating co-expression of MCP7 with different RTKs. Semiconfluent 293 cells were transfected with expression plasmids encoding the indicated RTK together with either an equal amount of MCP7 expression vector or a control plasmid. After stimulation with the appropriate ligand: stem cell factor (SCF) for the p145$^{c-kit}$ RTK; epidermal growth factor for all other RTKs; insulin for I-R, cells were lysed, aliquots run on SDS-PAGE and transferred to nitrocellulose. Proteins were immunoblotted with anti-phosphotyrosine antibody 5E.2. Molecular mass markers are indicated.

Figures 21A, 21B:
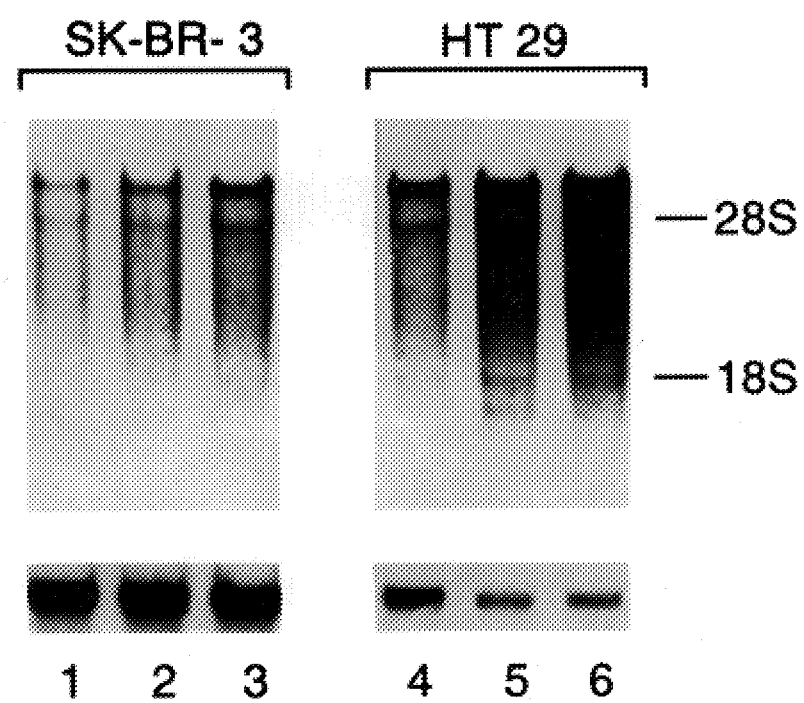

FIGS. 21A–21B shows Northern blots indicating the relationship between MCP7 mRNA levels and the state of cell confluence in SK-BR-3 cells (left panel) and HT-29 cells (right panel) in culture. Poly(A)+ RNA (4 μg per lane) was prepared from cells obtained at different levels of confluence (lanes 1 and 4: 40%; lanes 2 and 5: 70%, lane 3 and 6: 100%) and was probed with a $^{32}$P-labeled DNA probe corresponding to the extracellular domain of MCP7 (upper blots) and with a fragment coding for GAPDH (lower blots).

Figure 22A:
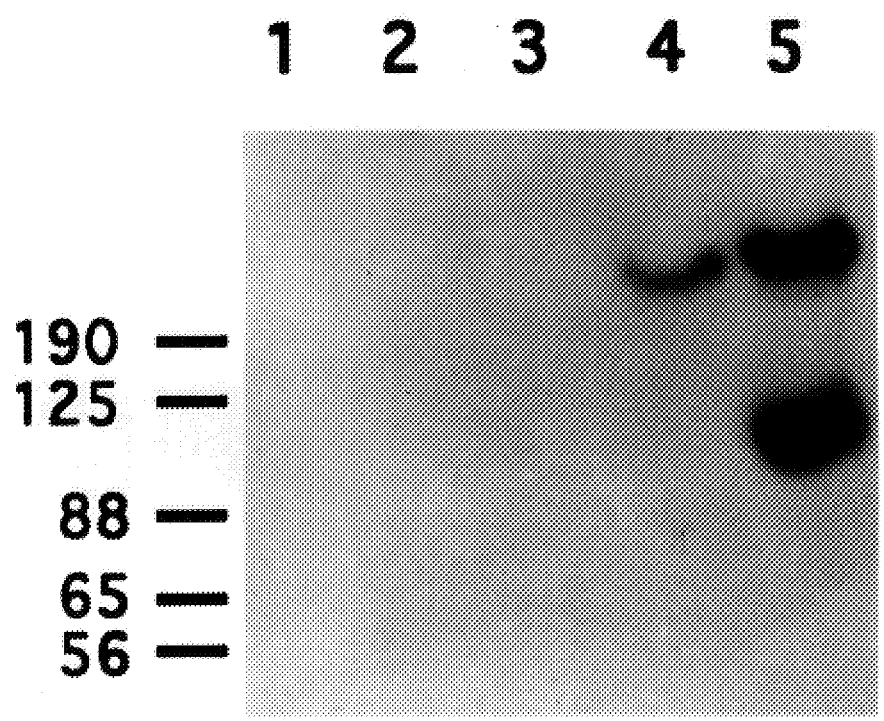

FIG. 22A. Expression of the R-PTPκ protein in transfected S2 cells. Detergent lysates were prepared from transfected cells, resolved by SDS-PAGE, and immunoblotted with an antiserum directed against the extracellular domain of the R-PTPκ protein (Y.-P. Jiang et al. Mol. Cell. Biol. 13, 2942 (1993)). Lanes: 1, R-PTPκ anti-sense transfected cells, not heat-shocked; 2, anti-sense transfected after heat-shock; 3, sense transfected cells, not heat-shocked; 4, sense-transfected cells after heat-shock; 5, lysate from COS cells transiently transfected with an R-PTPκ expression vector (Y.-P. Jiang et al. Mol. Cell. Biol. 13, 2942 (1993)). Molecular weight standards are indicated in kilodaltons.

The entire RPTPκ cDNA was introduced in both orientations as a HpaI/EcoRV fragment into the HpaI site of a derivative of the pCasper expression vector containing the hsp70 promoter, and the resulting construct co-transfected with the pPC4 plasmid (conferring α-amanitin resistance) into S2 cells using calcium phosphate precipitation. Pools of stably transfected cells were selected in the presence of 5 μg/ml α-amanitin for three weeks. Transfected cells were heat-shocked at 37° C. for 30 minutes and allowed to recover for 2 hours. Adherent cells were collected, and washed twice in BSS (Kramer, H. et al., 1991, Nature 352:207; Snow, P. et al., 1989, Cell 59:313).

Figure 22B:
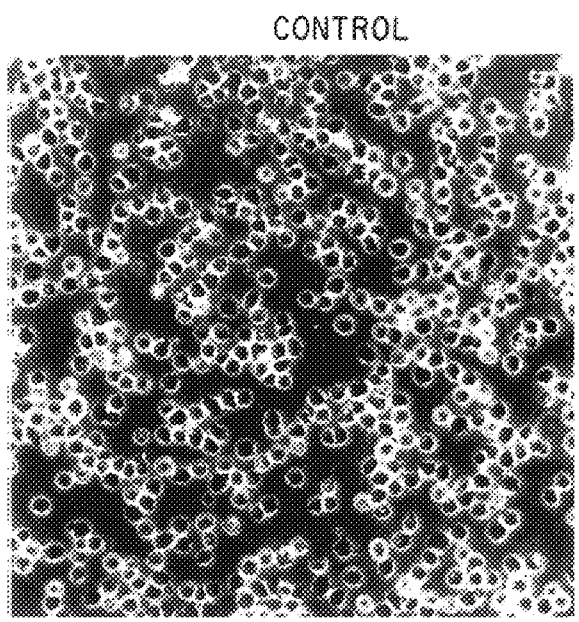
Figure 22C:
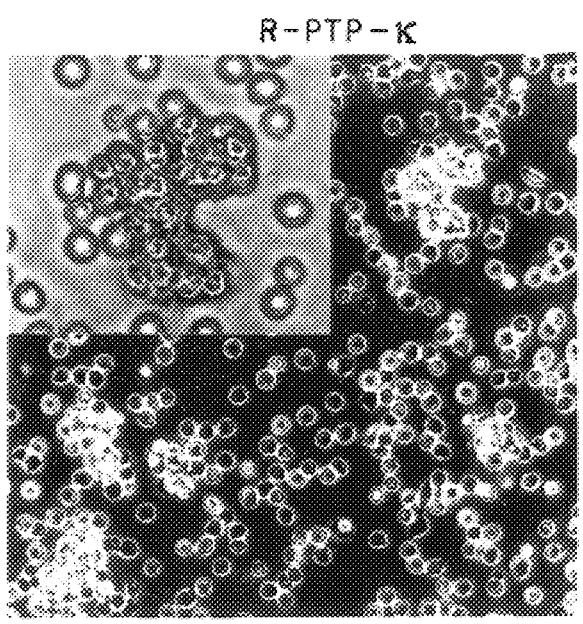

FIGS. 22B–22C. Photographs of transfected cell populations after heat-shock induction and aggregation for 2 hours. 22B panel, control (anti-sense transfected) cells; right panel, cells transfected with an expression vector carrying the R-PTPκ cDNA in the sense orientation; 22C: higher magnification of a typical aggregate.

Figure 22D:
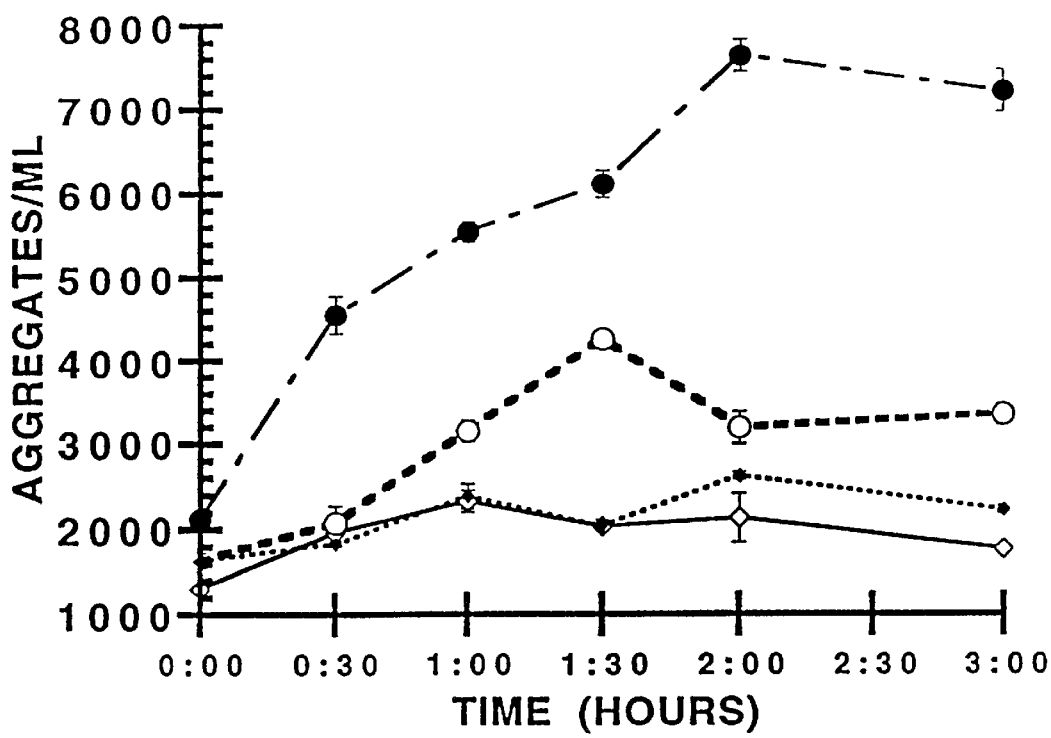

FIG. 22D. Time-course and quantitation of aggregation by Coulter-counting of above-threshold particles. Open squares: anti-sense vector transfected cells, uninduced; full squares, idem, induced; open circles, cells transfected with an expression vector containing the R-PTPκ cDNA in the sense orientation, uninduced; full circles, sense, induced. Standard errors are indicated by error bars.

Adherent, transfected cells were collected, washed twice with BSS, resuspended in BSS at a concentration of 4×10$^6$ cells/ml, and incubated in Coulter-Counter vials on a rotary shaker for 2 hours at 100 rpm at room temperature. For each time-point, 1 ml was counted using the Coulter-counter with the following settings: 1/amplification=4; threshold=10; 1/aperture current=32.

Figure 22E:
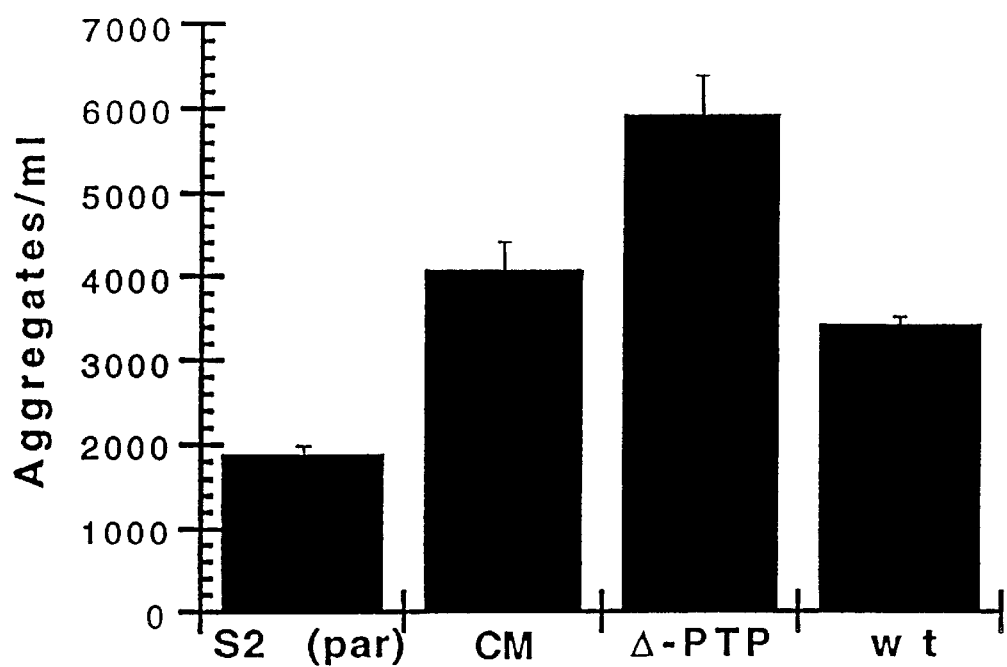

FIG. 22E. Effect of deletion of the intracellular domain of the R-PTPκ protein, and mutation of the furin cleavage site. Parental S2 cells were transiently transfected with expression vectors encoding an R-PTPκ cDNA in which the furin cleavage site had been mutated (CM) (Y.-P. Jiang et al. Mol. Cell. Biol. 13, 2942 (1993)), a cDNA encoding a catalytically inactive deletion mutant of R-PTPκ lacking most of the intracellular (PTPase) domain (Δ-PTP), or a wt R-PTPκ cDNA (wt). For the deletion mutant, a cDNA encoding a truncated, catalytically inactive form (Δκ) of RPTPκ was constructed by restriction digestion with BspEI and Klenow fill-in of the wild type cDNA. This leads to the introduction of a stop codon after amino acid residue 1083, and the generation of a protein lacking the cysteine residues essential for catalysis in the two intracellular catalytic homology domains of RPTPκ. Cells were heat-induced 72 hours after transfection, subjected to aggregating conditions for 2 hours, and above-threshold aggregates counted with a Coulter-counter. Error bars indicate standard errors. Transfected, but non heat-shock induced cells behaved as untransfected parental cells. The apparent differences in aggregation intensity between the different forms of R-PTPκ may reflect protein expression levels. The numbers provided by Coulter-counter counting actually provide an underestimation of the amount of aggregation as determined by visual inspection and counting of aggregates, since only large particles above a certain threshold size are scored by the Coulter-Counter.

Figure 23A:
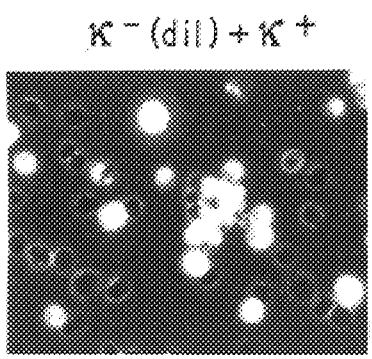
Figure 23B:
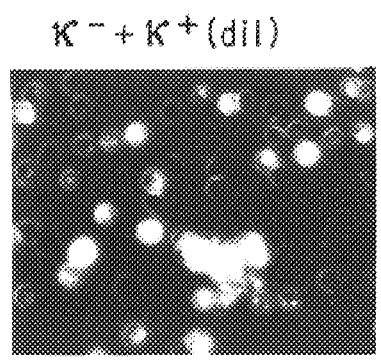
Figure 23C:
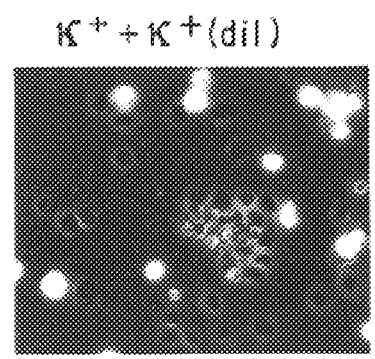
Figure 24A:
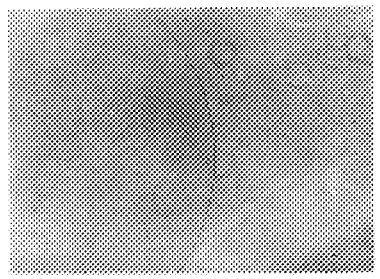
Figure 24B:
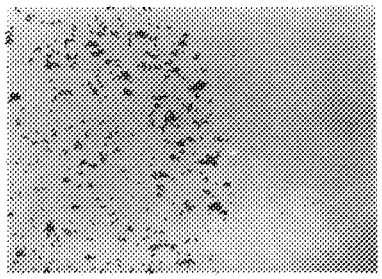
Figure 24C:
Figure 24D:
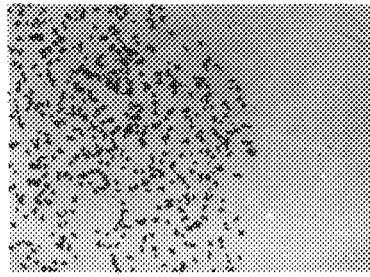

FIGS. 23A–23C. Aggregates consist solely of cells expressing the R-PTPκ protein. Two different cell populations, one of which had been labeled with the fluorescent dye diI (J. Schlessinger et al. Science 195, 307 (1977), were allowed to co-aggregate and the resulting aggregates inspected by visible and fluorescence microscopy. diI-fluorescence is white in the photographs.

FIG. 23A: a pool of R-PTPκ expressing cells was allowed to aggregate in the presence of an equal number of diI-stained R-PTPκ-negative cells.

FIG. 23B: R-PTPκ expressing cells were stained with diI and allowed to aggregate in the presence of unstained RPTPκ-negative cells.

FIG. 23C: mixture of stained and unstained R-PTPκ-positive cells.

In each case, ten aggregates were randomly localized under visible light only. Subsequent inspection under U.V. light consistently showed the staining pattern exemplified in the photographs. diI dye (Molecular Probes, Inc.) was added to the growth medium at a concentration of 3.2 μM during heat shock, and washed away prior to recovery and assay. $2 \times 10^6$ cells of each population were mixed and allowed to co-aggregate in a total volume of 1 ml.

FIGS. 24A–24D. Adhesion of R-PTPκ transfected cells to a surface coated with recombinant purified R-PTPκ extracellular domain protein. R-PTPκ-negative, 1, or positive, 2, S2 cells, or R-PTPκ-negative, 3, and positive, 4, L6 cells were incubated with a surface partially coated with the K2AP protein (circle), and the adherent cells fixed and stained. Amino acids 1–639 of the RPTPκ proprotein were fused in-frame with human placental alkaline phosphatase in the vector pBacblue III (Invitrogen) by a series of appropriate cloning steps. Recombinant virus was generated and used to infect High-Five cells for production of the K2AP fusion protein using standard procedures. A secreted alkaline phosphatase (AP) control protein was generated in L6 myoblast cells by stable transfection with a modified version of the AP-TAG vector encoding a fusion protein of AP with a signal peptide. Both proteins were affinity purified by elution from an anti-alkaline phosphatase monoclonal antibody (Medix Biotech) column using 100 mM diethanolamine pH 11.5, or 50% ethylene glycol, dialyzed against PBS, and stored at 4° C. The K2AP and AP proteins were approximately 90% and 50% pure, resp. as determined by silver staining. To generate a mammalian cell line expressing the RPTPκ protein, an MJ 30-based RPTPκ expression vector was co-transfected with pSVneo into L6 cells, and individual clones surviving G418 selection screened for expression using immunoblotting. This procedure did not detect endogenous RPTPκ protein in the parental L6 cells. The expressed protein underwent appropriate furin cleavage as described (Jiang, Y.-P. et al., 1993, Mol. Cell. Biol. 13:2942).

For adhesion assays, 4 μl aliquots of protein samples (20 μg/ml) were spotted on 35 mm bacteriological Petri dishes and incubated at room temperature for 30 minutes. The solutions were removed by aspiration, and the surface of the entire plate blocked with 1% heat-inactivated BSA for 60–90 minutes. The plates were incubated with a suspension of S2 cells ($4 \times 10^6$/ml) in BSS with shaking (50 rpm) for one hour at room temperature, or with L6 cells in S-MEM ($2 \times 10^6$/ml) without shaking, at 37° C., washed three times with PBS, fixed and stained.

5. DETAILED DESCRIPTION OF THE INVENTION

Through the use of recombinant DNA methods, the present inventors have identified novel mammalian receptor-type (transmembrane) protein tyrosine phosphatases (PTPase; EC 3.1.3.48). In view of its receptor-like structure, and the likelihood that it is part of a family, the inventors have termed this protein, RPTPκ (receptor protein tyrosine phosphatase-κ). The family is designated herein as the "RPTPs." Human RPTPκ has 1444 amino acids (SEQ. ID NO:2).

Human RPTPκ (also designated MCP7) has an extracellular domain composed of one "MAM" domain, which is a sequence motif spanning about 170 amino acid residues, which was recently established by comparison of several functionally diverse receptors (including RPTPμ and the A5 protein) and is thought to play a role in cell adhesion (Beckmann & Bork, 1993, TIBS 18:40–41). The extracellular domain further includes one Ig-like, and four FN-type III-like segments. It therefore shares structural features with some cell adhesion molecules, permitting the classification of RPTPκ into the type II PTPase class.

The cDNA cloning of human RPTPκ and the complete DNA and amino acid sequences of human RPTPκ and its murine homologue are described herein. Northern analysis has been used to identify the natural expression of the protein in various cells and tissues. A partial cDNA clone of the catalytic domain of RPTPκ/HPTPκ has been previously described (commonly assigned U.S. patent application Ser. No. 07/654,188, from which the present application claims priority; Kaplan et al., Proc. Natl. Acad. Sci. 87:7000–7004 (1990); Krueger et al., EMBO J. 9:3241–3252 (1990)).

RPTPκ has been shown to be expressed in anatomically distinct regions of rat brain and its expression has been found to be developmentally regulated.

Remarkably, in addition to being composed of intracellular domains having enzymatic activity, the receptor family to which RPTPs belong includes transmembrane proteins having and N-terminal extracellular domains, analogous to the tyrosine kinase enzyme family (Tonks, N. K. et al. (1988) Biochemistry 27:8695–8701; Charbonneau, H. et al. (1988) Proc. Natl. Acad. Sci. USA 85:7182–7186; Streuli, M. et al. (1988) J. Exp. Med. 168:1523–2530; Streuli, M. et al. (1989) Proc. Natl. Acad. Sci. USA 86:8698–8702). The present inventors have therefore concluded that ligands in the extracellular environment can control the activity of this membrane-associated subclass of PTPases.

Further, results presented in the current invention demonstrate that Type II RPTPs undergo homophilic binding, i.e., Type II RPTP receptor molecules have the ability to bind to each other. Homophilic binding, as defined here, may include intercellular binding and/or binding of at least two Type II RPTP receptor proteins present on the surface of the same cell. In addition, homophilic binding may include not only binding of identical Type II RPTP molecules to each other, for example binding of at least two RPTPκ molecules to each other, but may also include the binding of any two Type II RPTP molecules to each other, such as, for example, the binding of RPTPκ to another Type II RPTP molecule. As demonstrated in the Working Example presented in Section 15, below, RPTPκ undergoes intercellular homophilic binding to other RPTPκ molecules. This result represents the first example of such a homophilic binding mechanism observed within the RPTP family of molecules, and provides a link between cell—cell contact and cellular signaling events involving tyrosine phosphorylation.

RPTPκ is useful in methods for screening drugs and other agents which are capable of activating or inhibiting the PTPase enzymatic activity, and thereby affecting major pathways of cellular metabolism. By attaching an intact RPTPκ, or the ligand-binding portion thereof, to a solid phase matrix, an affinity probe is created which can be used to screen biological products or chemical agents for their capacity to interact with the receptor on the basis of their binding activity. Bound material can then be eluted from the affinity probe in purified form.

RPTPκ is also useful in methods for screening drugs and other agents which are capable in inhibiting Type II RPTP homophilic binding, and thus affecting major processes involving, but not limited to, cell—cell and/or cell-ECM (extracellular matrix) interactions. By attaching an intact Type II RPTP such as RPTPκ, or an extracellular domain thereof, to a solid matrix, drugs or other agents may be screened for their ability to bind the RPTP. Those agents which bind the RPTP with specificity may be eluted off the solid phase matrix in purified form and further tested for their ability to inhibit RPTP homophilic binding. Note that it is intended to be within the scope of this invention that the inhibition of RPTP homophilic binding described herein refers to not only the binding of at least two identical Type II RPTP molecules, such as at least two RPTPκ molecules to each other, but also to binding of any Type II RPTP class of molecules to each other, such as, for example, the binding of RPTPκ to another Type II RPTP molecule. Potential agents which may inhibit such Type II RPTP binding may include, but are not limited to, soluble portions of Type II RPTP extracellular domains, antibodies directed against Type II RPTP extracellular domain epitopes, or small synthetic molecules. RPTP extracellular domains may include all or any inhibitory portion of the MAM, Ig, and/or fibronectin Type III (FN-III) domains, as well as peptides which include the HAV, and/or the RXR/LR consensus sequences, as described below. Any of the inhibitory compounds which inhibit homophilic RPTP binding may but are not required to modulate the phosphatase activity of the RPTP molecules whose binding capability is affected.

Further, the ability of a compound to inhibit Type II RPTPκ homophilic binding may be tested in a variety of ways. RPTPκ will be used as an example, but it should be kept clear that such techniques may be used for any Type II RPTP molecule. RPTPκ, or an extracellular domain thereof, may first be immobilized by attachment to a solid matrix, using techniques well known to those of ordinary skill in the art. Such a solid matrix may include but is not limited to a petri dish, microtiter well, or a glass, plastic or agarose bead. Second, RPTPκ, either in a purified protein form or, alternatively, present in a cell membrane preparation or present on the surface of an intact cell, may be incubated in the presence of the solid matrix together with a compound of interest. The ability of the compound to inhibit RPTRK homophilic binding to the solid matrix may then be assayed by determining if RPTPκ molecules bind the immobilized molecules. Such a determination may be accomplished using a variety of techniques well known to those of ordinary skill in the art and include, but are not limited to the labelling of the RPTPκ present in purified form, in a cell membrane preparation, or in an intact cell. Alternatively, a compound of interest may be tested by incubating RPTPκ-expressing cells in the presence of the compound of interest and subsequently assaying the ability of the cells to undergo aggregation. Aggregation assays may include, but are not limited to directly counting aggregates using the aid of a microscope, and/or determining super-threshold particles with a coulter-counter.

Methods for coupling proteins and peptides to a solid phase matrix or carrier, the solid phase matrix materials useful in these methods, and means for elution, are well known to those of skill in the art.

The RPTPκ protein, or derivatives thereof having enzymatic activity, can be used for testing agents or compounds capable of enhancing or inhibiting the phosphatase activity. The ability of a compound under test to modify phosphatase activity can be tested in an in vitro system wherein the test compound is added to purified RPTPκ protein, or an enzymatically active derivative thereof, and the effects on enzyme activity measured using standard enzymological procedures well known to those of skill in the art.

Alternatively, the action of a compound on RPTPκ enzymatic activity can be measured in a whole cell preparation using live or fixed cells, or a membrane fraction derived from live or fixed cells. This method is useful for screening compounds acting via the extracellular receptor portion of the protein, as well as compounds acting directly on the enzymatic portion of the protein. A test compound is incubated with cells, or with a membrane preparation derived therefrom, which express high amounts of RPTPκ, such as transfected COS or NIH-3T3 cells. The amount of cellular phosphotyrosine is then measured, using methods well-known in the art (Honegger, A. M. et al., *Cell* 51:199–209 (1987); Margolis, B. et al., *Cell* 57:1101–1107 (1989)). The results are compared to results obtained in the absence of the test compound, or in the absence or presence of a known activator of RPTPκ enzymatic activity. In such studies, the action of the test compound in the presence of an activator of tyrosine kinase can also be measured. A compound which stimulates RPTPκ enzymatic activity will result in a net decrease in the amount of phosphotyrosine, whereas a compound which inhibits RPTPκ enzymatic activity will result in a net increase in the amount of phosphotyrosine. Compounds which inhibit homophilic Type II RPTP binding may also modulate the enzymatic activity of the RPTP molecules they affect, either by increasing or decreasing the RPTPs' phosphatase activity.

In the case of growth factor receptors which are tyrosine kinases, such as the receptors for epidermal growth factor (EGF) and for platelet-derived growth factor (PDGF), tyrosine phosphorylation is linked to cell growth and to oncogenic transformation. Activation of a PTPase, leading to dephosphorylation, would serve as a counterregulatory mechanism to prevent or inhibit growth, and might serve as an endogenous regulatory mechanism against cancer. Thus, mutation or dysregulation of this receptor/enzyme system may promote susceptibility to cancer.

Inhibitory compounds which are found that are capable of inhibiting Type II RPTP homophilic binding may be used to modulate a variety of cellular processes including, but not limited to those involving cell—cell and/or cell-ECM interactions. Such processes include, but are not limited to normal cellular functions such as differentiation and cell cycle control; normal cellular behaviors including, but not limited to motility, contact inhibition, cell adhesion, and signal transduction; and abnormal or potentially deleterious processes such as cellular transformation to a cancerous state.

Inhibitory compounds which inhibit Type II RPTP homophilic binding may be used to modulate such processes in mammals by administration of an effective concentration of the inhibitory compound to a mammal, using techniques well known to those of ordinary skill in the art. Inhibitory compounds may include, but are not limited to, compounds comprising soluble RPTP Type II extracellular domains, for example, soluble RPTPκ extracellular domains.

Depending on the conditions being treated, agents may be formulated and administered systemically or locally. Techniques for formulation and administration may be found in "Remington's Pharmaceutical Sciences," Mack Publishing Co., Easton, Pa., latest edition. Suitable routes may include oral, rectal, transmucosal, or intestinal administration; parenteral delivery, including intramuscular, subcutaneous, intramedullary injections, as well as intrathecal, direct intraventicular, intravenous, intraperitoneal, intranasal, or intraocular injections, just to name a few. For injection, the agents of the invention may be formulated in aqueous solutions, preferably in physiologically compatible buffers such as Hank's solution, Ringer's solution, or physiological saline bffer. For such transmucosal administration, penetrants appropriate to the barrier to be permeated are used in the formulation. Such penetrants are generally known in the art.

The insulin receptor is also a tyrosine kinase, and phosphorylation of tyrosine in cells bearing insulin receptors would be associated with normal physiological function. In contrast to the case of cell growth and cancer, activation of an RPTP would counteract insulin effects. Subnormal RPTP levels or enzymatic activity would act to remove a normal counterregulatory mechanisms. Perhaps more important, though, over-activity, or inappropriate activation, of an RPTP, such as RPTPκ, would be expected to partially or totally inhibit the action of insulin on cells, leading to diabetes (of an insulin-resistant variety). Thus, susceptibility to diabetes may be associated with RPTPκ dysregulation.

Therefore, the methods of the present invention for identifying normal or mutant genes encoding RPTPκ, or for measuring the amount or activity of RPTPκ associated with a cell or tissue, can serve as methods for identifying susceptibility to cancer, diabetes, or other diseases associated with alterations in cellular phosphotyrosine metabolism.

The present invention provides methods for evaluating the presence of, and the level of, normal or mutant RPTPκ in a cell or in a subject. Absence, or more typically, low expression of the RPTPκ, or presence of a mutant RPTPκ, in an individual may serve as an important predictor of susceptibility to oncogenic transformation and the development of cancer. Alternatively, over-expression of RPTPκ, possibly due to a mutant receptor/enzyme system insensitive to negative regulation, or due to overabundance of a stimulatory ligand in the body, may serve as an important predictor of susceptibility to diabetes.

An oligonucleotide probe corresponding to a DNA sequences encoding a part of RPTPκ (see below) is used to test cells from a subject for the presence of DNA or RNA sequences encoding the RPTPκ. A preferred probe would be one directed to the nucleic acid sequence encoding at least 4 amino acid residues, and preferably at least 5 amino acid residues, of the RPTPκ. Qualitative or quantitative assays can be performed using such probes. For example, Northern analysis (see Section 7, below) is used to measure expression of an RPTPκ mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al., *MOLECULAR CLONING: A LABORATORY MANUAL*, Second Edition, Cold Spring Harbor Press, Cold Spring Harbor, N.Y. (1989), which references are herein incorporated by reference).

An in vitro enzymatic method which is capable of increasing the concentration of such desired nucleic acid molecules is called the "polymerase chain reaction or "PCR" (Mullis, K. et al., *Cold Spring Harbor Symp. Quant. Biol.* 51:263–273 (1986); Erlich, H. et al., EP 50424, EP 84796, EP 258017, EP 237362; Mullis, K., EP 201184; Mullis, K. et al., U.S. Pat. No. 4,683,202; Erlich, H., U.S. Pat. No. 4,582,788; and Saiki, R. et al., U.S. Pat. No. 4,683,194).

The PCR provides a method for selectively increasing the concentration of a particular nucleic acid sequence even when that sequence has not been previously purified and is present only in a single copy in a particular sample. The method can be used to amplify either single- or double-stranded DNA. The method uses two oligonucleotide probes to serve as primers for the template-dependent, polymerase mediated replication of a desired nucleic acid molecule.

The precise nature of the two oligonucleotide probes of the PCR method is critical to the success of the method. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes are selected such that they contain sequences identical to, or complementary to, sequences which flank the particular nucleic acid sequence whose amplification is desired. More specifically, the oligonucleotide sequence of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

PCR reaction conditions are cycled between (a) those conducive to hybridization and nucleic acid polymerization, and (b) those which result in the denaturation of duplex molecules. In the first step of the reaction, the nucleic acids of the sample are transiently heated, and then cooled, in order to denature any double-stranded molecules. The "first" and "second" probes are then added to the sample at a concentration which greatly exceeds that of the desired nucleic acid molecule. Upon incubation under conditions conducive to hybridization and polymerization, the "first" probe will hybridize to the sample nucleic acid molecule at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. For reviews of the PCR, see: Mullis, K. B., *Cold Spring Harbor Symp. Quant. Biol.* 51:263–273 (1986); Saiki, R. K. et al. *BioTechnology* 3:1008–1012 (1985); Mullis, K. B. et al. *Meth. Enzymol.* 155:335–350 (1987).

In one embodiment, the present invention is directed to a naturally occurring mammalian RPTPκ. In another embodiment, the present invention is directed to a recombinant mammalian RPTPκ. The preferred mammalian RPTPκ of the present invention is of human origin. The invention provides the naturally occurring molecule substantially free of other proteins with which it is natively associated. "Substantially free of other proteins or glycoproteins" indicates that the protein has been purified away from at least 90 per cent (on a weight basis), and from even at least 99 per cent if desired, of other proteins and glycoproteins with which it is natively associated, and is therefore substantially free of them. That can be achieved by subjecting the cells, tissue or fluid containing the RPTPκ to standard protein purification techniques such as an immunoabsorbent column bearing an antibody specific for the protein. Other forms of affinity purification utilize solid-phase substrates which bind the RPTP's enzymatic domain, or a ligand that will bind to the receptor domain. Alternatively, the purification can be achieved by a combination of standard methods, such as ammonium sulfate precipitation, molecular sieve chromatography, and ion exchange chromatography.

It will be understood that the RPTPκ of the present invention can be biochemically purified from a variety of cell or tissue sources. For preparation of naturally occurring RPTPκ, tissues such as mammalian brain, especially of human origin, are preferred.

Alternatively, because the gene for the RPTPκ can be isolated or synthesized, the polypeptide can be synthesized substantially free of other mammalian proteins or glycoproteins in a prokaryotic organism or in a non-mammalian eukaryotic organism, if desired. As intended by the present invention, a recombinant RPTPκ molecule produced in mammalian cells, such as transfected COS, NIH-3T3, or CHO cells, for example, is a protein with the naturally occurring amino acid sequence or is a functional derivative thereof. Where a naturally occurring protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support.

The present invention provides any of a number of "functional derivatives" of the RPTPκ. By "functional derivative" is meant a "fragment," "variant," "analog," or "chemical derivative" of the RPTPκ, which terms are defined below. A functional derivative retains at least a portion of the function of the RPTPκ, such as (a) binding to a specific antibody, (b) phosphatase enzymatic activity, or (c) binding of the extracellular "receptor" domain to a ligand, which permits its utility in accordance with the present invention.

A "fragment" of the RPTPκ refers to any subset of the molecule, that is, a shorter peptide.

A "variant" of the RPTPκ refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication EP 75444).

At the genetic level, these variants ordinarily are prepared by site-directed mutagenesis (as exemplified by Adelman et al., DNA 2:183 (1983)) of nucleotides in the DNA encoding the protein or peptide molecule, thereby producing DNA encoding the variant, and thereafter expressing the DNA in recombinant cell culture. The variants typically exhibit the same qualitative biological activity as the nonvariant protein or peptide.

An "analog" of the RPTPκ refers to a non-natural molecule substantially similar to either the entire molecule or a fragment thereof.

A "chemical derivative" of the RPTPκ contains additional chemical moieties not normally a part of the peptide. Covalent modifications of the RPTPκ protein or of a peptide derived therefrom, are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate, pH 5.5–7.0, because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues may be deamidated to the corresponding glutamyl and aspartyl residues, under mildly acidic conditions. Either form of these residues falls within the scope of this invention.

Derivatization with bifunctional agents is useful for cross-linking the protein or peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691, 016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the X-amino groups of lysine, arginine, and histidine side chains (T. E. Creighton, *PROTEINS: STRUCTURE AND MOLECULE PROPERTIES*, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *REMINGTON'S PHARMACEUTICAL SCIENCES*, 16th ed., Mack Publishing Co., Easton, Pa. (1980).

This invention is also directed to an antibody specific for an epitope of RPTPκ, preferably, of human RPTPκ, and the use of such an antibody to detect the presence of, or measure the quantity or concentration of, the RPTPκ in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen, preferably the RPTPκ protein or glycoprotein, a peptide derived therefrom or an epitope thereof.

Monoclonal antibodies are a substantially homogeneous population of antibodies to specific antigens. MAbs may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having variable region derived from a murine mAb and a human immunoglobulin constant region. Chimeric antibodies and methods for their production are well-known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Neuberger et al., *Nature* 314:268–270 (1985); Taniguchi et al., European Patent Publication EP171496 (Feb. 19, 1985); Morrison et al., European Patent Publication EP 173494 (Mar. 5, 1986); Neuberger et al., PCT Publication WO 86/01533 (Mar. 13, 1986); Kudo et al., European Patent Publication EP 184187 (Jun. 11, 1986); Sahagan et al., *J. Immunol.* 137:1066–1074 (1986); Robinson et al., International Patent Publication #PCT/US86/02269 (7 May 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988)). These references are hereby incorporated by reference.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other hybrid clones expressing antibodies of identical specificity.

Accordingly, mAbs generated against RPTPκ may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an RPTPκ epitope. The anti-Id mAbs thus have their own idiotypic epitopes, or "idiotopes" structurally similar to the epitope being evaluated, such as an epitope of RPTPκ.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of RPTPκ according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics. An "antigen" is a molecule or a portion of a molecule capable of being bound by an antibody which is additionally capable of inducing an animal to produce antibody capable of binding to an epitope of that antigen. An antigen may have one, or more than one epitope.

An antibody is said to be specific for an antigen because it reacts in a highly selective manner, with that antigen and not with the multitude of other antigens which are structurally distinct.

The antibodies or antibody fragments of the present invention may be used to quantitatively or qualitatively detect the presence of cells which express the RPTPκ protein. This can be accomplished by immunofluorescence techniques employing a fluorescently labeled antibody (see below) coupled with light microscopic, flow cytometric, or fluorimetric detection. For such methods, the antibody is preferably specific for an extracellular epitope of RPTPκ.

The antibodies (or fragments thereof) useful in the present invention may be employed histologically, as in immunofluorescence or immunoelectron microscopy, for in situ detection of RPTPκ. In situ detection may be accomplished by removing a histological specimen from a subject, and providing a labeled antibody or antibody fragment of the present invention to such a specimen, preferably by applying or overlaying the antibody over the specimen. Through the use of such a procedure, it is possible to determine not only the presence of RPTPκ but also its distribution in the examined tissue. Using the present invention, those of ordinary skill will readily perceive that any of a wide variety of histological methods (such as staining procedures) can be modified in order to achieve such in situ detection. Such assays for RPTPκ typically comprise incubating a biological sample, such as a biological fluid, a tissue extract, freshly harvested cells, or cells which have been incubated in tissue culture, in the presence of a detectably labeled antibody specific for RPTPκ, and detecting the antibody by any of a number of techniques well-known in the art.

The biological sample may be incubated with a solid phase support or carrier such as nitrocellulose, or other solid support which is capable of immobilizing cells, cell particles or soluble proteins. The support may then be washed with suitable buffers followed by treatment with the detectably labeled RPTPκ-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports or carriers include glass, polystyrene, polypropylene, polyethylene, dextran, nylon, amylases, natural and modified celluloses, polyacrylamides, and magnetite. The preferred carrier is totally insoluble in the solution in which the assay of the present invention takes place; partially soluble carriers well-known in the art may also be used. The support material may have virtually any possible structural configuration so long as the support-coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-RPTPκ antibody may be determined according to well-known methods. Those skilled in the art will be able to determine operative and optimal assay conditions for each determination by employing routine experimentation.

One of the ways in which the RPTPκ-specific antibody can be detectably labeled is by linking the antibody, or a second antibody which binds to the anti-RPTPκ antibody, to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect RPTPκ through the use of a radioimmunoassay (RIA) (see, for example, Work, T. S. et al., *LABORATORY TECHNIQUES AND BIOCHEMISTRY IN MOLECULAR BIOLOGY*, North Holland Publishing Company, New York, 1978, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing a labeled second antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to a fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The presence of normally functioning RPTPκ in a subject can also be tested using direct enzymatic assays, for the tyrosine phosphatase activity. Such biochemical measurements can be performed in vitro, using purified enzymes, allowing precise measurements of enzyme activity, or with membrane preparations, or whole cells, where the net phosphotyrosine level is determined.

In additional embodiments of the present invention, a nucleic acid molecule, prefereably DNA, comprising a sequence encoding an RPTPκ protein and methods for expressing the DNA molecule are provided. One of ordinary skill in the art will know how to identify and clone additional RPTP molecules, of human or other mammalian species, which have sequence homology to the RPTPκ molecules described herein, using the genetic sequences and oligonucleotides of the present invention without undue experimentation. Furthermore, manipulation of the genetic constructs of the present invention allow the grafting of a particular ligand-binding receptor domain onto the transmembrane and catalytic portions of the RPTPκ resulting in chimeric molecules. Non-limiting examples of such chimeric molecules include RPTPκ wherein the receptor portion is an epidermal growth factor receptor, a fibroblast growth factor receptor, and the like. Genetically engineered chimeric receptors are known in the art (see, for example, Riedel, H. et al., *Nature* 324:628–670 (1986)).

Genetic constructs encoding RPTPκ, functional derivative thereof, and chimeric molecules such as those described above, can be used in gene therapy. An abnormal or dysfunctional RPTPκ, which results in disease, may be replaced by infusion or implantation of cells of the desired lineage (such as hemopoietic cells, neurons, etc.) transfected with DNA encoding normal RPTPκ. Alternatively, or additionally, cells carrying a chimeric RPTPκ having a receptor portion which binds a ligand of choice (e.g., EGF) can be used for such gene therapy.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (Prog. *Nucl. Acid. Res. Molec. Biol.* 21:101–141 (1978)), and procedures for constructing recombinant molecules can be found in Sambrook et al. (supra).

Oligonucleotides representing a portion of an RPTPκ are useful for screening for the presence of genes encoding such proteins and for the cloning of an RPTPκ gene. Techniques for synthesizing such oligonucleotides are disclosed by, for example, Wu, R., et al., supra.

Protein molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: *MOLECULAR BIOLOGY OF THE GENE*, 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Mol. Biol.* 183:1–12 (1985). Using such "codon usage rules", a single oligonucleotide, or a set of oligonucleotides, that contains a theoretical "most probable" nucleotide sequence capable of encoding RPTPκ is identified.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes RPTPκ.

The oligonucleotide, or set of oligonucleotides, containing the theoretical "most probable" sequence capable of encoding the RPTPκ fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the RPTPκ gene (Sambrook et al., supra).

A suitable oligonucleotide, or set of oligonucleotides, capable of encoding a fragment of the RPTPκ gene (or complementary to such an oligonucleotide) is identified as above and synthesized, using procedures well known in the art (Belagaje, R., et al., *J. Biol. Chem.* 254:5765–5780 (1979); Maniatis, T., et al., In: *MOLECULAR MECHANISMS IN THE CONTROL OF GENE EXPRESSION*, Nierlich, D. P., et al., Eds., Acad. Press, N.Y. (1976); Wu, R., et al., *Prog. Nucl. Acid Res. Molec. Biol.* 21:101–141 (1978); Khorana, R. G., *Science* 203:614–625 (1979)). DNA synthesis may be achieved using an automated synthesizers. The oligonucleotide probe or set is hybridized by means well known in the art, against a DNA or, more preferably, a cDNA preparation derived from cells which are capable of expressing the RPTPκ gene. Techniques of nucleic acid hybridization are disclosed by Sambrook et al. (supra), and by Haymes, B. D., et al. (In: *NUCLEIC ACID HYBRIDIZATION, A PRACTICAL APPROACH*, IRL Press, Washington, D.C. (1985)), which references are herein incorporated by reference. Techniques such as, or similar to, those described above have successfully enabled the cloning of genes for human aldehyde dehydrogenases (Hsu, L. C. et al., *Proc. Natl. Acad. Sci. USA* 82:3771–3775 (1985)), fibronectin (Suzuki, S., et al., *EMBO J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:(715–8719 (1985)).

In a alternative way of cloning the RPTPκ gene, a library of expression vectors is prepared by cloning DNA or, more preferably, cDNA (from a cell capable of expressing RPTPκ) into an expression vector. The library is then screened for members capable of expressing a protein which binds to an anti-RPTPκ antibody, and which has a nucleotide sequence that is capable of encoding a polypeptide that has the same amino acid sequence as all or part of RPTPκ. In this embodiment, DNA, or more preferably cDNA, is extracted and purified from a cell which is capable of expressing RPTPκ protein. The purified cDNA is fragmented (by shearing, endonuclease digestion, etc.) to produce a pool of DNA or cDNA fragments. DNA or cDNA fragments from this pool are then cloned into an expression vector in order to produce a genomic or cDNA library of expression vectors whose members each contain a unique cloned DNA or cDNA fragment.

An "expression vector" is a vector which (due to the presence of appropriate transcriptional and/or translational control sequences) is capable of expressing a DNA molecule which has been cloned into the vector and of thereby producing a peptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. If a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing RPTPκ in order to produce a prokaryotic genomic expression vector library. Procedures for preparing cDNA and for producing a genomic library are disclosed by Sambrook et al. (supra).

A DNA sequence encoding RPTPκ of the present invention, or encoding functional derivatives thereof, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is "capable of expressing" a polypeptide if it contains nucleotide sequences which contain transcriptional and translational regulatory information and such sequences are "operably linked" to a polypeptide coding sequence. An operable linkage is a linkage in which the regulatory DNA sequences and the coding sequence are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the coding sequence may be obtained by the above-described methods. This region may be retained for its transcriptional termination regulatory sequences, such as termination and polyadenylation. Thus, by retaining the 3'-region naturally contiguous to the DNA coding sequence, the transcriptional termination signals may be provided. Where the transcriptional termination signals are not satisfactorily functional in the host cell used to express the protein, then a 3' region functional in that host cell may be substituted.

Two DNA sequences (such as a promoter region sequence and a RPTPκ coding sequence) are said to be operably linked if the nature of the linkage between the two DNA sequences does not (1) result in the introduction of a frame-shift mutation, (2) interfere with the ability of the promoter to regulate the transcription of the RPTPκ coding sequence. A promoter region is operably linked to a DNA coding sequence if the promoter is capable of effecting transcription of the coding sequence. Thus, to express the protein, transcriptional and translational signals recognized by an appropriate host are necessary. In order to be "operably linked" it is not necessary that two sequences be immediately adjacent to one another.

A promoter is a double-stranded DNA (or RNA) molecule which is capable of binding to RNA polymerase and promoting the transcription of an "operably linked" nucleic acid coding sequence. As used herein, a "promoter sequence" is the sequence of the promoter which is found on that strand of the DNA (or RNA) which is transcribed by the RNA polymerase. A "promoter sequence complement" has a sequence which is the complement of the "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to transcribe from only one strand of a duplex DNA template. Strand selection is determined by the orientation of the promoter sequence, and determines the direction of transcription since RNA is only polymerized enzymatically by the addition of a nucleotide 5' phosphate to a 3' hydroxyl terminus.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci. USA* 80:2814–2818 (1983); Davanloo, P. et al., *Proc. Natl. Acad. Sci. USA* 81:2035–2039 (1984)) polymerases; the $P_R$ and $P_L$ promoters of bacteriophage λ (*THE BACTERIOPHAGE LAMBDA*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp, recA, heat shock, and lacZ promoters of *E. coli*; the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)); the promoters of the bacteriophages of Bacillus (Gryczan, T. J., In: *THE MOLECULAR BIOLOGY OF THE BACILLI*, Academic Press, Inc., N.Y. (1982)); Streptomyces promoters (Ward, J. M., et al., *Mol. Gen. Genet.* 203:468–478 (1986)); the int promoter of bacteriophage λ; the bla promoter of the β-lactamase gene of pBR322, and the CAT promoter of the chloramphenicol acetyl transferase gene of pPR325, etc. Prokaryotic promoters are reviewed by Glick, B. R., *J. Ind. Microbiol.* 1:277–282 (1987)); Cenatiempo, Y. (*Biochimie* 68:505–516 (1986)); Watson, J. D. et al. (supra); and Gottesman, S. *Ann. Rev. Genet.* 18:415–442 (1984)).

Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* 290:304–310 (1981)); and the yeast gal4 gene promoter (Johnston, S. A., et al., *Proc. Natl. Acad. Sci. USA* 79:6971–6975 (1982); Silver, P. A., et al., *Proc. Natl. Acad. Sci. USA* 81:5951–5955 (1984)). All of the above listed references are incorporated by reference herein.

Strong promoters are preferred. Examples of such preferred promoters are those which recognize the T3, SP6 and T7 polymerases, the $P_L$ promoter of bacteriophage λ, the recA promoter and the promoter of the mouse metallothionein I gene. A most preferred promoter for eukaryotic expression of RPTPκ is an SV40 promoter such as that driving transcription in the pLSV vector (Livneh, E., et al., (1986) *J. Biol. Chem.* 261:12490–12497). The sequences of such polymerase recognition sites are disclosed by Watson, J. D. et al. (supra).

Having now generally described the invention, the same will be more readily understood through reference to the following example which is provided by way of illustration, and is not intended to be limiting of the present invention, unless specified.

6. EXAMPLE: ISOLATION AND ANALYSIS OF MURINE RPTPκ cDNA CLONES

In an effort to identify new PTPases, a mouse brain cDNA library in λgt11 was screened under relaxed stringency conditions using as a probe an oligonucleotide corresponding to the intracellular two tandem PTPase homology domains of human CD45 (Sap et al., supra). Following initial characterization and classification of the isolated clones, several subsequent rounds of screening mouse brain libraries at high stringency yielded a set of cDNA fragments that together encompassed the entire coding sequence for RPTPκ. The relationship between the different RPTPκ cDNA clones isolated was confirmed by Northern and reverse transcriptase/PCR analyses (see Materials and Methods section and FIG. 2 for details).

6.1. LIBRARY SCREENING

The original RPTPκ cDNA clone was isolated by low-stringency screening of a λgt11 mouse brain cDNA library with a probe consisting of the intracellular domain of human CD45, which contains two tandem PTPase domains (see: Sap, J. et al., 1990 *Proc. Natl. Acad. Sci. USA* 87:6112–6116, for details). After initial characterization, one of the isolated clones (λ-50, containing a 935 nucleotide fragment with characteristic homology to members of the PTPase family), was used to rescreen the same library, yielding clones λ-602 and λ-604. Sequence analysis showed that clone λ-602 was identical to λ-604 at both extremities, but was interrupted by a sequence containing stop codons in all three reading frames. Its analysis was therefore discontinued, since it is likely to represent an incompletely spliced RNA species. By contrast, λ-604 appeared to contain one PTPase homology domain and an additional 2042 nt. of upstream coding sequence, including a likely membrane-spanning region.

In order to obtain a full length RPTPκ cDNA, the entire insert of clone 604 was used to screen another (randomly primed) mouse brain cDNA library (Clontech), leading to the isolation of two hybridizing clones, λ-35 and λ-37. Clone 35 appeared to overlap with the N-terminus of clone 604 and to encompass the translational initiation codon for the RPTPκ precursor protein (see results section). Initial sequence analysis of clone 37 however revealed no overlap with the clone 604 probe, although it contained a clear additional PTPase homology followed by a stop codon in a position characteristic for the second PTPase domain of a RPTPase. Several controls were used to show that clone 37 corresponds to the bona fide C-terminus of RPTPκ. In Northern analysis, clones 37 and 604 recognize identical mRNA species in all mouse tissues examined.

A reverse transcriptase/PCR analysis on mouse liver poly(A)+ RNA using primers corresponding to clones 604 and 37, followed by cloning and sequencing, yielded a fragment of the expected size, exactly joining both clones at the same EcoRI site where each isolated cDNA clone ended.

In retrospect, clone 37 was therefore most likely picked up in the screening with the clone 604 fragment due to the existence of an additional small cDNA fragment in the original λ-37 phage isolate that went undetected due to its small size, or by fortuitous crosshybridization between the two PTPase homologies of RPTPκ. A schematic summary of the different cDNA clones discussed is included in FIG. 2.

6.2. NUCLEOTIDE SEQUENCE DETERMINATION cDNA fragments were isolated from phage clones, subcloned into Bluescript cloning vectors and subjected to sequence analysis by the dideoxynucleotide chain termination method (Sequenase, United States Biochemical) using synthetic oligonucleotide primers. All sequences were determined on both strands. Sequences were assembled and analyzed using the GCG 7 software package (Devereux, J. et al., 1984 *Nuc. Acids Res.* 12:387–395). The assembled RPTPκ cDNA nucleotide sequence was submitted to Genbank under accession number L10106.

6.3. SEQUENCE ALIGNMENTS

All DNA and protein data base searches were done with the Genetic Computer Group sequence analysis software package (Devereux et al., *Nucleic Acid Res.* 12:387–396 (1989)). The SwissProt and Gene Bank\European Molecular Biology Laboratory data bases were searched with FASTA and TFASTA, respectively (Pearson and Lipman, *Proc. Natl. Acad. Sci.* 85:2444–2448 (1988)). Proteins were aligned with the Genetics Computer Group programs, LINEUP, PILEUP, PRETTY and BESTFIT.

6.4. RESULTS AND DISCUSSION

6.4.1. ISOLATION AND SEQUENCE ANALYSIS OF cDNA CLONES ENCODING MURINE RPTPκ

The nucleotide sequence of murine RPTPκ (SEQ ID NO:3) is shown in FIGS. 1A–1H. The complete amino acid sequences of RPTPκ (SEQ ID NO:1) is shown in FIGS. 1A–1H and in FIG. 3.

The assembled RPTPκ cDNA sequence can be divided into a 5' untranslated region of 1072 base pairs, a single open reading frame of 4374 base pairs and a 3' untranslated region of 388 base pairs. The deduced amino acid sequence of the RPTPκ precursor protein is shown in FIG. 3. The translational initiation codon is identified by a standard environment for initiation of translation (Kozak, supra) and by the existence of an upstream in-frame stop codon (position -252), and is followed by a hydrophobic region that may serve as signal peptide. A second hydrophobic region is found between amino acid residues 753 and 774 and is followed by a series of predominantly basic residues, characteristic of a stop transfer sequence. These features delineate a putative extracellular region of 752 amino acid residues (including the signal sequence), and an intracellular portion of 683 amino acids. The latter contains the tandem repeat of two PTPase homologies typical for most RPTPases isolated so far (Fischer, E. H. et al., 1991 Science 253:401–406).

An intriguing feature of RPTPκ is the extended distance between its trans-membrane segment and the start of the first phosphatase homology domain. This region is about 70 residues longer than in all other previously described RPTPases, with the exception of mRPTPμ (Gebbink et al., supra).

Interestingly, a variant of RPTPκ was found by the present inventors' laboratory to contain a similarly-sized insertion in the same position. It is conceivable that such an insertion generated by alterative splicing might constitute a separate functional unit in RPTPases.

The first approximately 170 amino acids of RPTPκ show similarity (26% overall identity) to a region in the Xenopus cell surface protein A5 with features of Ig-like domains (FIG. 5). The A5 protein [SEQ ID NO:7] is thought to function in recognition between input and target neurons in the visual system (Takagi, S. et al., 1991 Neuron 7:295–307).

This first domain is followed by one Ig-like repeat (approximately residues 210 to 270) and four putative fibronectin type III-like (FN-III) repeats (residues 296 to 681). Database searching revealed clear similarity of these FN-III domains to similar domains in the tyrosine phosphatases R-PTPμ and LAR, the Drosophila R-PTPases DLAR and DPTP10D, and Drosophila neuroglian (Bieber, A. J. et al. 1989. Cell 59:447–460; Gebbink et al., supra; Streuli, M. et al., 1988, supra; Streuli, M. et al., 1989, supra; Tian et al., supra; Yang et al., supra).

Some other features of the extracellular domain of RPTPκ are noteworthy. First, it contains the sequence HAV (amino acids 340–342; within the first FN-Ill repeat) implicated in cell—cell contact in members of the cadherin family (Blaschuk, O. W. et al., 1990 J.Mol.Biol. 211:679–682). Second, the extracellular domain (640–643) contains the sequence RTKR, a consensus cleavage site for the processing endoprotease furin (Hosaka, M. et al., 1991 *J. Biol.Chem.* 266:12127–12130). Other potential posttranslational modification sites include 12 potential N-linked glycosylation sites, and SG-motifs which are candidates for chondroitin sulfate attachment (residues 172, 176, 277, 333, 662) (Kjellen, L. et al. 1991 Annu. Rev. Biochem. 60:443–470).

Overall, the sequence of RPTPκ shows a high degree of sequence similarity to mRPTPμ (77% overall similarity at the amino acid level) (Gebbink et al., supra). The sequence identity between this pair of related R-PTPases is highest in the first PTPase homology domain (80% as compared to 74% identity for the second PTPase domain). This is in contrast to the situation that has been observed for the relationship between the closely related pairs of R-PTPases LAR and HPTPδ, and RPTPβ/HPTPζ and RPTPγ (Kaplan, R. et al. 1990 *Proc. Natl. Acad. Sci. USA* 87:7000–7004; Krueger, N. X. et al., 1990 EMBO J. 9:3241–3252; Streuli, M. et al., 1988, supra). The latter pairs of related R-PTPases are more related in their second PTPase homology domains. The sequence of RPTPκ is also highly similar to that of PCR fragment PTP 191-33 described by Nishi, M. et al., 1990 FEBS Lett. 271:178–180.

7. EXAMPLE: EXPRESSION AND TISSUE DISTRIBUTION OF RPTPκ

7.1. TISSUE EXPRESSION AND NORTHERN ANALYSIS

Poly(A)+ RNA was isolated from adult mouse tissues by oligo(dT) selection as described previously (Vennstrom, B. et al. 1982 Cell 28:135–143). Five μg of poly(A)+ RNA per lane were fractionated on formaldehyde-containing 1% agarose gels, transferred to Nytran membranes, and probed under high stringency conditions with different regions of the RPTPκ cDNA. RNA loading and quality was controlled for by ethidium bromide staining.

7.1.1. EXPRESSION OF THE RPTPκ PROTEIN

In order to assemble a full-length RPTPκ cDNA from the various isolated fragments, a convenient fragment which included the N-terminus was generated from clone 35 by a PCR reaction using the N terminal primer 5'GAGCCGCG-GCTCGAGTTAACCGCCATGGATGTGGCGGCCG3' [SEQ ID NO:9] and the C-terminal primer 5'GCTCA-CAGCTAGTTCAGCCC3' [SEQ ID NO:10]. This manipulation also removed all of the 5'untranslated sequences, while retaining an optimized Kozak consensus sequence for translation initiation (Kozak, M. 1983 *Microbiol. Rev.* 47:1–45).

The amplified 470 nucleotide product was digested with Sac II and PpuM 1, and cloned between the Sac II and PpuM I sites of clone 604, yielding plasmid $pK_0$ (the Sac II site being in the polylinker region of the Bluescript cloning vector). The 1.1 kb Eco RI fragment from clone 37 (containing the C-terminal end of the coding sequence) was then cloned into the unique and corresponding Eco RI site of $pK_0$ in the appropriate orientation, yielding construct $pK_1$ containing the fully assembled coding sequence without the 5' untranslated sequences. The modified cDNA was then released as one fragment using Hpa I (N-terminal) and Xho I (C-terminal), and cloned between the Sma I and Sal I sites of a CMV-enhancer/promoter-driven eukaryotic expression vector.

7.1.2. GENERATION OF ANTISERA SPECIFIC FOR EPITOPES OF RPTPκ

Antigenicity of peptides included in the the RPTPκ protein was predicted using the Jameson-Wolf algorithm included in the GCG 7 Peptidestructure program (Devereux, J. et al., 1984 Nucl. Acids Res. 12:387–395). Two peptides were synthesized. The peptides were coupled to the protein keyhole limpet hemocyanin by glutaraldehyde crosslinking and injected into rabbits at two week intervals (100 pg per injection).

The first peptide corresponded to a site near the predicted N-terminus of the RPTPκ protein (SEQ ID NO:1), specifically, residues 60–76, having the sequence SAQE-PHYLPPEMPQGST. Immunization with this peptide yielded antiserum 116.

The second peptide corresponded to a region located at the N-terminus of the first PTPase homology in the intracellular region of the RPTPκ protein (SEQ ID NO:1), specifically, residues 910 to 929 having the sequence SASWDVAKKDQNRAK. Immunization with this peptide yielded antiserum 122) (FIG. 14).

7.1.3. TRANSFECTION, LABELING AND IMMUNO-PRECIPITATION

Subconfluent cultures of COS or HeLa cells in 10 cm diameter dishes (as indicated) were transfected by the DEAE-dextran or calcium phosphate technique, respectively. Between 48 and 72 hours after transfection, the cells were metabolically labeled for 2 hours in methionine-free medium containing 50 μCi/ml [$^{35}$S]-methionine (ICN). In the pulse-chase analysis shown in FIG. 10, cells were labeled with 200 μCi/ml of the isotope. After labeling, cells were washed in PBS and lysed in Triton-X-100 lysis buffer (50 mM Hepes pH 7.5, 150 μM NaCl, 1.5 mM $MgCl_2$, 1 mM EGTA, 10% glycerol, 1% Triton-X-100, 200 μg/ml PMSF, 10 μg/ml Aprotinin, 10 μg/ml Leupeptin) at 4° C.

Cell lysates were incubated at 4° C. for 2 hours with Protein A-Sepharose previously preincubated with the respective anti-RPTPκ antibody. Where indicated, 20 μg of the antigenic peptide was included in the immunoprecipitation reaction as a control for specificity. Immunoprecipitates were washed with high, medium and low salt buffers (Lev, S. et al., 1991 EMBO J. 10:647–654), with the exception of the 30 experiment depicted in FIG. 12 where washing was with HNTG-buffer (20 mM Hepes pH 7.5, 150 mM NaCl, 10% glycerol, 0.1% Triton-X-100). Immunoblotting analyses were performed using standard procedures.

7.1.4. PROTEIN TYROSINE PHOSPHATASE ENZYMATIC ASSAY

Phosphatase enzymatic assays were performed with RPTPκ protein immunoprecipitated with antiserum 116 (specific for the extracelular domain) from transiently transfected COS cells. The protein A-Sepharose/RPTPκ immunoprecipitated complexes were washed 4 times with HNTG, and once with M7.6 buffer (60 mM Tris, pH 7.6, 5 mM EDTA, 10 mM DTT, 50 mM NaCl, 50 μg/ml BSA).

The enzymatic assay was performed essentially as described (Streuli, M. et al., 1989 Proc. Natl. Acad. Sci. USA 86:8698–8702). The immune complexes were resuspended in 50 μl M17.6 buffer (containing 1 mM vanadate where indicated) to which had been added 10 μl [$^{32}$p] tyrosine phosphorylated myelin basic protein (approximately 12 μM). The [$^{32}$P]-tyrosine-phosphorylated myelin basic protein had been produced by in vitro phosphorylation using EGF-receptor immunoprecipitated from A431 cells. The reactions were incubated for 15 minutes at 37° C. with shaking, stopped with 750 μl of an acidic stop mix containing activated charcoal, and the amount of released free [$^{32}$p]-phosphate was measured.

7.1.5. ENDOGLYCOSIDASE F TREATMENT

Cultures of cells transfected with RPTPκ cDNA were lysed in 1% SDS at 100° C. for 3 minutes. The total cell lysates were sonicated 3 times at full speed, then diluted with distilled water to decrease the concentration of SDS to 0.1%. The cell lysates were incubated at 37° C. for 18 hours in the presence of 0.2 units endoglycosidase F (Boehringer-Mannheim), 0.25M sodium acetate, pH 5.2, 20 mM EDTA, 10 mM β-mercaptoethanol and 0.6% NP-40. The total enzyme-treated lysate was directly loaded onto SDS-PAGE gels, which were run, transferred to nitrocellulose and blotted with antiserum 116 or antiserum 122 as indicated.

7.1.6. SITE-DIRECTED MUTAGENESIS

In vitro site-directed mutagenesis was performed using a commercially available kit from Clontech, using the manufacturer's instructions. An oligonucleotide having the sequence CTACACCCACATCTAACGAACCGTGAAG-CAGGG [SEQ ID NO:11] was used to modify the amino acid sequence RTKR in the cleavage site to the sequence LTNR. Mutagenesis was confirmed by direct DNA sequencing.

7.1.7. IN SITU HYBRIDIZATION OF RPTPκ cDNA TO RAT TISSUES

Sprague-Dawley rats were sacrificed by decapitation, and their brains were removed and sectioned into 20 μm sections in a cryostat. Sections were postfixed in 4% paraformaldehyde in 0.1M sodium phosphate, pH 7.4, for 20 min.

A 50 base oligonucleotide complementary to residues 1493–1543 of the isolated RPTPκ cDNA sequence (SEQ ID NO:3) was used as a probe. The oligonucleotide was labeled with [(α-$^{35}$S]dATP (NEN, DuPont) using terminal deoxynucleotidyl transferase (Boehringer Mannheim) and purified using Sephadex G25 quick spin columns (Boehringer Mannheim). The specific activity of the labeled probe was from $2\times10^8$ to $5\times10^8$ cpm/μg DNA. Prehybridization and hybridization were carried out in a buffer containing 50% deionized formamide, 4× SCC, 1× Denhardt's solution, 500 μg/ml denatured salmon sperm DNA, 250 μg/ml yeast tRNA and 10% dextran sulfate.

The tissue sections were incubated in a humidified environment for 14–18 h at 42°–46° C. in hybridization solution containing the labeled probe and 10 mM dithiothreitol. Specificity controls were performed on adjacent sections by adding to the labeled oligonucleotide a 100-fold excess of the unlabeled oligonucleotide. After incubation, sections were washed in 2 changes of 2× SSC at room temperature for 1 h, then in 1× SCC at 50° C. for 30 min, 0.5×SCC at 50° C. for 30 min, and in 0.5×SCC at room temperature for 10 min. Sections were dehydrated and exposed to X-Omat film for 3 weeks.

7.2. RESULTS AND DISCUSSION

7.2.1. EXPRESSION OF RPTPκ IN ADULT TISSUES

Northern blot analysis on adult mouse tissues (FIG. 6) revealed that RPTPκ expression is broad. Two major transcripts of 5.3 and 7.0 kb were detectable at different levels in all examined tissues except in spleen and testis. Particularly high levels of the 5.3 kb transcript were seen in liver and kidney tissue. An identical pattern was detected using as a probe both an N-terminal and central part of the cDNA. Although the 5.3 kb size is similar to the 5.7 kb described for mRPTP (Gebbink et al., supra), RPTPκ appears to be much more widely expressed than mRPTPμ. Expression of the latter is virtually restricted to lung and, at lower levels, brain and heart.

7.2.2. TRANSIENT EXPRESSION AND ENZYMATIC ACTIVITY OF RPTPκ

As described above, the RPTPκ coding sequence was cloned into an expression vector under the control of the CMV enhancer and promoter after manipulation to remove the untranslated leader sequence. The construct was transiently transfected into HeLa cells which were metabolically labeled with [$^{35}$S]-methionine, lysed and subjected to a radioimmunoprecipitation assay. The antibody probe was an antiserum raised against a peptide located in the N-terminus of the protein (residues 60 to 76). This antiserum precipitated a protein of about 210 kDa from RPTPκ transfected cells, but not from mock transfected cells (transfected with an "empty" expression vector) (FIG. 7). This immunoprecipitation was blocked by inclusion of the antigenic peptide in the immunoprecipitation reaction (lanes 3 and 6), but not by inclusion of a heterologous peptide corresponding to the first catalytic homology domain of RPTPκ.

To confirm that the protein encoded by the RPTPκ cDNA had PTPase enzymatic activity, immune complexes from transfected cells were incubated in an appropriate buffer with [$^{32}$P]-tyrosine phosphorylated myelin basic protein as a substrate. As shown in FIG. 8, approximately 3-fold higher PTPase activity was detectable in immune complexes from RPTPκ transfected cells as compared to control cells. This PTPase activity could be significantly inhibited by vanadate.

7.2.3. IN SITU HYBRIDIZATION ANALYSIS OF RPTPκ EXPRESSION IN THE DEVELOPING AND ADULT CENRAL NERVOUS SYSTEM

The level of expression of RPTPκ mRNA was generally higher in the developing than in the adult central nervous system (CNS). At embryonic day 18 (E18) and at E20, the RPTP(κ) mRNA levels were highest in the cerebral cortex and hippocampal formation, followed by the cerebellum, brain stem and spinal cord. In the rest of the embryo, the highest levels were found in the liver, kidney and intestine (left panel, FIG. 13A). At postnatal day 6 (P6) and P8, expression was maximal in the cortex, olfactory bulb and hippocampal formation, especially in the dentate gyrus and CA3. In the cerebellum, the expression was highest in the granular cell layer, which in this stage of development still occupies the outermost cell layer of the cerebellum (right panel, FIG. 13B).

In the adult rat, expression was lower, but was clearly visible in the olfactory bulb and throughout the cortex, including the pyriform and cingulate cortex. Expression of the RPTPκ mRNA was also observed in the hippocampal formation. Interestingly, expression in the cerebellum was barely detectable in the adult. This was in marked contrast with the distinct patten and high level of expression observed at P6 and P8, a period of active cerebellar development.

The in situ hybridization studies confirmed the expression of the RPTPκ in several organs. In addition, they demonstrated that, in the CNS, RPTPκ is expressed in specific areas in a developmentally regulated manner. The levels of RPTPκ expression are higher in the actively developing areas, but expression persists in the adult, mainly in certain areas of the cortex and in the hippocampal formation. These findings are consistent with the idea that CNS RPTPases are actively involved in development and plasticity. Studies on the expression of RPTPs in Drosophila have led to similar suggestions (Tian et al., supra; Yang et al., supra).

8. EXAMPLE: CHROMOSOMAL LOCALIZATION OF THE MURINE RPTPκ GENE

The method was essentially as described previously (Sap, J. et al., 1990 Proc. Natl. Acad. Sci. USA 87:6112–6116; Silver, J., 1985 J. Hered. 76:436–440; Taylor, B., 1978, In: H. C. Morse, III (ed.), ORIGINS OF INBRED MICE, Academic Press, New York, pp. 423–438; Taylor, B. A., 1989 In: M. F. Lyon et al., eds, GENETIC VARIANTS AND STRAINS OF THE LABORATORY MOUSE. Oxford University Press, New York, pp. 773–796). Southern blotting analysis of Taq I-digested mouse genomic DNA with the 604 RPTPκ probe revealed an array of 12 fragments that appeared invariant between the inbred strains surveyed, as well as a smaller set of variable bands that were used to define two allelic forms of the gene:

(1) a was defined by the presence of 1.9, 3.5 and 3.8 kb fragments and was present in inbred mouse strains AKR/J, C3H/HeJ, DBA/J, SM/J; and (2) b was defined by the presence of a 4.1 kb fragment and was present in inbred mouse strains C57BL/6J, 020/A, C57L/J, SWR/J, SJL/J, BALB/cJ, STS/A, NZB/B1NJ).

Analysis of the inheritance pattern of this variant among recombinant inbred strains of mice (Table I), and comparison of strain distribution patterns thus obtained with those generated previously for other genetic markers, revealed close linkage between RPTPκ and two markers of proximal chromosome 10: D10Mit3 (2 discordancies among 22 strains typed, indicating a distance of 2.6 cM between the loci (0.3 cM to 13.0 cM defined 95% confidence limits); and Ly-41 (0 discordancies among 30 strains typed, indicating a distance between the loci of <3.5 cM at 95% confidence). The gene symbol Ptpk is proposed by the inventors, consistent with the symbol Ptpa previously assigned to RPTPα (Sap et al., supra).

This region of mouse chromosome 10 contains multiple genes with human homologues mapping to chromosome 6q. Based on synteny, this would predict a localization of the human RPTPκ homologue to 6q, in contrast to 18pter-q11 for human RPTPμ (Gebbink et al., supra).

TABLE I

DNA FRAGMENT LENGTH VARIANT ASSOCIATED WITH THE MOUSE RPTPk GENE.

A. Alleles and strain distribution patterns

| Allele | (Size kb)) | Strains |
|---|---|---|
| a | 1.9 + 3.5 + 3.8 | AKR/J, C3H/HeJ, DBA/2J, SM/J |
| | | AKXL-5, 6, 7, 8, 17, 21, 25, 28, 29, 37, 38 |
| | | BXD-1, 2, 5, 14, 15, 18, 21, 23, 25, 28, 32 |
| | | BXH-2, 4, 7, 8, 12, 14, 19 |
| | | NXSM-D, L, W, X |
| | | OXA-4, 5, 7, 8, 13 |

TABLE I-continued

DNA FRAGMENT LENGTH VARIANT ASSOCIATED WITH THE MOUSE RPTPk GENE.

| b | 4.1 | C57BL/6J, 020/A, C57L/J, |
| --- | --- | --- |
| | | SWR/J, SJL/J, BALB/CJ, STS/A, |
| | | NZB/B1NJ |
| | | AKXL-9, 12, 13, 14, 16, 19, 24 |
| | | BXD-6, 8, 9, 11, 12, 13, 16, 19, 20, |
| | | 22, 24, 27, 29, 30, 31 |
| | | BXH-3, 6, 9, 10, 11 |
| | | NXSM-C, E, F, I, N, P, Q, T1, T2, U, Z |
| | | OXA-1, 2, 3, 6, 9, 10, 11, 12, 14 |

B. Linkage of ptpk to other markers typed in Recombinant Inbred strains

| Marker | Chr | R/N | Odds | Distance (cM) |
| --- | --- | --- | --- | --- |
| D10Mit3 | 10 | 2/22 | 0.00941 | 2.6 (0.3–13.0) |
| Ly-41 | 10 | O/30 | <0.00001 | 0.0 (<3.5) |

A) 10 μg quantities of liver or spleen genomic DNA were digested with Taql enzyme and analyzed by Southern blotting with the 604 RPTPk probe ae described previously to define two alleles of the ptpk gene and to follow their inheritance in panels of recombinant inbred (RI) strains of mice.
B) The resulting strain distributions were compared with those previously determined for other loci in these panels of mice. Two matches were found that were unlikely to be due to chance at a 5% confidence level. For each of these, the number of non-matching RI strains found (R) is shown as a fraction of the total number of RI strains typed (N) for the two markers, together with the odds of observing that number of non-matches or a smaller one by chance (Blank, R.D. et al., 1988 Genetics 120:1073–1083), the estimated distance between the marker and ptpk, and the 95% confidence limits for that estimate (Silver, supra; Taylor, 1978, supra).

9. EXAMPLE: POSTTRANSLATIONAL PROTEOLYTIC PROCESSING OF RPTPκ

During experiments designed to achieve stable expression of RPTPκ in 3T3 cells, the present inventors observed the generation of a product of an unexpected, smaller size as well as the generation of aberrantly-sized products upon transient transfection of COS cells.

The present inventors noted the presence of a proteolytic cleavage signal in the extracellular domain of RPTPκ, (RTKR, residues 640 to 643, in the fourth FN-III repeat; FIG. 3) and wished to examine its significance in light of these observations. Thus, additional experiments were performed in COS cells transfected by the DEAE-dextran technique.

In order to detect cleavage products which may have accumulated, total cell lysates were directly loaded onto SDS-PAGE gels, run in electrophoresis, transferred to nitrocellulose, and immunoblotted with the two different anti-RPTPκ peptide antisera (described above) specific for either the N-terminus or for an epitope near the first PTPase homology domain in the intracellular portion.

In lysates from transfected cells, but not from mock transfected cells, both antisera recognized the same 210 kDa protein described above. The antiserum specific for the N terminus also recognized a smaller 110 kDa protein. The antiserum specific for the cytoplasmic region recognized a smaller 100 kDa protein (FIG. 9).

The three polypeptides (210, 110 and 100 kDa) were further characterized by subjecting the total cell lysates to endoglycosidase F digestion before SDS-PAGE and immunoblotting. Such a treatment would be expected mainly to affect the mobility of a protein containing the glycosylated extracellular domain. Following endoglycosidase F treatment, the mobility of the 210 kDa and 110 kDa proteins was significantly reduced, to 160 kDa and 89 kDa respectively. In contrast, the mobility of the 100 kDa band detected with antiserum 122 specific for an epitope in the intracellular domain) was only slightly affected, suggesting that the 100 kDa peptide includes a minor glycosylation component (FIG. 9).

The above results, as well as pulse-chase analysis shown in FIG. 10, are consistent with the cleavage of a 210 kDa RPTPκ precursor protein into an N-terminal 110 kDa product encompassing most of the extracellular domain, and a 100 kDa moiety containing the intracellular portion and about 100 residues of extracellular sequence (FIG. 14). A consensus site for cleavage by furin, a processing endopeptidase (Hosaka et al., supra), is indeed located 113 amino acids upstream of the start of the transmembrane segment (RTKR, residues 640–643), which would leave one potential N-glycosylation site in the C-terminal cleavage product.

In order to confirm directly that proteolytic cleavage occurred at the RTKR (furin-recognized) site, site-directed mutagenesis was used to mutate this site to LTNR, and the effects of this mutation on the processing of the RPTPκ precursor was examined. As shown in FIG. 12, the mutant cDNA gave rise to only a 210 kDa product. These results provide evidence that the RTKR region is the likely proteolytic cleavage signal and site for processing, of the RPTPκ proprotein.

The inventors next tested whether the cleavage products were associated. This was accomplished by performing an immunoprecipitation with antiserum 116, specific for the extracellular 110 kDa product, on lysates of cells transfected with the wild type (wt) RPTPκ cDNA. Immunoblotting of this precipitate with antiserum 122, specific for an intracellular RPTPκ epitope, detected the presence of the 100 kDa C-terminal cleavage product in the precipitate (FIG. 12). This observation strongly suggested that at least a portion of the two RPTPκ cleavage products remained associated after cleavage, and that the 100 and 110 kDa species may be considered as subunits of a single complex (FIG. 14). Experiments with a secreted form of the extracellular domain of RPTPκ suggested that this association was not mediated by a disulfide linkage, since no association could be detected using SDS-PAGE under nonreducing conditions.

A similar posttranslational processing event has been described for the RPTPase LAR and for the Ng-CAM protein (Burgoon, M. et al. 1992. J. Cell Biol. 112:1017–1029; Streuli, M. et al., 1992 EMBO J. 11:897–907; Yu, Q. et al., 1992 Oncogene 7:1051–1057). In addition, a potential cleavage site exists in the corresponding position in mRPTPμ (Gebbink et al., supra). It is therefore likely that proteolytic processing of RPTPs may be a more general phenomenon.

Such cleavage, as described above, may allow controlled shedding of the N-terminal 110 kDa subunit, and thus render the membrane-bound 100 kDa form of RPTPκ insensitive to modulation by binding of proteins in the cellular environment. Alternatively, shedding might release a soluble species which retains binding activity to the putative RPTPκ ligands. Interestingly, secreted soluble forms of extracellular domains have been described for tyrosine kinase receptors such as the FGF-receptor (Johnson, D. E. et al., *Molec. Cell. Biol.* 11:4627–4634 (1991)). However these secreted forms were generated by an alternative splicing mechanism.

10. EXAMPLE: ISOLATION AND ANALYSIS OF HUMAN RPTPκ (MCP7) cDNA CLONES

10.1. PCR AND cDNA CLONING METHODS

Poly(A)+ RNA was isolated from SK-BR-3 cells (ATCC HTB30) and cDNA synthesized using avian myeloblastosis virus (AMV) reverse transcriptase as described (Sambrook, J. et al., *MOLECULAR CLONING: A LABORATORY MANUAL*, 2nd Edition, Cold Spring Harbor Press, Cold Spring Harbor, N.Y. (1989)). Polymerase chain reaction using a pool of degenerated oligonucleotides based on two highly conserved regions of the PTPase domain (Vogel, W. et al., *Science* 259:1611–1614 (1993) was performed under standard conditions, and PCR products were subcloned in Bluescript KS+ vector (Stratagene). Sequence analysis was done by the dideoxynucleotide chain termination method (Sanger et al., 1977) using Sequenase (United States Biochemical). a lambda ZAP 11 LIBRARY (Stratagene) from SK-BR-3 poly(A)+ RNA was screened with a PCR fragment probe under high stringency conditions (Ullrich, A. et al., 1985, *Nature* 313:756–711).

10.2. RESULTS

The complexity of PTPases expressed in the human breast cancer cell line SK-BR-3 was examined by performing a PCR analysis. The primers were degenerate sequences corresponding to conserved sequences within the PTP catalytic domains shared by all identified PTPases (Vogel, W. et al. 1993, *Science* 259:1611–1614). Sequence analysis of the cloned PCR products revealed the presence of several known PTPases, including PTP1B, LAR, TC-PTP, PTPδ, PTPε, PTPγ, and PTPH1, as well as some novel members of the PTPase family.

One of the novel sequences, designated MCP7 ("mammary carcinoma-derived PTPase, clone 7"), was highly represented (18%) in the 121 clones examined. The 2066 bp MCP7 PCR fragment was used to screen a λ ZAP II SK-BR-3 cDNA library at high stringency. Eleven overlapping clones spanning an overall region of approximately 6.1 kb were analyzed, revealing an open reading frame encoding 1444 amino acids, followed by a 3' untranslated region of 1.8 kb.

The nucleotide sequence of human RPTPκ (SEQ ID NO:4) is shown in FIGS. 15A–15E. The deduced amino acid sequence of MCP7 (SEQ ID NO:2) is also shown in FIGS. 15A–15E and displays the structural organization of a type II transmembrane PTPase (Fischer et al., 1991, Charbonneau, H. et al., *Annu. Rev. Cell Biol.* 8:463–493 (1992). The N-terminal hydrophobic stretch of 20–26 amino acids is typical of signal peptides (von Heijne, G., *J. Mol. Biol.* 184:99–105 (1985). A second region consisting of hydrophobic residues is found between positions 755 and 774 and is predicted to be a single a helical transmembrane domain. It is followed by a short region of mainly basic residues characteristic of a transfer stop sequence (Wickner, W. T. et al., *Science* 230:400–406 (1985)). The amino-terminal portion of the putative extracellular domain contains a sequence motif, a so called MAM domain, spanning a region of about 170 residues. The MAM structural motif was recently established by comparison of several functionally diverse receptors (including RPTPμ [SEQ ID NO:6] and the A5 protein) [SEQ ID NO:7] and is thought to play a role in cell adhesion (Beckmann et al., supra). This motif is followed by one possible Ig-like domain (residues 207–277). The remaining extracellular portion contains conserved sequence motifs, indicating that it is composed of four FN-III related domains corresponding to the FN-III-like domains of LAR, PTPβ and RPTPμ. The extracellular domain contains 12 potential N-glycosylation sites, indicating that MCP7 is highly glycosylated. Interestingly, MCP7 contains the motif RXR/LR (residues 640–643) within the fourth FN-III domain. This motif has been described as the cleavage site for the subtilisin-like endoprotease, furin (Barr, P. J., *Cell* 66:1–3 (1991); Hosaka et al., supra).

The cytoplasmic part of MCP7 is composed of two PTPase domains containing the conserved amino acid sequences typical of all known PTPases (Saito, H. et al., *Cell Growth Diff.* 2:59–65 (1991)). A particularly intriguing feature is the region linking the transmembrane domain to the amino-terminal PTPase domain, which is nearly twice as large as that of most other receptor-like PTPases. A similar extended distance is shared only by the homologous PTPase, hRPTPμ (FIGS. 16A–B, lower lines). The overall homology between MCP7 and hRPTPμ is 77%, to which the N-terminal and C-terminal PTPase domains contribute 91% and 86%, respectively (FIGS. 16A–B).

10.3. DISCUSSION

The extracellular domain of MCP7 is composed of one MAM domain, which is a sequence motif spanning about 170 residues, which was recently established by comparison of several functionally diverse receptors (including RPTPμ and the A5 protein) and is thought to play a role in cell adhesion (Beckmann & Bork, 1993, TIBS 18:40). The extracellular domain of MCP7 further includes one Ig-like, and four FN-type III-like segments. It therefore shares structural features with some cell adhesion molecules, permitting the classification of MCP7 into the type II PTPase class.

MCP7 is highly homologous to mRPTPμ which has a more restricted expression pattern in lung, brain and heart (Gebbink et al., supra). MCP7 is expressed as a molecule consisting of two noncovalently linked subunits, a structural feature already shown for LAR. A similar processing motif was also determined within the extracellular domain of mRPTPμ (RTKR residues 632–635), which suggest that this structural organization is typical for the family of type II phosphatases. Proteolytic cleavage also occurs in the extracellular domain of the cell adhesion molecule Ng-CAM in a region containing the dibasic processing motif (Burgoon, M. P. et al., *J. Cell. Biol.* 112:1017–1029 (1991)). The functional significance of this structure is not yet clear. For LAR, a shedding of the extracellular E-subunit was observed in a density-dependent manner (Streuli et al., supra). It is likely that this shedding is due to a conformational change in the extracellular domain caused by homophilic or hydrophilic interactions between the molecules on the surface of neighboring cells that weakens the interaction between the non-covalently linked subunits. The effect of this shedding on the activity of the PTPase domains within the cells is not yet clear, but a modification of the activity of the phosphatase or a change in the sensitivity to modifying processes is probable.

11. EXAMPLE: TISSUE DISTRIBUTION OF HUMAN RPTPκ

11.1. RNA EXTRACTION AND NORTHERN BLOT ANALYSIS

Total RNA was isolated by the guanidinium isothiocyanate method (Chirgwin et al., 1979, *Biochemistry* 18:5294–5299) from human tissue and cultured cells grown to confluency. Poly(A)+ RNA was prepared on an oligo(dT) column (Aviv & Leder, 1972, *Proc. Natl. Acad. Sci. USA* 69:1408–1412). 4 μg of poly(A)+ RNA was fractionated on a 1.2% formaldehyde-agarose gel and subsequently transferred to nitrocellulose filters (Schleicher & Schuell). Hybridization was performed in 50% formamide, 5× SSC, 50 mM $NaH_2PO_4$, pH 6.8, 0.5% SDS, 0.1 mg/ml sonicated salmon sperm DNA, and 5× Denhardt solution at 42° C. overnight with $1-3 \times 10^6$ cpm/ml of $^{32}$P-labeled random-primed DNA (United States Biochemical). Filters were washed with 2× SSC, 0.1% SDS, and 0.2× SSC, 0.1% SDS at 45° C., and exposed 5 days using an intensifying screen at −80° C.

11.2. RESULTS

Northern blot analysis revealed a broad tissue distribution of MCP7 (FIG. 17). The 6.7 kb transcript was found at elevated levels in lung and colon tissue, and, to a lesser extent, in liver, pancreas, stomach, kidney, and placenta. No transcript was detected in spleen tissue.

The expression pattern of MCP7 in different mammary carcinoma-derived cell lines is shown in FIG. 18. Although MCP7 expression was observed in all of the cell lines tested, the quantity of transcripts differed significantly. A second transcript with a size of 4.9 kb was also detected in all cell lines displaying a strong signal. Moreover, MDA-MB-435 cells contained a specific 1.4 kb mRNA that hybridized with the MCP7 probe. It is interesting to note that the intensity of the Northern hybridization signals shown in FIG. 18 correlate with the abnormal over expression of EGF-R and HER2/neu RTKs. Expression of MCP7 was also detected in human melanoma cell lines and some colon-carcinoma derived cell lines.

12. EXAMPLE: TRANSIENT EXPRESSION OF HUMAN RPTPκ

12.1. METHODS

MCP7 cDNA was cloned into a cytomegalovirus early promoter-based expression plasmid (pCMV). The RTK expression plasmids used were described previously (Vogel, W. et al., 1993 Science 259:1611–1614). At 30 hours prior transfection, $3 \times 10^5$ cells of human embryonic kidney fibroblast cell line 293 (ATCC CRL 1573), grown in Dulbecco's modified Eagle's medium (DMEM) which included 4500 mg/l glucose, 9% fetal calf serum, and 2 mM glutamine, were seeded into a well of a six-well dish.

Transfections with CsCl-purified plasmid DNA were then carried out using the calcium phosphate coprecipitation technique according to the protocol of Chen and Okayama (Chen, C. and Okayawa, H., 1987, Mol. Cell. Biol. 7:2745–2752) with a total amount of 4 μg, which included only 0.2 μg expression plasmid and complemented with empty vector DNA (Gorman, C. M. et al., 1989, Virology 171:377–385; Lammers, R. et al., 1990, J. Biol. Chem. 265:16886–16890). At 16 hours after transfection, cells were washed once and starved with medium containing 0.5% fetal calf serum.

For metabolic labeling, MEN containing Earle's salt, but lacking L-methionine, was used instead of DMEM. [$^{35}$S] methionine at 40 μCi/ml (1,000 Ci/mmol) was added.

Cells were stimulated with an appropriate ligand for 10 min. Epidermal growth factor (EGF) at 100 ng/ml was used to stimulate cells transfected with EGF-R, HER1/2, EK-R or EP-R. Insulin at 1 μg/ml was used to stimulate cells transfected with IR. SCF at 100 ng/ml was used to stimulate cells transfected with p145$^{c-kit}$. After stimulation, cells were lysed in 200 μl lysis buffer (50 mM HEPES, pH 7.5; 150 mM NaCl, 1.5 mM MgCl$_2$, 1 mM EGTA, 10% glycerol, 1% Triton X-100, 2 mM phenylmethylsulfonylfluoride, 10 μg/ml aprotinin, 1 mM Na-orthovanadate). The lysates were precleared by centrifugation at 125,000×g for 10 min at 4° C., and 1/10 of the volume of the supernatant was mixed with SDS sample buffer.

Proteins were separated by SDS-PAGE and transferred to nitrocellulose membranes. For detection of phosphotyrosine and protein antigens on immunoblots, the ECL system (Amersham) in conjunction with horseradish peroxidase-conjugated goat anti-mouse or goat anti-rabbit antibody (Biorad) was used. In order to reprobe with other antibodies, blots were incubated for 1 hour in 67 mM Tris-HCl (pH 6.8), 2% SDS, and 0.1% β-mercaptoethanol at 50° C.

For immunoprecipitation, radiolabelled cells were incubated with antiserum at 4° C. for 2 hours, washed three times with PBS (15 mM NaCl, 3 mM Kcl, 80 mM Na$_2$HPO$_4$.H$_2$O, 1.5 mM KH$_2$PO$_4$, pH 7.4) to remove unbound antibodies, lysed, and precleared by centrifugation. Protein A-sepharose (Pharmacia) in a volume of 20 μl has added and incubated for two hours on a rotating wheel at 4° C. Precipitates were washed four times with HNTG-buffer (20 mM HEPES, ph. 7.5, 150 mM Na Cl, 0.1% Triton X-100,. 10% glycerin), SDS-sample buffer added, and SDS-PAGE was performed. X-ray film was then exposed to the dried gel two days.

The polyclonal antiserum, Ab 116, specific for the extracellular domain of murine RPTPκ, was raised against a peptide sequence (residues 60–76) within the extracellular domain of the mouse homolog of MCP7, and which was perfectly conserved in the human sequence as described supra, in Section 10. The monoclonal antibody specific for phosphotyrosine, 5E.2, was described previously (Fendly, B. M. et al., 1990, Canc. Res. 50:1550–1558).

12.2. RESULTS

Forty eight hours after transfection of MCP7 cDNA, using a cytomegalovirus promoter-based expression vector, into 293 embryonic kidney cells, radiolabelled cells were incubated with Ab 116. Cells were washed, lysed, and the antibody-bound material was immunoprecipitated.

MCP7 expression was found on the cell surface only, and appeared as a band having an apparent molecular weight of 185 kDa. The larger size than the calculated molecular weight of 163 kDa was probably due to extensive glycosylation of the extracellular domain.

Two additional bands of 97 kDa and 116 kDa were immunoprecipitated (FIG. 19A, lane 1); these bands were not detectable in cells transfected with a control vector. Such lower molecular weight products were thought to be cleavage products since the extracellular domain contains a common cleavage motif (RXR/LR; residues 640–643, FIGS. 15A–15E. for processing by the endoprotease furin. These products are similar to the cleavage products described above for murine RPTPκ. Furthermore, similar processing of the extracellular domain of LAR has been described (Streuli et al., supra).

The 116 kDa fragment, the α subunit, represents most of the extracellular domain and is highly glycosylated, as indicated by the broadness of the band upon polyacrylamide gel electrophoresis analysis and its apparent molecular weight, which exceeded the calculated value, based on the sequence between residing 20 and 639, by 47 kD. The 97 kDa fragment, the β subunit, corresponds to an intracellular and transmembrane domain and also includes a short extracellular segment which is thought to interact with the a subunit. The relatively minor discrepancy between the observed 97 kDa molecular weight size and the calculated 91.4 kDa molecular weight of the β subunit can be explained by the presence of only one potential N-glycosylation site.

The α and β subunit are believed to form a stable complex, such that immunoprecipitation by an antibody specific for the extracellular domain would detect both subunits. To confirm that the 116 kDa band corresponded to the a subunit cleavage product and not merely to a non-specifically cross-reacting species, lysates from MCP7 cDNA-transfected 293 cells were subjected to Western blots using antiserum 116 specific for an N-terminal epitope. With this approach, a band of about 116 kDa as well as an unprocessed precursor were found (FIG. 19B, right panel, lane 1), neither of which were detected in 293 cells at comparable levels transfected with a control vector (FIG. 19B, right panel, lane 2).

13. EXAMPLE: EXAMINATION OF PTPase ENZYMATIC ACTIVITY OF HUMAN RPTPκ

To prove that the RPTPκ designated MCP7 is indeed a PTPase enzyme, the above transient expression system in 293 cells was used.

Coexpression of MCP7 with a panel of different RTKs representing different structural subclasses allowed the examination of more physiological substrates for the PTPase as dephosphorylation targets than those commonly used.

To ensure that the protein localized mainly in the membrane and to avoid an overload of the cell transport system, these transfection experiments were performed with only small amounts of plasmid compared to the original protocols (Gorman, C. M. et al., *Virology* 171:377–385 (1989); Lammers, R. et al., *J. Biol. Chem.* 265:16886–16890 (1990)). The receptors tested were mainly chimeric receptors, the respective kinase function of which was under the control of an EGF-R extracellular domain (Lee, J. et al., *EMBO J.* 8:167–173 (1989); Herbst, R. et al., *J. Biol. Chem.* 266:19908–19916 (1991); Seedorf, K. et al., *J. Biol. Chem.* 266:12424–12431 (1991)). Human 293 fibroblasts were transfected with equal amounts of expression plasmids encoding for an RTK and either MCP7 or a control vector. After stimulation with the appropriate ligand for the RTK, cells were lysed, equal aliquots were resolved by SDS PAGE, and the phosphotyrosine level of the receptors was examined by immunoblotting with the anti-phosphotyrosine antibody 5E2 (Fendly, G. M. et al., *Canc. Res.* 50:1550–1558 (1990)).

Co-expression of I-R, EGF-R, EP-R, EK-R, and SCFR/c-kit with MCP7 resulted in a marked decrease in the ligand-induced receptor phosphotyrosine content when compared with control transfections in which MCP7 expression plasmid had been omitted (FIG. 20A, lanes 1 and 9; 20B, lanes 1, 5, and 9). In contrast, HER1-2 appeared to be a poor substrate of MCP7, since only weak reduction of the ligand-induced phosphorylation state of this chimera was observed (FIG. 20A, lane 5). Interestingly, the intracellularly localized, incompletely processed precursor forms of I-R, EGF-R and EP-R (FIG. 20A, lanes 2, 4 and 10, 12; 20B, lanes 2, 4), as well as that of HER 1-2 (FIG. 20A, lanes 6, 8), were efficiently dephosphorylated), suggesting that MCP7 was present and active in the same intracellular compartments as the co-expressed RTKs before reaching the cell surface.

To verify the above effects and to rule out differences in RTK expression levels, the above blots were re-probed with RTK-specific and RPTPκ-specific antibodies. The results indicated that expression levels of the various RTKs were equivalent.

14. EXAMPLE: CORRELATION BETWEEN HUMAN RPTPκ EXPRESSION AND CELL DENSITY

The presence of motifs in the extracellular domain of human RPTPκ that resemble motifs found in proteins involved in cell—cell and cell-extracellular matrix interactions prompted an investigation of the effect on expression level of cell density in culture.

An equal number of SK-BR-3 cells was distributed onto either one, two, or four 15-cm dishes and incubated for two days under standard growth conditions. When harvested after two days, cells seeded at the various starting densities were found to be 100%, 70%, and 40% confluent, respectively. Poly(A)+ RNA was prepared and Northern blot analysis was conducted as described supra, in Section 11.1, using a probe corresponding to the extracellular domain of MCP7. The results indicated that the level of MCP7 transcripts increased with increased cell density (FIG. 21A).

To determine whether this effect was unique to SK-BR-3 cells, an identical experiment was performed using the colon carcinoma-derived cell line HT 29. Expression of MCP7 mRNA was also found to be density-dependent with these cells (FIG. 19B).

As a control, the expression of mRNA encoding the enzyme GAPDH was examined in the above cells at various densities. No density dependence of the expression of these transcripts were obvserved.

The above results support the hypothesis RPTPκ, and other RPTPs of the type II and type III families, are involved in, and modulated by, cell adhesion events (Charbonneau et al., supra). PTPases appear to be involved in events leading to growth arrest by cell—cell contact (Klarlund, supra). The presence of orthovanadate, a potent inhibitor of phosphatase activity dimishes normal contact inhibition of 3T3 cells. Furthermore, PTPase activity associated with the membrane fraction of 3T3 cells increased 8 fold when cells were grown to a higher density (Pallen, C. J. et al., *Proc. Natl. Acad. Sci. USA* 88:6996–7000 (1991)).

The combination of CAM motifs in the extracellular domain or RPTPκ and the intracellular PTPase activity indicates that RPTPκ may act as an important mediator of events associated with arrest of cell growth. The structural features of human RPTPκ described above, the density-dependent upregulation or its expression, and its potent activity in dephosphorylating RTKs supports the emerging picture of the pivotal role of RPTPκ in growth arrest through contact inhibition, as well as a role as a tumor suppressor gene.

15. EXAMPLE: HOMOPHILIC BINDING BY A RECEPTOR TYROSINE PHOSPHATASE

The present work investigates whether, similar to "classical" members of the CAM family, RPTPases might be capable of homophilic intercellular interaction (Q. Yu, T. Lenardo, R. A. Weinberg, Oncogene 7, 1051 (1992)). Reasoning that analysis of cell adhesion by the RPTPase RPTPκ would be facilitated by its ectopic expression in a cell line likely to lack conserved ligands for a mammalian RPTPase, we stably introduced an RPTPκ cDNA into Drosophila S2 cells. These cells have a very low capacity for spontaneous aggregation or adhesion, making them an ideal and established system for such studies (H. Kramer, R. L. Cagan, S. L. Zipursky, Nature 352, 207). Cells transfected with a vector containing the RPTPκ cDNA in the sense orientation with respect to the heat-shock protein 70 (hsp 70) promoter of the vector, and induced by brief heat treatment expressed a protein of 210 kD detectable by immunoblotting with anti-RPTPκ antiserum (FIG. 22A). This protein corresponds to the unprocessed form of RPTPκ seen in mammalian cells (Y.-P. Jiang et al. Mol. Cell. Biol. 13, 2942 (1993)). In addition, after longer expression periods, a protein species of 110 kD also appeared, suggesting that the RPTPκ protein may at least, in part, partly be processed in the Drosophila cell line in a manner similar to the way in which it is processed in mammalian cells, i.e., through proteolytic cleavage by a furin type endoprotease (FIG. 22A) (Y.-P. Jiang et al. Mol. Cell. Biol. 13, 2942 (1993)). A Drosophila furin homolog has recently been described (A. J. M. Roebroek et al., EMBO J. 12, 1853 (1993)).

In order to study whether RPTPκ expression may mediate cell—cell aggregation, cells stably transfected with the RPTPκ cDNA in either the sense orientation (sense cDNA) or the antisense orientation (antisense cDNA) were tested in an aggregation assay. uninduced and heat shock-induced cells were resuspended, subjected to rotary shaking to ensure mixing and to avoid adhesion to the vessel, and were then assayed for aggregate formation. The formation of a large number of aggregates consisting of more than 10 and up to approximately 100 cells was observed in heat-shocked sense cDNA-expressing cells only, whereas control cells (i.e., antisense cDNA transfected cells or non-heat shocked cells) remained essentially single cell suspensions (FIGS. 22B–22C). Two methods of quantitation, counting of aggregates under the microscope, and determination of superthreshold particles with a Coulter-counter (FIGS. 22C–22D) confirmed this conclusion. The fact that aggregation was incomplete, with a large proportion of RPTPκ transfected cells remaining as single cells throughout the assay period, is most likely due to the fact that the transfected cell population consisted of an uncloned pool of cells presumably differing in their levels of RPTPκ expression. Notably, the conditions of the assay (i.e., medium, timescale, and speed of shaking) are similar to those used to demonstrate the adhesive properties of a number of well established adhesion molecules (H. Kramer, R. L. Cagan, S. L. Zipursky, Nature 352, 207 (1991); P. M. Snow, A. J. Bieber, C. Goodman, Cell 59, 313 (1989)). Therefore, in view of the difficulty of measuring binding affinities of many cell adhesion molecules which rely on cooperativity, it is likely that the strength of cell—cell-interaction conferred by expression of RPTPκ is comparable to that of established, "classical", cell adhesion molecules.

The above experiments were performed with a full-length RPTPκ cDNA, leaving unclear whether the phosphatase activity of the intracellular domain is required to confer adhesive properties. In several instances, an intact intracellular domain of cell adhesion molecules has in fact been shown to be required for certain aspects of cell—cell interaction (A. Nafaguchi and M. Takeichi, EMBO J. 7, 3679 (1988); S. H. Jaffe et al., Proc. Natl. Acad. Sci. USA 87, 3589 (1990), R. O. Hynes, Cell 69, 111 (1992)). To test this issue, a cDNA encoding a mutant protein lacking most of the intracellular, catalytic, domain of RPTPκ was constructed. FIG. 22E shows that such a truncation did not negatively interfere with cell aggregation as measured in this type of assay. The role of the furin cleavage site in the extracellular domain of RPTPκ was also tested. Mutation of this site also left the adhesive behavior intact, suggesting that cleavage of the RPTPκ proprotein (Y.-P. Jiang et al. Mol. Cell. Biol. 13, 2942 (1993)) is not required for induction of cell aggregation.

Cell adhesion molecules have been described which either do (e.g. cadherin family members and integrins), or do not (e.g. N-CAM, Ng-CAM) require the presence of $Ca^{++}$ (G. M. Edelman, Immun. Rev. 100, 11 (1987); A. F. Williams and A. N. Barclay, Annu. Rev. Immunol. 6, 381 (1988); M. Grumet, Curr. Opin. Neurobiol. 1, 370 (1991), R. O. Hynes, Cell 69, 111 (1992), B. Geiger and O. Ayalon, Annu. Rev. Cell Biol. 8 (1992)). The experiments presented in FIGS. 22A–22E were performed in the presence of 10 mM $Ca^{++}$ in the aggregating cell suspension. Performing a similar experiment in the absence of calcium ions and in the presence of 1 mm EGTA revealed no calcium requirement for RPTPκ mediated cellular aggregation under the conditions of the assay.

The observed aggregation correlating with expression of RPTPκ could be accounted for by either a homophilic binding mechanism, in which cell—cell binding is mediated by interaction between RPTPκ proteins on different cells within aggregates, or by binding of the RPTPκ protein to a second cell-surface ligand intrinsic to the parental transfected cells. It was possible to distinguish between these two hypotheses by marking different populations of cells with the fluorescent lipophilic dye 1,1'-dioctadecyl-3,3,3',3'tetramethylindocarbocyanine perchlorate (diI) (J. Schlessinger et al. Science 195, 307 (1977)), and then testing them for their ability to co-aggregate. In these experiments, RPTPκ expressing and non-expressing cells were labeled with diI, mixed with unlabeled cells of either RPTPκ expressing or non-expressing types, and the presence of cells of either type in the aggregates formed was monitored by fluorescence microscopy. The results are illustrated in FIG. 23. Strikingly, mixing of unlabeled, RPTPκ positive cells with labeled, RPTPκ negative cells led to the formation of aggregates consisting exclusively of unlabeled cells. Conversely, when the RPTPκ expressing cells were labeled and allowed to aggregate with unlabeled control cells, aggregates consisted entirely of labeled cells, demonstrating that diI labeling does not interfere with the aggregation capacity of the transfected cells. Mixing of labeled and unlabeled cells, both expressing RPTPκ, led to the formation of mixed aggregates consisting of cells of either staining type, thus confirming that both diI stained and unstained cells have the ability to co-aggregate. These results suggest that aggregation of the RPTPκ transfected cells requires the presence of the protein on all cells within the aggregate, implying a homophilic binding mechanism.

It was next determined whether the extracellular domain of RPTPκ was able to function by itself as a substrate for attachment of cells expressing the RPTPκ protein independent of other factors to assist in the adhesion process. A baculovirus expression system was used to produce a soluble recombinant protein consisting of virtually the entire extracellular domain of the RPTPκ protein, fused to placental alkaline phosphatase, which served as a tag for purification and detection (J. G. Flanahan and P. Leder, Cell 63, 185 (1990)). Fusion between the two protein moieties was designed to occur precisely before the furin proteolytic cleavage signal in the fourth fibronectin type III repeat in RPTPκ (Y.-P. Jiang et al. Mol. Cell. Biol. 13, 2942 (1993)). The purified recombinant protein (K2AP) was used to coat bacteriological Petri dishes, and monitored for its ability to allow attachment of RPTPκ-expressing S2 cells. Only induced, RPTPκ expressing cells showed adhesive behavior to the K2AP coated surface (FIGS. 24A–24D; Table II below).

TABLE II

| Cell type: | S2 control uninduced | S2 control induced | S2-R-PTP-k uninduced | S2-R-PTP-k induced | L6 | L6R-PTP-k |
|---|---|---|---|---|---|---|
| Protein | | | | | | |
| K2AP-a | – | – | – | +++ | + | ++ |
| K2AP-b | – | – | – | +++ | + | ++ |
| AP | – | – | – | – | – | – |
| HER | – | – | – | – | – | – |
| BSA | – | – | – | – | – | – |
| Fibronectin | +++ | +++ | +++ | +++ | + | + |
| polylysine | n.d. | n.d. | n.d. | n.d. | +++ | +++ |

Summary of adhesion data of different cell types to surfaces coated with purified K2AP protein, or other proteins (–:no cells attached; +: 50–150 cells; ++150–500; +++:>500; n.d.: not determined)

K2APa: K2AP protein purified by elution from affinity column at alkaline pH.

K2APb: K2AP protein purified by elution from affinity column using 50% ethylene glycol.

AP: alkaline phosphatase control protein (J. G. Flanahan and P. Leder, Cell 63, 185 (1990)), corresponding to the tag portion of the K2AP fusion protein.

HER: Human EGF-receptor extracellular domain affinity-purified from a baculovirus expression system (I. Lax et al., J. Biol. Chem. 266, 13828 (1991)).

BSA: bovine serum albumin.

L6-R-PTPκ: a clone of L6 cells stably transfected with the R-PTPκ protein.

No attachment occurred to control coated surfaces, which included alkaline phosphatase or the recombinant extracellular domain of human EGF-receptor (I. Lax et al., J. Biol. Chem. 266, 13828 (1991)), also purified by affinity chromatography from a baculovirus expression system. Whereas the above experiments were performed in the context of insect cells, the effect of RPTPκ protein expression in mammalian cells in a similar cell-to-substrate adhesion assay was also tested. In contrast to parental Drosophila S2 cells, rat L6 myoblast cells, the mammalian cell line used as a recipient for RPTPκ overexpression, already shows a low level of spontaneous adhesion to a K2AP protein coated surface. However, stable overexpression of an RPTPκ cDNA in these cells led to a significant (2.7 fold +/−1.0; n=3) increase in adhesive capacity to a surface coated with the recombinant soluble extracellular domain of the RPTPκ protein (FIG. 24).

15.1 Discussion

Cell—cell contact is generally considered to play a critical role in various aspects of malignancy. For example, escape from contact inhibition is a classical parameter of transformation, and, additionally, many links between cell—cell interactions and such phenomena as tumor invasion and metastasis are apparent (F. Van Roy and M. Mareel, TICB 2, 163 (1992)). The above data clearly demonstrate that an RPTPase of the LAR-like subfamily (containing a combination of Ig and fibronectin type III domains) is capable of homophilic binding between neighboring cells, leading to the identification of a function for the extracellular domains of such molecules. This makes it likely that other members of this RPTPase subfamily can behave in a similar fashion, and extends the series of links that have recently emerged between the adhesive properties of cells, and signal transduction pathways involving tyrosine phosphorylation. For instance, adherens junctions correspond to sites of increased tyrosine phosphorylation and appear to be subject to its control, and reagents directed at integrins or extracellular domains of established CAMs have been shown to elicit changes in cellular tyrosine phosphorylation (J. R. Atashi et al., Neuron 8, 831 (1992); T. Volberg et al., EMBO J. 11, 1733 (1992); R. L. Juliano and S. Haskill, J. Cell Biol. 120, 577 (1993)). In addition, reagents directed toward cell adhesion molecules are known to activate a number of second messenger signals (Schuch, U. Lohse, M. Schachner, Neuron 3, 13–20 (1989); P. Doherty, S. V. Ashton, S. E. Moore, F. Walsh, Cell 67, 21 (1991)). The above observation suggests mechanisms by which such signals might be generated. For example, direct cell—cell contact between RPTPases on adjacent cells could lead to local RPTPase oligomerization events affecting either the catalytic activity or localization of RPTPases, which in turn have been suggested to modulate the activity of src-family tyrosine kinases (H. L. Ostergaard et al., Proc. Natl. Acad. Sci. USA 86, 8959 (1989); T. Mustelin and A. Altman, Oncogene 5, 809 (1989); X. M. Zheng, Y. Wang, C. J. Pallen, Nature 359, 336 (1992)). Moreover, the similar structural and functional properties of the extracellular domains of RPTPases and CAMs prompts the speculation that RPTPases may, in addition to self-interaction, also be capable of interacting heterophilically with other molecules involved in cell adhesion, whether in cis or in trans (G. M. Edelman, Immun. Rev. 100, 11 (1987); A. F. Williams and A. N. Barclay, Annu. Rev. Immunol. 6, 381 (1988); M. Grumet, Curr. Opin. Neurobiol. 1, 370 (1991), R. O. Hynes, Cell 69, 111 (1992), B. Geiger and O. Ayalon, Annu. Rev. Cell Biol. 8 (1992), M. Grumet and G. M. Edelman, J. Cell Biol. 106, 487–503 (1988); G. A. Kadmon, A. Kowitz, P. Altevogt, M. Schachner, J. Cell Biol. 110, 193 (1990); A. A. Reyes, R. Akeson, L. Brezina, G. J. Cole, Cell Reg. 1, 567 (1990); P. Sonderegger and F. G. Rathjen, J. Cell Biol. 119, 1387 (1992); M. G. Grumet, A. Flaccus, R. U. Margolis, J. Cell Biol. 120, 815 (1993)).

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated nucleic acid molecule having the nucleotide sequence SEQ ID No:3.

2. An isolated nucleic acid molecule having the nucleotide sequence SEQ ID No:4.

3. An isolated nucleic acid molecule comprising a nucleotide sequence that encodes a polypeptide having the amino acid sequence SEQ ID NO:1 or SEQ ID NO:2.

4. An isolated nucleic acid molecule comprising a nucleotide sequence that encodes a full length naturally occurring receptor-type protein tyrosine phosphatase kappa, wherein said nucleotide sequence hybridizes to the complement of a nucleic acid molecule comprising a nucleotide sequence that encodes a polypeptide having the amino acid sequence set forth in SEQ ID NO: 1 or SEQ ID NO: 2, under hybridization conditions at least as stringent as the following: hybridization in 50% formamide, 5× SSC, 50 mM $NaH_2PO_4$, pH 6.8, 0.5% SDS, 0.1 mg/ml sonicated salmon sperm DNA and 5× Denhart solution at 42° C. overnight; washing with 2× SSC, 0.1% SDS at 45° C.; and washing with 0.2× SSC, 0.1% SDS at 45° C.

5. An isolated nucleic acid molecule comprising a nucleotid sequence that encodes one of the following domains in SEQ ID NO:2: one of the four fibronectin type III repeats, the MAM domain, the signal peptide, the transmembrane domain, the extracellular domain, or one of the two phosphatase domains.

6. The nucleic acid molecule of claim 3 or 4 in which the nucleic acid molecule is a cDNA molecule.

7. The nucleic acid molecule of claim 3 or 4 in which the nucleic acid molecule is a genomic DNA molecule.

8. A recombinant vector containing the nucleic acid molecule of claim 3, 4 or 5.

9. An expression vector containing the nucleic acid molecule of claim 3, 4 or 5 operatively associated with a regulatory nucleotide sequence that controls expression of the nucleic acid molecule in a host cell.

10. A host cell containing the nucleic acid molecule of claim 3, 4 or 5.

11. A host cell containing the nucleic acid molecule of claim 3, 4 or 5 operatively associated with a regulatory nucleotide sequence that controls expression of the nucleic acid molecule in a host cell.

12. The host cell of claim 11 in which the host cell is prokaryotic.

13. A method for producing a receptor-type protein tyrosine phosphatase κ polypeptide comprising:

(a) culturing the host cell of claim 12 under conditions that would allow expression of the receptor-type protein tyrosine phosphatase κ polypeptide; and (b) recovering the receptor-type protein tyrosine phosphatase κ polypeptide from the culture.

14. The host cell of claim 11 in which the host cell is eukaryotic.

15. A method for producing a receptor-type protein tyrosine phosphatase κ polypeptide comprising:

(a) culturing the host cell of claim 14 under conditions that would allow expression of the receptor-type protein tyrosine phosphatase κ polypeptide; and (b) recovering the receptor-type protein tyrosine phosphatase κ polypeptide from the culture.

16. An isolated nucleic acid molecule comprising the complement of a nucleotide sequence that encodes a polypeptide having the amino acid sequence SEQ ID NO:1 or SEQ ID NO:2.

17. An isolated nucleic acid molecule comprising the complement of a nucleotide sequence that encodes one of the following domains in SEQ ID NO:2: one of the four fibronectin type III repeats, the MAM domain, the signal peptide, the transmembrane domain, the extracellular domain, or one of the two phosphatase domains.

18. A recombinant vector containing the nucleic acid molecule of claim 16 or 17.

19. A host cell containing the nucleic acid molecule of claim 16 or 17.

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1457 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

| Met | Asp | Val | Ala | Ala | Ala | Leu | Pro | Ala | Phe | Val | Ala | Leu | Trp | Leu |
| 1 | | | | 5 | | | | | 10 | | | | | 15 |

| Leu | Tyr | Pro | Trp | Pro | Leu | Leu | Gly | Ser | Ala | Leu | Gly | Gln | Phe | Ser | Ala |
| | | | 20 | | | | | 25 | | | | | 30 | | |

| Gly | Gly | Cys | Thr | Phe | Asp | Asp | Gly | Pro | Gly | Ala | Cys | Asp | Tyr | His | Gln |
| | | 35 | | | | | 40 | | | | | 45 | | | |

| Asp | Leu | Tyr | Asp | Asp | Phe | Glu | Trp | Val | His | Val | Ser | Ala | Gln | Glu | Pro |
| | 50 | | | | | 55 | | | | | 60 | | | | |

| His | Tyr | Leu | Pro | Pro | Glu | Met | Pro | Gln | Gly | Ser | Tyr | Met | Val | Val | Asp |
| 65 | | | | | 70 | | | | | 75 | | | | | 80 |

| Ser | Ser | Asn | His | Asp | Pro | Gly | Glu | Lys | Ala | Arg | Leu | Gln | Leu | Pro | Thr |
| | | | | 85 | | | | | 90 | | | | | 95 | |

| Met | Lys | Glu | Asn | Asp | Thr | His | Cys | Ile | Asp | Phe | Ser | Tyr | Leu | Leu | Tyr |
| | | | | 100 | | | | | 105 | | | | | 110 | |

| Ser | Gln | Lys | Gly | Leu | Asn | Pro | Gly | Thr | Leu | Asn | Ile | Leu | Val | Arg | Val |
| | | | 115 | | | | | 120 | | | | | 125 | | |

| Asn | Lys | Gly | Pro | Leu | Ala | Asn | Pro | Ile | Trp | Asn | Val | Thr | Gly | Phe | Thr |
| | | 130 | | | | | 135 | | | | | 140 | | | |

| Gly | Arg | Asp | Trp | Leu | Arg | Ala | Glu | Leu | Ala | Val | Ser | Thr | Phe | Trp | Pro |
| 145 | | | | | 150 | | | | | 155 | | | | | 160 |

| Asn | Glu | Tyr | Gln | Val | Ile | Phe | Glu | Ala | Glu | Val | Ser | Gly | Gly | Arg | Ser |
| | | | | 165 | | | | | 170 | | | | | 175 | |

| Gly | Tyr | Ile | Ala | Ile | Asp | Asp | Ile | Gln | Val | Leu | Ser | Tyr | Pro | Cys | Asp |
| | | | 180 | | | | | 185 | | | | | 190 | | |

| Lys | Ser | Pro | His | Phe | Leu | Arg | Leu | Gly | Asp | Val | Glu | Val | Asn | Ala | Gly |
| | | 195 | | | | | 200 | | | | | 205 | | | |

| Gln | Asn | Ala | Thr | Phe | Gln | Cys | Ile | Ala | Thr | Gly | Arg | Asp | Ala | Val | His |
| 210 | | | | | 215 | | | | | 220 | | | | | |

| Asn | Lys | Leu | Trp | Leu | Gln | Arg | Arg | Asn | Gly | Glu | Asp | Ile | Pro | Val | Ala |
| 225 | | | | | 230 | | | | | 235 | | | | | 240 |

| Gln | Thr | Lys | Asn | Ile | Asn | His | Arg | Arg | Phe | Ala | Ala | Ser | Phe | Arg | Leu |
| | | | | 245 | | | | | 250 | | | | | 255 | |

| Gln | Glu | Val | Thr | Lys | Thr | Asp | Gln | Asp | Leu | Tyr | Arg | Cys | Val | Thr | Gln |
| | | | 260 | | | | | 265 | | | | | 270 | | |

| Ser | Glu | Arg | Gly | Ser | Gly | Val | Ser | Asn | Phe | Ala | Gln | Leu | Ile | Val | Arg |
| | | 275 | | | | | 280 | | | | | 285 | | | |

| Glu | Pro | Pro | Arg | Pro | Ile | Ala | Pro | Pro | Gln | Leu | Leu | Gly | Val | Gly | Pro |
| | 290 | | | | | 295 | | | | | 300 | | | | |

| Thr | Tyr | Leu | Leu | Ile | Gln | Leu | Asn | Ala | Asn | Ser | Ile | Ile | Gly | Asp | Gly |
| 305 | | | | | 310 | | | | | 315 | | | | | 320 |

| Pro | Ile | Ile | Leu | Lys | Glu | Val | Glu | Tyr | Arg | Met | Thr | Ser | Gly | Ser | Trp |
| | | | | 325 | | | | | 330 | | | | | 335 | |

| Thr | Glu | Thr | His | Ala | Val | Asn | Ala | Pro | Thr | Tyr | Lys | Leu | Trp | His | Leu |
| | | | 340 | | | | | 345 | | | | | 350 | | |

| Asp | Pro | Asp | Thr | Glu | Tyr | Glu | Ile | Arg | Val | Leu | Leu | Thr | Arg | Pro | Gly |
| | | 355 | | | | | 360 | | | | | 365 | | | |

| Glu | Gly | Gly | Thr | Gly | Leu | Pro | Gly | Pro | Pro | Leu | Ile | Thr | Arg | Thr | Lys |
| | 370 | | | | | 375 | | | | | 380 | | | | |

| Cys | Ala | Glu | Pro | Met | Arg | Thr | Pro | Lys | Thr | Leu | Lys | Ile | Ala | Glu | Ile |
| 385 | | | | | 390 | | | | | 395 | | | | | 400 |

| Gln | Ala | Arg | Arg | Ile | Ala | Val | Asp | Trp | Glu | Ser | Leu | Gly | Tyr | Asn | Ile |
| | | | | 405 | | | | | 410 | | | | | 415 | |

| Thr | Arg | Cys | His | Thr | Phe | Asn | Val | Thr | Ile | Cys | Tyr | His | Tyr | Phe | Arg |

-continued

```
                        420                            425                            430
Gly His Asn Glu Ser Arg Ala Asp Cys Leu Asp Met Asp Pro Lys Ala
        435                         440                 445
Pro Gln His Val Val Asn His Leu Pro Pro Tyr Thr Asn Val Ser Leu
450                         455                 460
Lys Met Ile Leu Thr Asn Pro Glu Gly Arg Lys Glu Ser Glu Glu Thr
465                 470                 475                         480
Ile Ile Gln Thr Asp Glu Asp Val Pro Gly Pro Val Pro Val Lys Ser
                485                         490                 495
Leu Gln Gly Thr Ser Phe Glu Asn Lys Ile Phe Leu Asn Trp Lys Glu
                500                     505                 510
Pro Leu Glu Pro Asn Gly Ile Ile Thr Gln Tyr Glu Val Ser Tyr Ser
            515                 520                 525
Ser Ile Arg Ser Phe Asp Pro Ala Val Pro Val Ala Gly Pro Pro Gln
    530                     535                 540
Thr Val Ser Asn Leu Trp Asn Ser Thr His His Val Phe Met His Leu
545                     550                     555                 560
His Pro Gly Thr Thr Tyr Gln Phe Phe Ile Arg Ala Ser Thr Val Lys
                    565                 570                 575
Gly Phe Gly Pro Ala Thr Ala Ile Asn Val Thr Thr Asn Ile Ser Ala
            580                 585                     590
Pro Ser Leu Pro Asp Tyr Glu Gly Val Asp Ala Ser Leu Asn Glu Thr
            595                 600             605
Ala Thr Thr Ile Thr Val Leu Leu Arg Pro Ala Gln Ala Lys Gly Ala
    610                 615                 620
Pro Ile Ser Ala Tyr Gln Ile Val Val Glu Gln Leu His Pro His Arg
625                     630                 635                     640
Thr Lys Arg Glu Ala Gly Ala Met Glu Cys Tyr Gln Val Pro Val Thr
                645                 650             655
Tyr Gln Asn Ala Leu Ser Gly Gly Ala Pro Tyr Tyr Phe Ala Ala Glu
            660                 665                 670
Leu Pro Pro Gly Asn Leu Pro Glu Pro Ala Pro Phe Thr Val Gly Asp
        675                 680                 685
Asn Arg Thr Tyr Lys Gly Phe Trp Asn Pro Pro Leu Ala Pro Arg Lys
    690                 695                     700
Gly Tyr Asn Ile Tyr Phe Gln Ala Met Ser Ser Val Glu Lys Glu Thr
705                 710                 715                     720
Lys Thr Gln Cys Val Arg Ile Ala Thr Lys Ala Ala Ala Thr Glu Glu
                725                 730                 735
Pro Glu Val Ile Pro Asp Pro Ala Lys Gln Thr Asp Arg Val Val Lys
            740                 745                 750
Ile Ala Gly Ile Ser Ala Gly Ile Leu Val Phe Ile Leu Leu Leu Leu
        755                 760                 765
Val Val Ile Val Ile Val Lys Lys Ser Lys Leu Ala Lys Lys Arg Lys
    770                     775                 780
Asp Ala Met Gly Asn Thr Arg Gln Glu Met Thr His Met Val Asn Ala
785                 790                 795                     800
Met Asp Arg Ser Tyr Ala Asp Gln Ser Thr Leu His Ala Glu Asp Pro
                805                 810                 815
Leu Ser Leu Thr Phe Met Asp Gln His Asn Phe Ser Pro Arg Leu Pro
            820                 825                 830
Asn Asp Pro Leu Val Pro Thr Ala Val Leu Asp Glu Asn His Ser Ala
        835                 840                 845
```

```
Thr Ala Glu Ser Ser Arg Leu Leu Asp Val Pro Arg Tyr Leu Cys Glu
    850                 855                 860
Gly Thr Glu Ser Pro Tyr Gln Thr Gly Gln Leu His Pro Ala Ile Arg
865                 870                 875                 880
Val Ala Asp Leu Leu Gln His Ile Asn Leu Met Lys Thr Ser Asp Ser
                885                 890                 895
Tyr Gly Phe Lys Glu Glu Tyr Glu Ser Phe Phe Glu Gly Gln Ser Ala
            900                 905                 910
Ser Trp Asp Val Ala Lys Lys Asp Gln Asn Arg Ala Lys Asn Arg Tyr
        915                 920                 925
Gly Asn Ile Ile Ala Tyr Asp His Ser Arg Val Ile Leu Gln Pro Val
    930                 935                 940
Glu Asp Asp Pro Ser Ser Asp Tyr Ile Asn Ala Asn Tyr Ile Asp Ile
945                 950                 955                 960
Trp Leu Tyr Arg Asp Gly Tyr Gln Arg Pro Ser His Tyr Ile Ala Thr
                965                 970                 975
Gln Gly Pro Val His Glu Thr Val Tyr Asp Phe Trp Arg Met Val Trp
            980                 985                 990
Gln Glu Gln Ser Ala Cys Ile Val Met Val Thr Asn Leu Val Glu Val
        995                 1000                1005
Gly Arg Val Lys Cys Tyr Lys Tyr Trp Pro Asp Asp Thr Glu Val Tyr
    1010                1015                1020
Gly Asp Phe Lys Val Thr Cys Val Glu Met Glu Pro Leu Ala Glu Tyr
1025                1030                1035                1040
Val Val Arg Thr Phe Thr Leu Glu Arg Arg Gly Tyr Asn Glu Ile Arg
                1045                1050                1055
Glu Val Lys Gln Phe His Phe Thr Gly Trp Pro Asp His Gly Val Pro
            1060                1065                1070
Tyr His Ala Thr Gly Leu Leu Ser Phe Ile Arg Arg Val Lys Leu Ser
        1075                1080                1085
Asn Pro Pro Ser Ala Gly Pro Ile Val Val His Cys Ser Ala Gly Ala
    1090                1095                1100
Gly Arg Thr Gly Cys Tyr Ile Val Ile Asp Ile Met Leu Asp Met Ala
1105                1110                1115                1120
Glu Arg Glu Gly Val Val Asp Ile Tyr Asn Cys Val Lys Ala Leu Arg
                1125                1130                1135
Ser Arg Arg Ile Asn Met Val Gln Thr Glu Glu Gln Tyr Ile Phe Ile
            1140                1145                1150
His Asp Ala Ile Leu Glu Ala Cys Leu Cys Gly Glu Thr Ala Ile Pro
        1155                1160                1165
Val Cys Glu Phe Lys Ala Ala Tyr Phe Asp Met Ile Arg Ile Asp Ser
    1170                1175                1180
Gln Thr Asn Ser Ser His Leu Lys Asp Glu Phe Gln Thr Leu Asn Ser
1185                1190                1195                1200
Val Thr Pro Arg Leu Gln Ala Glu Asp Cys Ser Ile Ala Cys Leu Pro
                1205                1210                1215
Arg Asn His Asp Lys Asn Arg Phe Met Asp Met Leu Pro Pro Asp Arg
            1220                1225                1230
Cys Leu Pro Phe Leu Ile Thr Ile Asp Gly Glu Ser Ser Asn Tyr Ile
        1235                1240                1245
Asn Ala Ala Leu Met Asp Ser Tyr Arg Gln Pro Ala Ala Phe Ile Val
    1250                1255                1260
Thr Gln Tyr Pro Leu Pro Asn Thr Val Lys Asp Phe Trp Arg Leu Val
1265                1270                1275                1280
```

Tyr Asp Tyr Gly Cys Thr Ser Ile Val Met Leu Asn Glu Val Asp Leu
            1285                    1290                    1295

Ser Gln Gly Cys Pro Gln Tyr Trp Pro Glu Glu Gly Met Leu Arg Tyr
            1300                    1305                    1310

Gly Pro Ile Gln Val Glu Cys Met Ser Cys Ser Met Asp Cys Asp Val
            1315                    1320                    1325

Ile Asn Arg Ile Phe Arg Ile Cys Asn Leu Thr Arg Pro Gln Glu Gly
            1330                    1335                    1340

Tyr Leu Met Val Gln Gln Phe Gln Tyr Leu Gly Trp Ala Ser His Arg
1345                    1350                    1355                    1360

Glu Val Pro Gly Ser Lys Arg Ser Phe Leu Lys Leu Ile Leu Gln Val
            1365                    1370                    1375

Glu Lys Trp Gln Glu Glu Cys Glu Glu Gly Glu Gly Arg Thr Ile Ile
            1380                    1385                    1390

His Cys Leu Asn Gly Gly Gly Arg Ser Gly Met Phe Cys Ala Ile Gly
            1395                    1400                    1405

Ile Val Val Glu Met Val Lys Arg Gln Asn Val Val Asp Val Phe His
            1410                    1415                    1420

Ala Val Lys Thr Leu Arg Asn Ser Lys Pro Asn Met Val Glu Ala Pro
1425                    1430                    1435                    1440

Glu Gln Tyr Arg Phe Cys Tyr Asp Val Ala Leu Glu Tyr Leu Glu Ser
            1445                    1450                    1455

Ser ( 2 ) INFORMATION FOR SEQ ID NO:2:

( i ) SEQUENCE CHARACTERISTICS:
        ( A ) LENGTH: 1439 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Asp Thr Thr Ala Ala Ala Ala Leu Pro Ala Phe Val Ala Leu Leu
1                       5                       10                      15

Leu Leu Ser Pro Trp Pro Leu Leu Gly Ser Ala Gln Gly Gln Phe Ser
            20                      25                      30

Ala Gly Gly Cys Thr Phe Asp Asp Gly Pro Gly Ala Cys Asp Tyr His
            35                      40                      45

Gln Asp Leu Tyr Asp Asp Phe Glu Trp Val His Val Ser Ala Gln Glu
            50                      55                      60

Pro His Tyr Leu Pro Pro Glu Met Pro Gln Gly Ser Tyr Met Ile Val
65                      70                      75                      80

Asp Ser Ser Asp His Asp Pro Gly Glu Lys Ala Arg Leu Gln Leu Pro
            85                      90                      95

Thr Met Lys Glu Asn Asp Thr His Cys Ile Asp Phe Ser Tyr Leu Leu
            100                     105                     110

Tyr Ser Gln Lys Gly Leu Asn Pro Gly Thr Leu Asn Ile Leu Val Arg
            115                     120                     125

Val Asn Lys Gly Pro Leu Ala Asn Pro Ile Trp Asn Val Thr Gly Phe
            130                     135                     140

Thr Gly Arg Asp Trp Leu Arg Ala Glu Leu Ala Val Ser Thr Phe Trp
145                     150                     155                     160

Pro Asn Glu Tyr Gln Val Ile Phe Glu Ala Glu Val Ser Gly Gly Arg
            165                     170                     175

```
Ser  Gly  Tyr  Ile  Ala  Ile  Asp  Asp  Ile  Gln  Val  Leu  Ser  Tyr  Pro  Cys
               180                      185                     190

Asp  Lys  Ser  Pro  His  Phe  Leu  Arg  Leu  Gly  Asp  Val  Glu  Val  Asn  Ala
          195                      200                     205

Gly  Gln  Asn  Ala  Thr  Phe  Gln  Cys  Ile  Ala  Thr  Gly  Arg  Asp  Ala  Val
     210                      215                     220

His  Asn  Lys  Leu  Trp  Leu  Gln  Arg  Arg  Asn  Gly  Glu  Asp  Ile  Pro  Val
225                      230                     235                          240

Ala  Gln  Thr  Lys  Asn  Ile  Asn  His  Arg  Arg  Phe  Ala  Ala  Ser  Phe  Arg
               245                      250                     255

Leu  Gln  Glu  Val  Thr  Lys  Thr  Asp  Gln  Asp  Leu  Tyr  Arg  Cys  Val  Thr
               260                      265                     270

Gln  Ser  Glu  Arg  Gly  Ser  Gly  Val  Ser  Asn  Phe  Ala  Gln  Leu  Ile  Val
          275                      280                     285

Arg  Glu  Pro  Pro  Arg  Pro  Ile  Ala  Pro  Pro  Gln  Leu  Leu  Gly  Val  Gly
     290                      295                     300

Pro  Thr  Tyr  Leu  Leu  Ile  Gln  Leu  Asn  Ala  Asn  Ser  Ile  Ile  Gly  Asp
305                      310                     315                          320

Gly  Pro  Ile  Ile  Leu  Lys  Glu  Val  Glu  Tyr  Arg  Met  Thr  Ser  Gly  Ser
                    325                      330                     335

Trp  Thr  Glu  Thr  His  Ala  Val  Asn  Ala  Pro  Thr  Tyr  Lys  Leu  Trp  His
               340                      345                     350

Leu  Asp  Pro  Asp  Thr  Glu  Tyr  Glu  Ile  Arg  Val  Leu  Leu  Thr  Arg  Pro
          355                      360                     365

Gly  Glu  Gly  Gly  Thr  Gly  Leu  Pro  Gly  Pro  Pro  Leu  Ile  Thr  Arg  Thr
     370                      375                     380

Lys  Cys  Ala  Glu  Pro  Met  Arg  Thr  Pro  Lys  Thr  Leu  Lys  Ile  Ala  Glu
385                      390                     395                          400

Ile  Gln  Ala  Arg  Arg  Ile  Ala  Val  Asp  Trp  Glu  Ser  Leu  Gly  Tyr  Asn
                    405                      410                     415

Ile  Thr  Arg  Cys  His  Thr  Phe  Asn  Val  Thr  Ile  Cys  Tyr  His  Tyr  Phe
               420                      425                     430

Arg  Gly  His  Asn  Glu  Ser  Lys  Ala  Asp  Cys  Leu  Asp  Met  Asp  Pro  Lys
               435                      440                     445

Ala  Pro  Gln  His  Val  Val  Asn  His  Leu  Pro  Pro  Tyr  Thr  Asn  Val  Ser
     450                      455                     460

Leu  Lys  Met  Ile  Leu  Thr  Asn  Pro  Glu  Gly  Arg  Lys  Glu  Ser  Glu  Glu
465                      470                     475                          480

Thr  Ile  Ile  Gln  Thr  Asp  Glu  Asp  Val  Pro  Gly  Pro  Val  Pro  Val  Lys
                    485                      490                     495

Ser  Leu  Gln  Gly  Thr  Ser  Phe  Glu  Asn  Lys  Ile  Phe  Leu  Asn  Trp  Lys
               500                      505                     510

Glu  Pro  Leu  Asp  Pro  Asn  Gly  Ile  Ile  Thr  Gln  Tyr  Glu  Ile  Ser  Tyr
          515                      520                     525

Ser  Ser  Ile  Arg  Ser  Phe  Asp  Pro  Ala  Val  Pro  Val  Ala  Gly  Pro  Pro
     530                      535                     540

Gln  Thr  Val  Ser  Asn  Leu  Trp  Asn  Ser  Thr  His  His  Val  Phe  Met  His
545                      550                     555                          560

Leu  His  Pro  Gly  Thr  Tyr  Gln  Phe  Phe  Ile  Arg  Ala  Ser  Thr  Val
               565                      570                     575

Lys  Gly  Phe  Gly  Pro  Ala  Thr  Ala  Ile  Asn  Val  Thr  Thr  Asn  Ile  Ser
               580                      585                     590

Ala  Pro  Thr  Leu  Pro  Asp  Tyr  Glu  Gly  Val  Asp  Ala  Ser  Leu  Asn  Glu
```

-continued

|     |     |     | 595 |     |     |     | 600 |     |     |     | 605 |     |     |     |
|-----|-----|-----|-----|-----|-----|-----|-----|-----|-----|-----|-----|-----|-----|-----|
| Thr | Ala | Thr | Thr | Ile | Thr | Val | Leu | Leu | Arg | Pro | Ala | Gln | Ala | Lys | Gly |
|     | 610 |     |     |     |     | 615 |     |     |     |     | 620 |     |     |     |
| Ala | Pro | Ile | Ser | Ala | Tyr | Gln | Ile | Val | Val | Glu | Glu | Leu | His | Pro | His |
| 625 |     |     |     |     | 630 |     |     |     |     | 635 |     |     |     |     | 640 |
| Arg | Thr | Lys | Arg | Glu | Ala | Gly | Ala | Met | Glu | Cys | Tyr | Gln | Val | Pro | Val |
|     |     |     |     | 645 |     |     |     |     | 650 |     |     |     |     | 655 |     |
| Thr | Tyr | Gln | Asn | Ala | Met | Ser | Gly | Gly | Ala | Pro | Tyr | Tyr | Phe | Ala | Ala |
|     |     |     | 660 |     |     |     |     | 665 |     |     |     |     | 670 |     |     |
| Glu | Leu | Pro | Pro | Gly | Asn | Leu | Pro | Glu | Pro | Ala | Pro | Phe | Thr | Val | Gly |
|     |     | 675 |     |     |     |     | 680 |     |     |     |     | 685 |     |     |     |
| Asp | Asn | Arg | Thr | Tyr | Gln | Gly | Phe | Trp | Asn | Pro | Pro | Leu | Ala | Pro | Arg |
|     | 690 |     |     |     |     | 695 |     |     |     |     | 700 |     |     |     |     |
| Lys | Gly | Tyr | Asn | Ile | Tyr | Phe | Gln | Ala | Met | Ser | Ser | Val | Glu | Lys | Glu |
| 705 |     |     |     |     | 710 |     |     |     |     | 715 |     |     |     |     | 720 |
| Thr | Lys | Thr | Gln | Cys | Val | Arg | Ile | Ala | Thr | Lys | Ala | Ala | Thr | Glu |
|     |     |     |     | 725 |     |     |     |     | 730 |     |     |     |     | 735 |
| Pro | Glu | Val | Ile | Pro | Asp | Pro | Ala | Lys | Gln | Thr | Asp | Arg | Val | Val | Lys |
|     |     |     | 740 |     |     |     |     | 745 |     |     |     |     | 750 |     |     |
| Ile | Ala | Gly | Ile | Ser | Ala | Gly | Ile | Leu | Val | Phe | Ile | Leu | Leu | Leu | Leu |
|     |     | 755 |     |     |     |     | 760 |     |     |     |     | 765 |     |     |     |
| Val | Val | Ile | Leu | Ile | Val | Lys | Lys | Ser | Lys | Leu | Ala | Lys | Lys | Arg | Lys |
|     | 770 |     |     |     |     | 775 |     |     |     |     | 780 |     |     |     |     |
| Asp | Ala | Met | Gly | Asn | Thr | Arg | Gln | Glu | Met | Thr | His | Met | Val | Asn | Ala |
| 785 |     |     |     |     | 790 |     |     |     |     | 795 |     |     |     |     | 800 |
| Met | Asp | Arg | Ser | Tyr | Ala | Asp | Gln | Ser | Thr | Leu | His | Ala | Glu | Asp | Pro |
|     |     |     |     | 805 |     |     |     |     | 810 |     |     |     |     | 815 |     |
| Leu | Ser | Ile | Thr | Phe | Met | Asp | Gln | His | Asn | Phe | Ser | Pro | Arg | Tyr | Glu |
|     |     |     | 820 |     |     |     |     | 825 |     |     |     |     | 830 |     |     |
| Asn | His | Ser | Ala | Thr | Ala | Glu | Ser | Ser | Arg | Leu | Leu | Asp | Val | Pro | Arg |
|     |     | 835 |     |     |     |     | 840 |     |     |     |     | 845 |     |     |     |
| Tyr | Leu | Cys | Glu | Gly | Thr | Glu | Ser | Pro | Tyr | Gln | Thr | Gly | Gln | Leu | His |
|     | 850 |     |     |     |     | 855 |     |     |     |     | 860 |     |     |     |     |
| Pro | Ala | Ile | Arg | Val | Ala | Asp | Leu | Leu | Gln | His | Ile | Asn | Leu | Met | Lys |
| 865 |     |     |     |     | 870 |     |     |     |     | 875 |     |     |     |     | 880 |
| Thr | Ser | Asp | Ser | Tyr | Gly | Phe | Lys | Glu | Glu | Tyr | Glu | Ser | Phe | Phe | Glu |
|     |     |     |     | 885 |     |     |     |     | 890 |     |     |     |     | 895 |     |
| Gly | Gln | Ser | Ala | Ser | Trp | Asp | Val | Ala | Lys | Lys | Asp | Gln | Asn | Arg | Ala |
|     |     |     | 900 |     |     |     |     | 905 |     |     |     |     | 910 |     |     |
| Lys | Asn | Arg | Tyr | Gly | Asn | Ile | Ile | Ala | Tyr | Asp | His | Ser | Arg | Val | Ile |
|     |     | 915 |     |     |     |     | 920 |     |     |     |     | 925 |     |     |     |
| Leu | Gln | Pro | Val | Glu | Asp | Asp | Pro | Ser | Ser | Asp | Tyr | Ile | Asn | Ala | Asn |
|     | 930 |     |     |     |     | 935 |     |     |     |     | 940 |     |     |     |     |
| Tyr | Ile | Asp | Gly | Tyr | Gln | Arg | Pro | Ser | His | Tyr | Ile | Ala | Thr | Gln | Gly |
| 945 |     |     |     |     | 950 |     |     |     |     | 955 |     |     |     |     | 960 |
| Pro | Val | His | Glu | Thr | Val | Tyr | Asp | Phe | Trp | Arg | Met | Ile | Trp | Gln | Glu |
|     |     |     |     | 965 |     |     |     |     | 970 |     |     |     |     | 975 |     |
| Gln | Ser | Ala | Cys | Ile | Val | Met | Val | Thr | Asn | Leu | Val | Glu | Val | Gly | Arg |
|     |     |     | 980 |     |     |     |     | 985 |     |     |     |     | 990 |     |     |
| Val | Lys | Cys | Tyr | Lys | Tyr | Trp | Pro | Asp | Asp | Thr | Glu | Val | Tyr | Gly | Asp |
|     |     | 995 |     |     |     |     | 1000|     |     |     |     | 1005|     |     |     |
| Phe | Lys | Val | Thr | Cys | Val | Glu | Met | Glu | Pro | Leu | Ala | Glu | Tyr | Val | Val |
|     | 1010|     |     |     |     | 1015|     |     |     |     | 1020|     |     |     |     |

```
Arg  Thr  Phe  Thr  Leu  Glu  Arg  Arg  Gly  Tyr  Asn  Glu  Ile  Arg  Glu  Val
1025                 1030                 1035                      1040

Lys  Gln  Phe  His  Phe  Thr  Gly  Trp  Pro  Asp  His  Gly  Val  Pro  Tyr  His
                    1045                 1050                      1055

Ala  Thr  Gly  Leu  Leu  Ser  Phe  Ile  Arg  Arg  Val  Lys  Leu  Ser  Asn  Pro
               1060                 1065                      1070

Pro  Ser  Ala  Gly  Pro  Ile  Val  Val  His  Cys  Ser  Ala  Gly  Ala  Gly  Arg
               1075                 1080                      1085

Thr  Gly  Cys  Tyr  Ile  Val  Ile  Asp  Ile  Met  Leu  Asp  Met  Ala  Glu  Arg
               1090                 1095                      1100

Glu  Gly  Val  Val  Asp  Ile  Tyr  Asn  Cys  Val  Lys  Ala  Leu  Arg  Ser  Arg
1105                 1110                 1115                      1120

Arg  Ile  Asn  Met  Val  Gln  Thr  Glu  Glu  Gln  Tyr  Ile  Phe  Ile  His  Asp
                    1125                 1130                      1135

Ala  Ile  Leu  Glu  Ala  Cys  Leu  Cys  Gly  Glu  Thr  Ala  Ile  Pro  Val  Cys
                    1140                 1145                      1150

Glu  Phe  Lys  Ala  Ala  Tyr  Phe  Asp  Met  Ile  Arg  Ile  Asp  Ser  Gln  Thr
               1155                 1160                      1165

Asn  Ser  Ser  His  Leu  Lys  Asp  Glu  Phe  Gln  Thr  Leu  Asn  Ser  Val  Thr
               1170                 1175                      1180

Pro  Arg  Leu  Gln  Ala  Glu  Asp  Cys  Ser  Ile  Ala  Cys  Leu  Pro  Arg  Asn
1185                 1190                 1195                      1200

His  Asp  Lys  Asn  Arg  Phe  Met  Asp  Met  Leu  Pro  Pro  Asp  Arg  Cys  Leu
                    1205                 1210                      1215

Pro  Phe  Leu  Ile  Thr  Ile  Asp  Gly  Glu  Ser  Ser  Asn  Tyr  Ile  Asn  Ala
               1220                 1225                      1230

Ala  Leu  Met  Asp  Ser  Tyr  Arg  Gln  Pro  Ala  Ala  Phe  Ile  Val  Thr  Gln
               1235                 1240                      1245

Tyr  Pro  Leu  Pro  Asn  Thr  Val  Lys  Asp  Phe  Trp  Arg  Leu  Val  Tyr  Asp
1250                 1255                 1260

Tyr  Gly  Cys  Thr  Ser  Ile  Val  Met  Leu  Asn  Glu  Val  Asp  Leu  Ser  Gln
1265                 1270                 1275                      1280

Gly  Cys  Pro  Gln  Tyr  Trp  Pro  Glu  Glu  Gly  Met  Leu  Arg  Tyr  Gly  Pro
               1285                 1290                      1295

Ile  Gln  Val  Glu  Cys  Met  Ser  Cys  Ser  Met  Asp  Cys  Asp  Val  Ile  Asn
                    1300                 1305                      1310

Arg  Ile  Phe  Arg  Ile  Cys  Asn  Leu  Thr  Arg  Pro  Gln  Glu  Gly  Tyr  Leu
                    1315                 1320                      1325

Met  Val  Gln  Gln  Phe  Gln  Tyr  Leu  Gly  Trp  Ala  Ser  His  Arg  Glu  Val
               1330                 1335                      1340

Pro  Gly  Ser  Lys  Arg  Ser  Phe  Leu  Lys  Leu  Ile  Leu  Gln  Val  Glu  Lys
1345                 1350                 1355                      1360

Trp  Gln  Glu  Glu  Cys  Glu  Glu  Gly  Glu  Gly  Arg  Thr  Ile  Ile  His  Cys
                    1365                 1370                      1375

Leu  Asn  Gly  Gly  Gly  Arg  Ser  Gly  Met  Phe  Cys  Ala  Ile  Gly  Ile  Val
               1380                 1385                      1390

Val  Glu  Met  Val  Lys  Arg  Gln  Asn  Val  Val  Asp  Val  Phe  His  Ala  Val
               1395                 1400                      1405

Lys  Thr  Leu  Arg  Asn  Ser  Lys  Pro  Asn  Met  Val  Glu  Ala  Pro  Glu  Gln
               1410                 1415                      1420

Tyr  Arg  Phe  Cys  Tyr  Asp  Val  Ala  Leu  Glu  Tyr  Leu  Glu  Ser  Ser
1425                 1430                 1435
```

( 2 ) INFORMATION FOR SEQ ID NO:3:

( i ) SEQUENCE CHARACTERISTICS:
    ( A ) LENGTH: 4374 base pairs
    ( B ) TYPE: nucleic acid
    ( C ) STRANDEDNESS: double
    ( D ) TOPOLOGY: unknown ( i i ) MOLECULE TYPE: DNA (genomic)

( i x ) FEATURE:
    ( A ) NAME/KEY: CDS
    ( B ) LOCATION: 1..4371

( x i ) SEQUENCE DESCRIPTION: SEQ ID NO:3:

```
ATG GAT GTG GCG GCC GCT GCG TTG CCT GCT TTT GTA GCT CTC TGG CTT        48
Met Asp Val Ala Ala Ala Ala Leu Pro Ala Phe Val Ala Leu Trp Leu
 1               5                  10                  15

CTG TAC CCG TGG CCT CTC CTG GGG TCG GCC CTT GGC CAG TTC TCA GCA        96
Leu Tyr Pro Trp Pro Leu Leu Gly Ser Ala Leu Gly Gln Phe Ser Ala
             20                  25                  30

GGT GGC TGT ACT TTT GAT GAT GGG CCA GGG GCT TGT GAC TAC CAC CAG       144
Gly Gly Cys Thr Phe Asp Asp Gly Pro Gly Ala Cys Asp Tyr His Gln
         35                  40                  45

GAT TTA TAC GAT GAC TTT GAG TGG GTC CAT GTC AGT GCG CAG GAA CCT       192
Asp Leu Tyr Asp Asp Phe Glu Trp Val His Val Ser Ala Gln Glu Pro
     50                  55                  60

CAT TAC CTG CCC CCC GAA ATG CCT CAA GGT TCC TAT ATG GTT GTG GAC       240
His Tyr Leu Pro Pro Glu Met Pro Gln Gly Ser Tyr Met Val Val Asp
 65                  70                  75                  80

TCC TCA AAT CAT GAT CCT GGA GAA AAA GCC AGA CTT CAG CTG CCT ACC       288
Ser Ser Asn His Asp Pro Gly Glu Lys Ala Arg Leu Gln Leu Pro Thr
                 85                  90                  95

ATG AAG GAG AAT GAC ACC CAC TGC ATT GAT TTC AGT TAC CTG TTA TAT       336
Met Lys Glu Asn Asp Thr His Cys Ile Asp Phe Ser Tyr Leu Leu Tyr
            100                 105                 110

AGC CAG AAG GGG TTG AAC CCT GGC ACT TTG AAT ATC CTA GTT AGG GTG       384
Ser Gln Lys Gly Leu Asn Pro Gly Thr Leu Asn Ile Leu Val Arg Val
        115                 120                 125

AAT AAA GGA CCT CTT GCT AAT CCA ATT TGG AAT GTA ACT GGA TTC ACT       432
Asn Lys Gly Pro Leu Ala Asn Pro Ile Trp Asn Val Thr Gly Phe Thr
130                 135                 140

GGT CGT GAT TGG CTT CGG GCT GAA CTA GCT GTG AGC ACC TTT TGG CCC       480
Gly Arg Asp Trp Leu Arg Ala Glu Leu Ala Val Ser Thr Phe Trp Pro
145                 150                 155                 160

AAT GAA TAC CAG GTA ATA TTT GAA GCT GAA GTC TCA GGA GGG AGA AGT       528
Asn Glu Tyr Gln Val Ile Phe Glu Ala Glu Val Ser Gly Gly Arg Ser
                165                 170                 175

GGT TAT ATT GCC ATT GAT GAC ATC CAA GTC CTG AGT TAT CCT TGC GAT       576
Gly Tyr Ile Ala Ile Asp Asp Ile Gln Val Leu Ser Tyr Pro Cys Asp
            180                 185                 190

AAA TCT CCT CAT TTT CTC CGC CTT GGT GAT GTG GAG GTC AAT GCT GGG       624
Lys Ser Pro His Phe Leu Arg Leu Gly Asp Val Glu Val Asn Ala Gly
        195                 200                 205

CAG AAT GCT ACA TTT CAG TGC ATT GCT ACA GGG AGA GAT GCT GTG CAT       672
Gln Asn Ala Thr Phe Gln Cys Ile Ala Thr Gly Arg Asp Ala Val His
    210                 215                 220

AAC AAG TTA TGG CTG CAG AGA CGC AAT GGA GAA GAC ATA CCC GTA GCC       720
Asn Lys Leu Trp Leu Gln Arg Arg Asn Gly Glu Asp Ile Pro Val Ala
225                 230                 235                 240

CAG ACT AAG AAC ATA AAT CAC AGA AGA TTT GCT GCC TCT TTC AGA TTG       768
Gln Thr Lys Asn Ile Asn His Arg Arg Phe Ala Ala Ser Phe Arg Leu
                245                 250                 255

CAA GAA GTG ACA AAA ACT GAC CAG GAT TTG TAC CGC TGC GTA ACT CAG       816
```

|  |  |  |  |  |  |  |  |  |  |  |  |  |  |  |  |
|---|---|---|---|---|---|---|---|---|---|---|---|---|---|---|---|
| Gln | Glu | Val | Thr<br>260 | Lys | Thr | Asp | Gln<br>265 | Asp | Leu | Tyr | Arg | Cys<br>270 | Val | Thr | Gln |

| TCA | GAA | CGA | GGT | TCT | GGG | GTT | TCC | AAT | TTT | GCT | CAA | CTC | ATT | GTG | AGA | 864 |
|---|---|---|---|---|---|---|---|---|---|---|---|---|---|---|---|---|
| Ser | Glu | Arg<br>275 | Gly | Ser | Gly | Val | Ser<br>280 | Asn | Phe | Ala | Gln | Leu<br>285 | Ile | Val | Arg |  |

| GAA | CCA | CCT | AGA | CCC | ATT | GCT | CCT | CCC | CAG | CTG | CTT | GGT | GTT | GGG | CCT | 912 |
|---|---|---|---|---|---|---|---|---|---|---|---|---|---|---|---|---|
| Glu | Pro<br>290 | Pro | Arg | Pro | Ile<br>295 | Ala | Pro | Pro | Gln | Leu<br>300 | Leu | Gly | Val | Gly | Pro |  |

| ACT | TAC | TTG | CTG | ATC | CAA | CTA | AAT | GCC | AAC | TCT | ATT | ATT | GGC | GAT | GGC | 960 |
|---|---|---|---|---|---|---|---|---|---|---|---|---|---|---|---|---|
| Thr<br>305 | Tyr | Leu | Leu | Ile | Gln<br>310 | Leu | Asn | Ala | Asn | Ser<br>315 | Ile | Ile | Gly | Asp | Gly<br>320 |  |

| CCC | ATC | ATC | CTG | AAA | GAA | GTA | GAG | TAT | CGA | ATG | ACA | TCA | GGA | TCT | TGG | 1008 |
|---|---|---|---|---|---|---|---|---|---|---|---|---|---|---|---|---|
| Pro | Ile | Ile | Leu | Lys<br>325 | Glu | Val | Glu | Tyr | Arg<br>330 | Met | Thr | Ser | Gly | Ser<br>335 | Trp |  |

| ACA | GAA | ACC | CAT | GCA | GTC | AAC | GCA | CCA | ACA | TAT | AAG | TTG | TGG | CAT | TTA | 1056 |
|---|---|---|---|---|---|---|---|---|---|---|---|---|---|---|---|---|
| Thr | Glu | Thr | His<br>340 | Ala | Val | Asn | Ala | Pro<br>345 | Thr | Tyr | Lys | Leu | Trp<br>350 | His | Leu |  |

| GAC | CCA | GAT | ACA | GAA | TAC | GAG | ATC | CGC | GTC | CTG | CTT | ACC | AGA | CCT | GGC | 1104 |
|---|---|---|---|---|---|---|---|---|---|---|---|---|---|---|---|---|
| Asp | Pro | Asp<br>355 | Thr | Glu | Tyr | Glu | Ile<br>360 | Arg | Val | Leu | Leu | Thr<br>365 | Arg | Pro | Gly |  |

| GAA | GGG | GGA | ACT | GGG | CTG | CCA | GGA | CCA | CCA | CTG | ATC | ACT | AGA | ACG | AAG | 1152 |
|---|---|---|---|---|---|---|---|---|---|---|---|---|---|---|---|---|
| Glu | Gly<br>370 | Gly | Thr | Gly | Leu | Pro<br>375 | Gly | Pro | Pro | Leu | Ile<br>380 | Thr | Arg | Thr | Lys |  |

| TGT | GCA | GAA | CCT | ATG | CGG | ACA | CCA | AAG | ACT | TTA | AAG | ATT | GCT | GAA | ATC | 1200 |
|---|---|---|---|---|---|---|---|---|---|---|---|---|---|---|---|---|
| Cys<br>385 | Ala | Glu | Pro | Met | Arg<br>390 | Thr | Pro | Lys | Thr | Leu<br>395 | Lys | Ile | Ala | Glu | Ile<br>400 |  |

| CAG | GCA | AGG | CGC | ATT | GCA | GTG | GAC | TGG | GAG | TCC | TTG | GGC | TAC | AAC | ATC | 1248 |
|---|---|---|---|---|---|---|---|---|---|---|---|---|---|---|---|---|
| Gln | Ala | Arg | Arg | Ile<br>405 | Ala | Val | Asp | Trp | Glu<br>410 | Ser | Leu | Gly | Tyr | Asn<br>415 | Ile |  |

| ACT | CGT | TGC | CAC | ACT | TTC | AAC | GTC | ACT | ATC | TGC | TAC | CAT | TAC | TTC | CGT | 1296 |
|---|---|---|---|---|---|---|---|---|---|---|---|---|---|---|---|---|
| Thr | Arg | Cys | His<br>420 | Thr | Phe | Asn | Val | Thr<br>425 | Ile | Cys | Tyr | His | Tyr<br>430 | Phe | Arg |  |

| GGC | CAC | AAT | GAG | AGC | AGG | GCA | GAC | TGC | TTG | GAC | ATG | GAC | CCC | AAA | GCC | 1344 |
|---|---|---|---|---|---|---|---|---|---|---|---|---|---|---|---|---|
| Gly | His | Asn<br>435 | Glu | Ser | Arg | Ala | Asp<br>440 | Cys | Leu | Asp | Met | Asp<br>445 | Pro | Lys | Ala |  |

| CCT | CAG | CAT | GTT | GTG | AAC | CAT | CTG | CCA | CCT | TAC | ACA | AAT | GTC | AGC | CTC | 1392 |
|---|---|---|---|---|---|---|---|---|---|---|---|---|---|---|---|---|
| Pro | Gln | His<br>450 | Val | Val | Asn | His | Leu<br>455 | Pro | Pro | Tyr | Thr | Asn<br>460 | Val | Ser | Leu |  |

| AAG | ATG | ATC | CTA | ACC | AAC | CCA | GAG | GGA | AGG | AAG | GAG | AGC | GAA | GAG | ACA | 1440 |
|---|---|---|---|---|---|---|---|---|---|---|---|---|---|---|---|---|
| Lys<br>465 | Met | Ile | Leu | Thr | Asn<br>470 | Pro | Glu | Gly | Arg | Lys<br>475 | Glu | Ser | Glu | Glu | Thr<br>480 |  |

| ATC | ATC | CAA | ACT | GAT | GAA | GAT | GTG | CCC | GGG | CCT | GTG | CCA | GTC | AAA | TCC | 1488 |
|---|---|---|---|---|---|---|---|---|---|---|---|---|---|---|---|---|
| Ile | Ile | Gln | Thr | Asp<br>485 | Glu | Asp | Val | Pro | Gly<br>490 | Pro | Val | Pro | Val | Lys<br>495 | Ser |  |

| CTC | CAA | GGA | ACA | TCC | TTT | GAA | AAC | AAG | ATC | TTC | CTG | AAC | TGG | AAA | GAG | 1536 |
|---|---|---|---|---|---|---|---|---|---|---|---|---|---|---|---|---|
| Leu | Gln | Gly | Thr<br>500 | Ser | Phe | Glu | Asn | Lys<br>505 | Ile | Phe | Leu | Asn | Trp<br>510 | Lys | Glu |  |

| CCA | CTG | GAA | CCG | AAT | GGA | ATT | ATC | ACT | CAG | TAT | GAG | GTG | AGC | TAT | AGC | 1584 |
|---|---|---|---|---|---|---|---|---|---|---|---|---|---|---|---|---|
| Pro | Leu | Glu<br>515 | Pro | Asn | Gly | Ile | Ile<br>520 | Thr | Gln | Tyr | Glu | Val<br>525 | Ser | Tyr | Ser |  |

| AGC | ATA | AGA | TCA | TTT | GAC | CCT | GCT | GTT | CCA | GTG | GCT | GGG | CCC | CCA | CAG | 1632 |
|---|---|---|---|---|---|---|---|---|---|---|---|---|---|---|---|---|
| Ser | Ile<br>530 | Arg | Ser | Phe | Asp | Pro<br>535 | Ala | Val | Pro | Val | Ala<br>540 | Gly | Pro | Pro | Gln |  |

| ACT | GTA | TCA | AAT | TTA | TGG | AAT | AGT | ACA | CAC | GTA | TTT | ATG | CAT | CTT | | 1680 |
|---|---|---|---|---|---|---|---|---|---|---|---|---|---|---|---|---|
| Thr<br>545 | Val | Ser | Asn | Leu | Trp<br>550 | Asn | Ser | Thr | His<br>555 | His | Val | Phe | Met | His<br>560 | Leu |  |

| CAC | CCT | GGA | ACC | ACC | TAC | CAG | TTT | TTT | ATA | AGA | GCC | AGC | ACT | GTC | AAA | 1728 |
|---|---|---|---|---|---|---|---|---|---|---|---|---|---|---|---|---|
| His | Pro | Gly | Thr<br>565 | Thr | Tyr | Gln | Phe | Phe<br>570 | Ile | Arg | Ala | Ser | Thr<br>575 | Val | Lys |  |

| GGC | TTT | GGA | CCA | GCA | ACA | GCC | ATC | AAT | GTG | ACC | ACA | AAT | ATC | TCA | GCT | 1776 |

|  |  |  |  |  |  |  |  |  |  |  |  |  |  |  |  |
|---|---|---|---|---|---|---|---|---|---|---|---|---|---|---|---|
| Gly | Phe | Gly | Pro<br>580 | Ala | Thr | Ala | Ile | Asn<br>585 | Val | Thr | Thr | Asn | Ile<br>590 | Ser | Ala |

| CCA | AGC | TTA | CCT | GAC | TAT | GAA | GGA | GTT | GAT | GCC | TCT | CTG | AAT | GAA | ACT | 1824 |
|---|---|---|---|---|---|---|---|---|---|---|---|---|---|---|---|---|
| Pro | Ser<br>595 | Leu | Pro | Asp | Tyr | Glu | Gly<br>600 | Val | Asp | Ala | Ser | Leu<br>605 | Asn | Glu | Thr | |

| GCC | ACC | ACC | ATC | ACA | GTA | CTA | TTG | AGG | CCT | GCA | CAA | GCC | AAA | GGT | GCT | 1872 |
| Ala | Thr<br>610 | Thr | Ile | Thr | Val | Leu<br>615 | Leu | Arg | Pro | Ala | Gln<br>620 | Ala | Lys | Gly | Ala | |

| CCT | ATC | AGT | GCT | TAT | CAA | ATT | GTT | GTG | GAG | CAG | CTA | CAC | CCA | CAT | CGA | 1920 |
| Pro<br>625 | Ile | Ser | Ala | Tyr | Gln<br>630 | Ile | Val | Val | Glu | Gln<br>635 | Leu | His | Pro | His | Arg<br>640 | |

| ACG | AAG | CGT | GAA | GCA | GGG | GCC | ATG | GAA | TGC | TAC | CAG | GTA | CCG | GTT | ACA | 1968 |
| Thr | Lys | Arg | Glu | Ala<br>645 | Gly | Ala | Met | Glu | Cys<br>650 | Tyr | Gln | Val | Pro | Val<br>655 | Thr | |

| TAC | CAG | AAC | GCC | CTA | AGT | GGG | GGC | GCG | CCC | TAT | TAC | TTT | GCC | GCA | GAA | 2016 |
| Tyr | Gln | Asn | Ala<br>660 | Leu | Ser | Gly | Gly | Ala<br>665 | Pro | Tyr | Tyr | Phe | Ala<br>670 | Ala | Glu | |

| CTT | CCC | CCT | GGG | AAT | CTT | CCC | GAG | CCT | GCT | CCC | TTC | ACC | GTG | GGT | GAC | 2064 |
| Leu | Pro | Pro<br>675 | Gly | Asn | Leu | Pro | Glu<br>680 | Pro | Ala | Pro | Phe | Thr<br>685 | Val | Gly | Asp | |

| AAC | CGG | ACC | TAT | AAA | GGC | TTT | TGG | AAC | CCT | CCC | CTG | GCC | CCC | CGC | AAA | 2112 |
| Asn | Arg<br>690 | Thr | Tyr | Lys | Gly | Phe<br>695 | Trp | Asn | Pro | Pro | Leu<br>700 | Ala | Pro | Arg | Lys | |

| GGA | TAC | AAC | ATC | TAT | TTC | CAA | GCG | ATG | AGC | AGT | GTG | GAG | AAG | GAA | ACT | 2160 |
| Gly<br>705 | Tyr | Asn | Ile | Tyr | Phe<br>710 | Gln | Ala | Met | Ser | Ser<br>715 | Val | Glu | Lys | Glu | Thr<br>720 | |

| AAA | ACC | CAA | TGT | GTA | CGA | ATT | GCT | ACA | AAA | GCA | GCA | GCA | ACA | GAA | GAA | 2208 |
| Lys | Thr | Gln | Cys | Val<br>725 | Arg | Ile | Ala | Thr | Lys<br>730 | Ala | Ala | Ala | Thr | Glu<br>735 | Glu | |

| CCA | GAA | GTG | ATC | CCA | GAC | CCG | GCA | AAG | CAG | ACA | GAC | AGA | GTG | GTG | AAA | 2256 |
| Pro | Glu | Val | Ile<br>740 | Pro | Asp | Pro | Ala | Lys<br>745 | Gln | Thr | Asp | Arg | Val<br>750 | Val | Lys | |

| ATC | GCG | GGC | ATC | AGT | GCT | GGC | ATC | CTA | GTG | TTC | ATC | CTT | CTC | CTG | CTG | 2304 |
| Ile | Ala | Gly<br>755 | Ile | Ser | Ala | Gly | Ile<br>760 | Leu | Val | Phe | Ile | Leu<br>765 | Leu | Leu | Leu | |

| GTT | GTC | ATA | GTA | ATT | GTG | AAA | AAG | AGC | AAG | CTT | GCT | AAG | AAG | CGC | AAA | 2352 |
| Val | Val<br>770 | Ile | Val | Ile | Val | Lys<br>775 | Lys | Ser | Lys | Leu | Ala<br>780 | Lys | Lys | Arg | Lys | |

| GAT | GCA | ATG | GGG | AAC | ACA | CGT | CAG | GAG | ATG | ACC | CAC | ATG | GTG | AAT | GCT | 2400 |
| Asp | Ala | Met | Gly | Asn<br>790 | Thr | Arg | Gln | Glu | Met<br>795 | Thr | His | Met | Val | Asn<br>800 | Ala | |
| 785 | | | | | | | | | | | | | | | | |

| ATG | GAC | CGA | AGT | TAT | GCT | GAC | CAG | AGC | ACC | CTG | CAT | GCA | GAA | GAC | CCC | 2448 |
| Met | Asp | Arg | Ser | Tyr<br>805 | Ala | Asp | Gln | Ser | Thr<br>810 | Leu | His | Ala | Glu | Asp<br>815 | Pro | |

| CTT | TCC | CTC | ACC | TTC | ATG | GAC | CAA | CAT | AAC | TTC | AGT | CCA | AGA | TTG | CCC | 2496 |
| Leu | Ser | Leu | Thr<br>820 | Phe | Met | Asp | Gln | His<br>825 | Asn | Phe | Ser | Pro | Arg<br>830 | Leu | Pro | |

| AAT | GAT | CCA | CTT | GTG | CCG | ACT | GCC | GTG | TTA | GAT | GAG | AAC | CAC | AGT | GCC | 2544 |
| Asn | Asp | Pro<br>835 | Leu | Val | Pro | Thr | Ala<br>840 | Val | Leu | Asp | Glu | Asn<br>845 | His | Ser | Ala | |

| ACA | GCA | GAG | TCT | AGT | CGT | CTC | CTG | GAT | GTT | CCT | CGA | TAC | CTC | TGC | GAA | 2592 |
| Thr | Ala<br>850 | Glu | Ser | Ser | Arg | Leu<br>855 | Leu | Asp | Val | Pro | Arg<br>860 | Tyr | Leu | Cys | Glu | |

| GGG | ACA | GAG | TCC | CCT | TAT | CAG | ACA | GGA | CAG | CTG | CAC | CCA | GCC | ATC | AGG | 2640 |
| Gly | Thr | Glu | Ser | Pro<br>870 | Tyr | Gln | Thr | Gly | Gln<br>875 | Leu | His | Pro | Ala | Ile<br>880 | Arg | |
| 865 | | | | | | | | | | | | | | | | |

| GTG | GCC | GAC | TTA | CTG | CAG | CAC | ATT | AAC | CTC | ATG | AAG | ACA | TCA | GAC | AGC | 2688 |
| Val | Ala | Asp | Leu | Leu<br>885 | Gln | His | Ile | Asn | Leu<br>890 | Met | Lys | Thr | Ser | Asp<br>895 | Ser | |

| TAT | GGG | TTC | AAA | GAG | GAA | TAC | GAG | AGC | TTC | TTT | GAA | GGC | CAG | TCA | GCC | 2736 |

|     |     |     |     |     |     |     |     |     |     |     |     |     |     |     |      |
|-----|-----|-----|-----|-----|-----|-----|-----|-----|-----|-----|-----|-----|-----|-----|------|
| Tyr | Gly | Phe | Lys | Glu | Glu | Tyr | Glu | Ser | Phe | Phe | Glu | Gly | Gln | Ser | Ala  |
|     |     |     | 900 |     |     |     | 905 |     |     |     |     | 910 |     |     |      |
| TCT | TGG | GAT | GTG | GCT | AAA | AAG | GAT | CAA | AAC | AGA | GCA | AAG | AAC | CGA | TAC  | 2784 |
| Ser | Trp | Asp | Val | Ala | Lys | Lys | Asp | Gln | Asn | Arg | Ala | Lys | Asn | Arg | Tyr  |
|     |     | 915 |     |     |     | 920 |     |     |     |     | 925 |     |     |     |      |
| GGA | AAC | ATT | ATC | GCA | TAT | GAT | CAC | TCC | AGA | GTC | ATC | CTG | CAA | CCT | GTG  | 2832 |
| Gly | Asn | Ile | Ile | Ala | Tyr | Asp | His | Ser | Arg | Val | Ile | Leu | Gln | Pro | Val  |
|     | 930 |     |     |     |     | 935 |     |     |     |     | 940 |     |     |     |      |
| GAA | GAT | GAC | CCT | TCT | TCA | GAT | TAC | ATT | AAT | GCC | AAC | TAC | ATC | GAC | ATT  | 2880 |
| Glu | Asp | Asp | Pro | Ser | Ser | Asp | Tyr | Ile | Asn | Ala | Asn | Tyr | Ile | Asp | Ile  |
| 945 |     |     |     |     | 950 |     |     |     |     | 955 |     |     |     |     | 960  |
| TGG | CTG | TAC | AGG | GAT | GGC | TAC | CAG | AGA | CCA | AGC | CAC | TAC | ATT | GCA | ACT  | 2928 |
| Trp | Leu | Tyr | Arg | Asp | Gly | Tyr | Gln | Arg | Pro | Ser | His | Tyr | Ile | Ala | Thr  |
|     |     |     |     | 965 |     |     |     | 970 |     |     |     |     | 975 |     |      |
| CAA | GGC | CCA | GTT | CAT | GAA | ACC | GTA | TAT | GAT | TTT | TGG | AGG | ATG | GTG | TGG  | 2976 |
| Gln | Gly | Pro | Val | His | Glu | Thr | Val | Tyr | Asp | Phe | Trp | Arg | Met | Val | Trp  |
|     |     |     | 980 |     |     |     |     | 985 |     |     |     |     | 990 |     |      |
| CAA | GAG | CAG | TCT | GCC | TGT | ATT | GTG | ATG | GTC | ACT | AAT | TTA | GTG | GAA | GTT  | 3024 |
| Gln | Glu | Gln | Ser | Ala | Cys | Ile | Val | Met | Val | Thr | Asn | Leu | Val | Glu | Val  |
|     |     | 995 |     |     |     |     | 1000|     |     |     |     | 1005|     |     |      |
| GGC | CGG | GTG | AAA | TGC | TAT | AAA | TAT | TGG | CCT | GAT | GAT | ACT | GAG | GTT | TAT  | 3072 |
| Gly | Arg | Val | Lys | Cys | Tyr | Lys | Tyr | Trp | Pro | Asp | Asp | Thr | Glu | Val | Tyr  |
|     | 1010|     |     |     |     | 1015|     |     |     |     | 1020|     |     |     |      |
| GGT | GAC | TTC | AAA | GTC | ACC | TGC | GTA | GAA | ATG | GAG | CCA | CTT | GCT | GAG | TAT  | 3120 |
| Gly | Asp | Phe | Lys | Val | Thr | Cys | Val | Glu | Met | Glu | Pro | Leu | Ala | Glu | Tyr  |
| 1025|     |     |     |     | 1030|     |     |     |     | 1035|     |     |     |     | 1040 |
| GTC | GTT | AGG | ACA | TTC | ACC | TTG | GAA | AGG | AGG | GGC | TAT | AAT | GAA | ATC | CGT  | 3168 |
| Val | Val | Arg | Thr | Phe | Thr | Leu | Glu | Arg | Arg | Gly | Tyr | Asn | Glu | Ile | Arg  |
|     |     |     |     | 1045|     |     |     |     | 1050|     |     |     |     | 1055|      |
| GAA | GTC | AAA | CAG | TTC | CAC | TTC | ACT | GGC | TGG | CCT | GAC | CAT | GGT | GTT | CCA  | 3216 |
| Glu | Val | Lys | Gln | Phe | His | Phe | Thr | Gly | Trp | Pro | Asp | His | Gly | Val | Pro  |
|     |     |     | 1060|     |     |     |     | 1065|     |     |     |     | 1070|     |      |
| TAC | CAC | GCA | ACA | GGG | CTC | CTG | TCA | TTT | ATC | CGG | AGA | GTC | AAG | CTA | TCT  | 3264 |
| Tyr | His | Ala | Thr | Gly | Leu | Leu | Ser | Phe | Ile | Arg | Arg | Val | Lys | Leu | Ser  |
|     |     |     | 1075|     |     |     |     | 1080|     |     |     |     | 1085|     |      |
| AAC | CCT | CCC | AGT | GCT | GGG | CCC | ATT | GTC | GTA | CAC | TGC | AGT | GCT | GGT | GCT  | 3312 |
| Asn | Pro | Pro | Ser | Ala | Gly | Pro | Ile | Val | Val | His | Cys | Ser | Ala | Gly | Ala  |
|     |     | 1090|     |     |     |     | 1095|     |     |     |     | 1100|     |     |      |
| GGG | CGC | ACA | GGC | TGT | TAC | ATT | GTT | ATT | GAC | ATA | ATG | CTG | GAC | ATG | GCT  | 3360 |
| Gly | Arg | Thr | Gly | Cys | Tyr | Ile | Val | Ile | Asp | Ile | Met | Leu | Asp | Met | Ala  |
| 1105|     |     |     |     | 1110|     |     |     |     | 1115|     |     |     |     | 1120 |
| GAA | AGA | GAG | GGT | GTG | GTT | GAC | ATC | TAC | AAC | TGT | GTG | AAA | GCC | TTA | CGA  | 3408 |
| Glu | Arg | Glu | Gly | Val | Val | Asp | Ile | Tyr | Asn | Cys | Val | Lys | Ala | Leu | Arg  |
|     |     |     |     | 1125|     |     |     |     | 1130|     |     |     |     | 1135|      |
| TCT | CGG | CGC | ATT | AAT | ATG | GTA | CAG | ACA | GAG | GAA | CAG | TAC | ATT | TTT | ATT  | 3456 |
| Ser | Arg | Arg | Ile | Asn | Met | Val | Gln | Thr | Glu | Glu | Gln | Tyr | Ile | Phe | Ile  |
|     |     |     |     | 1140|     |     |     |     | 1145|     |     |     |     | 1150|      |
| CAT | GAT | GCC | ATT | TTA | GAA | GCC | TGC | TTA | TGT | GGA | GAA | ACT | GCC | ATC | CCT  | 3504 |
| His | Asp | Ala | Ile | Leu | Glu | Ala | Cys | Leu | Cys | Gly | Glu | Thr | Ala | Ile | Pro  |
|     |     |     | 1155|     |     |     |     | 1160|     |     |     |     | 1165|     |      |
| GTG | TGT | GAA | TTT | AAA | GCT | GCA | TAT | TTT | GAT | ATG | ATT | CGA | ATA | GAC | TCT  | 3552 |
| Val | Cys | Glu | Phe | Lys | Ala | Ala | Tyr | Phe | Asp | Met | Ile | Arg | Ile | Asp | Ser  |
|     |     | 1170|     |     |     |     | 1175|     |     |     |     | 1180|     |     |      |
| CAG | ACT | AAC | TCC | TCT | CAT | CTC | AAA | GAT | GAA | TTT | CAG | ACT | CTG | AAT | TCG  | 3600 |
| Gln | Thr | Asn | Ser | Ser | His | Leu | Lys | Asp | Glu | Phe | Gln | Thr | Leu | Asn | Ser  |
| 1185|     |     |     |     | 1190|     |     |     |     | 1195|     |     |     |     | 1200 |
| GTC | ACC | CCT | CGA | CTA | CAA | GCT | GAA | GAC | TGC | AGC | ATA | GCC | TGC | CTG | CCA  | 3648 |
| Val | Thr | Pro | Arg | Leu | Gln | Ala | Glu | Asp | Cys | Ser | Ile | Ala | Cys | Leu | Pro  |
|     |     |     |     | 1205|     |     |     |     | 1210|     |     |     |     | 1215|      |
| AGG | AAC | CAT | GAC | AAG | AAC | CGT | TTC | ATG | GAT | ATG | CTC | CCA | CCT | GAC | AGA  | 3696 |

```
Arg  Asn  His  Asp  Lys  Asn  Arg  Phe  Met  Asp  Met  Leu  Pro  Pro  Asp  Arg
          1220                    1225                    1230

TGT  CTG  CCT  TTT  TTA  ATT  ACA  ATT  GAT  GGG  GAG  AGC  AGT  AAC  TAC  ATC      3744
Cys  Leu  Pro  Phe  Leu  Ile  Thr  Ile  Asp  Gly  Glu  Ser  Ser  Asn  Tyr  Ile
          1235                    1240                    1245

AAT  GCT  GCT  CTT  ATG  GAT  AGC  TAT  AGG  CAG  CCA  GCA  GCT  TTC  ATC  GTC      3792
Asn  Ala  Ala  Leu  Met  Asp  Ser  Tyr  Arg  Gln  Pro  Ala  Ala  Phe  Ile  Val
          1250                    1255                    1260

ACA  CAA  TAC  CCA  CTG  CCA  AAC  ACT  GTG  AAA  GAC  TTC  TGG  AGA  TTA  GTA      3840
Thr  Gln  Tyr  Pro  Leu  Pro  Asn  Thr  Val  Lys  Asp  Phe  Trp  Arg  Leu  Val
1265                     1270                    1275                    1280

TAT  GAT  TAC  GGA  TGT  ACC  TCC  ATC  GTG  ATG  CTA  AAT  GAA  GTG  GAC  CTG      3888
Tyr  Asp  Tyr  Gly  Cys  Thr  Ser  Ile  Val  Met  Leu  Asn  Glu  Val  Asp  Leu
                    1285                    1290                    1295

TCT  CAG  GGC  TGC  CCA  CAG  TAC  TGG  CCA  GAA  GAA  GGA  ATG  CTG  CGA  TAT      3936
Ser  Gln  Gly  Cys  Pro  Gln  Tyr  Trp  Pro  Glu  Glu  Gly  Met  Leu  Arg  Tyr
                    1300                    1305                    1310

GGT  CCT  ATC  CAA  GTG  GAA  TGT  ATG  TCT  TGT  TCA  ATG  GAC  TGT  GAT  GTG      3984
Gly  Pro  Ile  Gln  Val  Glu  Cys  Met  Ser  Cys  Ser  Met  Asp  Cys  Asp  Val
          1315                    1320                    1325

ATC  AAT  CGA  ATT  TTT  AGA  ATA  TGC  AAC  CTA  ACG  AGA  CCA  CAG  GAG  GGC      4032
Ile  Asn  Arg  Ile  Phe  Arg  Ile  Cys  Asn  Leu  Thr  Arg  Pro  Gln  Glu  Gly
          1330                    1335                    1340

TAT  CTG  ATG  GTA  CAA  CAG  TTC  CAG  TAC  CTA  GGC  TGG  GCT  TCT  CAT  CGA      4080
Tyr  Leu  Met  Val  Gln  Gln  Phe  Gln  Tyr  Leu  Gly  Trp  Ala  Ser  His  Arg
1345                     1350                    1355                    1360

GAA  GTG  CCT  GGC  TCC  AAA  CGC  TCG  TTT  TTG  AAA  TTG  ATA  CTG  CAG  GTG      4128
Glu  Val  Pro  Gly  Ser  Lys  Arg  Ser  Phe  Leu  Lys  Leu  Ile  Leu  Gln  Val
                    1365                    1370                    1375

GAA  AAA  TGG  CAA  GAG  GAA  TGT  GAA  GAA  GGG  GAA  GGC  CGG  ACA  ATC  ATC      4176
Glu  Lys  Trp  Gln  Glu  Glu  Cys  Glu  Glu  Gly  Glu  Gly  Arg  Thr  Ile  Ile
                    1380                    1385                    1390

CAC  TGC  TTG  AAT  GGC  GGT  GGG  CGC  AGT  GGC  ATG  TTC  TGT  GCC  ATA  GGC      4224
His  Cys  Leu  Asn  Gly  Gly  Gly  Arg  Ser  Gly  Met  Phe  Cys  Ala  Ile  Gly
          1395                    1400                    1405

ATT  GTT  GTG  GAG  ATG  GTG  AAG  CGG  CAA  AAT  GTG  GTG  GAT  GTT  TTC  CAT      4272
Ile  Val  Val  Glu  Met  Val  Lys  Arg  Gln  Asn  Val  Val  Asp  Val  Phe  His
1410                     1415                    1420

GCA  GTA  AAG  ACG  CTG  AGG  AAC  AGC  AAG  CCA  AAC  ATG  GTG  GAA  GCC  CCG      4320
Ala  Val  Lys  Thr  Leu  Arg  Asn  Ser  Lys  Pro  Asn  Met  Val  Glu  Ala  Pro
1425                     1430                    1435                    1440

GAG  CAG  TAT  CGT  TTT  TGC  TAT  GAT  GTG  GCG  TTA  GAG  TAC  CTG  GAG  TCC      4368
Glu  Gln  Tyr  Arg  Phe  Cys  Tyr  Asp  Val  Ala  Leu  Glu  Tyr  Leu  Glu  Ser
                    1445                    1450                    1455

TCA  TAG                                                                              4374
Ser
```

(2) INFORMATION FOR SEQ ID NO:4:

(i) SEQUENCE CHARACTERISTICS:
        (A) LENGTH: 4651 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..4317

(xi) SEQUENCE DESCRIPTION: SEQ ID NO:4:

```
ATG  GAT  ACG  ACT  GCG  GCG  GCG  GCG  CTG  CCT  GCT  TTT  GTG  GCG  CTC  TTG       48
```

-continued

```
Met Asp Thr Thr Ala Ala Ala Ala Leu Pro Ala Phe Val Ala Leu Leu
 1               5                  10                  15

CTC CTC TCT CCT TGG CCT CTC CTG GGA TCG GCC CAA GGC CAG TTC TCC        96
Leu Leu Ser Pro Trp Pro Leu Leu Gly Ser Ala Gln Gly Gln Phe Ser
             20                  25                  30

GCA GGT GGC TGT ACT TTT GAT GAT GGT CCA GGG GCC TGT GAT TAC CAC       144
Ala Gly Gly Cys Thr Phe Asp Asp Gly Pro Gly Ala Cys Asp Tyr His
         35                  40                  45

CAG GAT CTG TAT GAT GAC TTT GAA TGG GTG CAT GTT AGT GCT CAA GAG       192
Gln Asp Leu Tyr Asp Asp Phe Glu Trp Val His Val Ser Ala Gln Glu
     50                  55                  60

CCT CAT TAT CTA CCA CCC GAG ATG CCC CAA GGT TCC TAT ATG ATA GTG       240
Pro His Tyr Leu Pro Pro Glu Met Pro Gln Gly Ser Tyr Met Ile Val
 65                  70                  75                  80

GAC TCT TCA GAT CAC GAC CCT GGA GAA AAA GCC AGA CTT CAG CTG CCT       288
Asp Ser Ser Asp His Asp Pro Gly Glu Lys Ala Arg Leu Gln Leu Pro
                 85                  90                  95

ACA ATG AAG GAG AAC GAC ACT CAC TGC ATT GAT TTC AGT TAC CTA TTA       336
Thr Met Lys Glu Asn Asp Thr His Cys Ile Asp Phe Ser Tyr Leu Leu
             100                 105                 110

TAT AGC CAG AAA GGA CTG AAT CCT GGC ACT TTG AAC ATA TTA GTT AGG       384
Tyr Ser Gln Lys Gly Leu Asn Pro Gly Thr Leu Asn Ile Leu Val Arg
         115                 120                 125

GTG AAT AAA GGA CCT CTT GCC AAT CCA ATT TGG AAT GTG ACT GGA TTC       432
Val Asn Lys Gly Pro Leu Ala Asn Pro Ile Trp Asn Val Thr Gly Phe
     130                 135                 140

ACG GGT AGA GAT TGG CTT CGG GCT GAG CTA GCA GTG AGC ACC TTT TGG       480
Thr Gly Arg Asp Trp Leu Arg Ala Glu Leu Ala Val Ser Thr Phe Trp
 145                 150                 155                 160

CCC AAT GAA TAT CAG GTA ATA TTT GAA GCT GAA GTC TCA GGA GGG AGA       528
Pro Asn Glu Tyr Gln Val Ile Phe Glu Ala Glu Val Ser Gly Gly Arg
                 165                 170                 175

AGT GGT TAT ATT GCC ATT GAT GAC ATC CAA GTA CTG AGT TAT CCT TGT       576
Ser Gly Tyr Ile Ala Ile Asp Asp Ile Gln Val Leu Ser Tyr Pro Cys
             180                 185                 190

GAT AAA TCT CCT CAT TTC CTC CGT CTA GGG GAT GTA GAG GTG AAT GCA       624
Asp Lys Ser Pro His Phe Leu Arg Leu Gly Asp Val Glu Val Asn Ala
         195                 200                 205

GGG CAA AAC GCT ACA TTT CAG TGC ATT GCC ACA GGG AGA GAT GCT GTG       672
Gly Gln Asn Ala Thr Phe Gln Cys Ile Ala Thr Gly Arg Asp Ala Val
     210                 215                 220

CAT AAC AAG TTA TGG CTC CAG AGA CGA AAT GGA GAA GAT ATA CCA GTA       720
His Asn Lys Leu Trp Leu Gln Arg Arg Asn Gly Glu Asp Ile Pro Val
 225                 230                 235                 240

GCC CAG ACT AAG AAC ATC AAT CAT AGA AGG TTT GCC GCT TCC TTC AGA       768
Ala Gln Thr Lys Asn Ile Asn His Arg Arg Phe Ala Ala Ser Phe Arg
                 245                 250                 255

TTG CAA GAA GTG ACA AAA ACT GAC CAG GAT TTG TAT CGC TGT GTA ACT       816
Leu Gln Glu Val Thr Lys Thr Asp Gln Asp Leu Tyr Arg Cys Val Thr
             260                 265                 270

CAG TCA GAA CGA GGT TCC GGT GTG TCC AAT TTT GCT CAA CTT ATT GTG       864
Gln Ser Glu Arg Gly Ser Gly Val Ser Asn Phe Ala Gln Leu Ile Val
         275                 280                 285

AGA GAA CCG CCA AGA CCC ATT GCT CCT CCT CAG CTT CTT GGT GTT GGG       912
Arg Glu Pro Pro Arg Pro Ile Ala Pro Pro Gln Leu Leu Gly Val Gly
     290                 295                 300

CCT ACA TAT TTG CTG ATC CAA CTA AAT GCC AAC TCG ATC ATT GGC GAT       960
Pro Thr Tyr Leu Leu Ile Gln Leu Asn Ala Asn Ser Ile Ile Gly Asp
 305                 310                 315                 320

GGT CCT ATC ATC CTG AAA GAA GTA GAG TAC CGA ATG ACA TCA GGA TCC      1008
```

```
                Gly  Pro  Ile  Ile  Leu  Lys  Glu  Val  Glu  Tyr  Arg  Met  Thr  Ser  Gly  Ser
                               325                      330                          335

TGG  ACA  GAA  ACC  CAT  GCA  GTC  AAT  GCT  CCA  ACT  TAC  AAA  TTA  TGG  CAT                    1056
Trp  Thr  Glu  Thr  His  Ala  Val  Asn  Ala  Pro  Thr  Tyr  Lys  Leu  Trp  His
               340                     345                          350

TTA  GAT  CCA  GAT  ACC  GAA  TAT  GAG  ATC  CGA  GTT  CTA  CTT  ACA  AGA  CCT                    1104
Leu  Asp  Pro  Asp  Thr  Glu  Tyr  Glu  Ile  Arg  Val  Leu  Leu  Thr  Arg  Pro
               355                     360                          365

GGT  GAA  GGT  GGA  ACG  GGG  CTC  CCA  GGA  CCT  CCA  CTA  ATC  ACC  AGA  ACA                    1152
Gly  Glu  Gly  Gly  Thr  Gly  Leu  Pro  Gly  Pro  Pro  Leu  Ile  Thr  Arg  Thr
               370                     375                          380

AAA  TGT  GCA  GAA  CCT  ATG  AGA  ACC  CCA  AAG  ACA  TTA  AAG  ATT  GCT  GAA                    1200
Lys  Cys  Ala  Glu  Pro  Met  Arg  Thr  Pro  Lys  Thr  Leu  Lys  Ile  Ala  Glu
385                      390                     395                          400

ATA  CAG  GCA  AGA  CGG  ATT  GCT  GTG  GAC  TGG  GAA  TCC  TTG  GGT  TAC  AAC                    1248
Ile  Gln  Ala  Arg  Arg  Ile  Ala  Val  Asp  Trp  Glu  Ser  Leu  Gly  Tyr  Asn
                    405                     410                          415

ATT  ACG  CGT  TGC  CAC  ACT  TTT  AAT  GTC  ACT  ATC  TGC  TAC  CAT  TAC  TTC                    1296
Ile  Thr  Arg  Cys  His  Thr  Phe  Asn  Val  Thr  Ile  Cys  Tyr  His  Tyr  Phe
                    420                     425                          430

CGT  GGT  CAC  AAC  GAG  AGC  AAG  GCA  GAC  TGT  TTG  GAC  ATG  GAC  CCC  AAA                    1344
Arg  Gly  His  Asn  Glu  Ser  Lys  Ala  Asp  Cys  Leu  Asp  Met  Asp  Pro  Lys
               435                     440                          445

GCC  CCT  CAG  CAT  GTT  GTG  AAC  CAT  CTG  CCA  CCT  TAT  ACA  AAT  GTC  AGC                    1392
Ala  Pro  Gln  His  Val  Val  Asn  His  Leu  Pro  Pro  Tyr  Thr  Asn  Val  Ser
          450                     455                     460

CTC  AAG  ATG  ATC  CTA  ACC  AAT  CCA  GAG  GGA  AGG  AAG  GAG  AGT  GAA  GAG                    1440
Leu  Lys  Met  Ile  Leu  Thr  Asn  Pro  Glu  Gly  Arg  Lys  Glu  Ser  Glu  Glu
465                      470                     475                          480

ACA  ATT  ATT  CAA  ACT  GAT  GAA  GAT  GTG  CCT  GGT  CCC  GTA  CCA  GTA  AAA                    1488
Thr  Ile  Ile  Gln  Thr  Asp  Glu  Asp  Val  Pro  Gly  Pro  Val  Pro  Val  Lys
                    485                     490                          495

TCT  CTT  CAA  GGA  ACA  TCC  TTT  GAA  AAT  AAG  ATC  TTC  TTG  AAC  TGG  AAA                    1536
Ser  Leu  Gln  Gly  Thr  Ser  Phe  Glu  Asn  Lys  Ile  Phe  Leu  Asn  Trp  Lys
               500                     505                          510

GAA  CCT  TTG  GAT  CCA  AAT  GGA  ATC  ATC  ACT  CAA  TAT  GAG  ATC  AGC  TAT                    1584
Glu  Pro  Leu  Asp  Pro  Asn  Gly  Ile  Ile  Thr  Gln  Tyr  Glu  Ile  Ser  Tyr
               515                     520                          525

AGC  AGT  ATA  AGA  TCA  TTT  GAT  CCT  GCA  GTC  CCA  GTG  GCT  GGA  CCT  CCC                    1632
Ser  Ser  Ile  Arg  Ser  Phe  Asp  Pro  Ala  Val  Pro  Val  Ala  Gly  Pro  Pro
530                      535                     540

CAG  ACT  GTA  TCA  AAT  TTA  TGG  AAC  AGT  ACA  CAC  CAT  GTC  TTT  ATG  CAT                    1680
Gln  Thr  Val  Ser  Asn  Leu  Trp  Asn  Ser  Thr  His  His  Val  Phe  Met  His
545                      550                     555                          560

CTC  CAC  CCT  GGA  ACC  ACG  TAC  CAG  TTT  TTC  ATA  AGA  GCC  AGC  ACG  GTC                    1728
Leu  His  Pro  Gly  Thr  Thr  Tyr  Gln  Phe  Phe  Ile  Arg  Ala  Ser  Thr  Val
               565                     570                          575

AAA  GGC  TTT  GGT  CCA  GCC  ACA  GCC  ATC  AAT  GTC  ACC  ACC  AAT  ATC  TCA                    1776
Lys  Gly  Phe  Gly  Pro  Ala  Thr  Ala  Ile  Asn  Val  Thr  Thr  Asn  Ile  Ser
               580                     585                          590

GCT  CCA  ACT  TTA  CCT  GAC  TAT  GAA  GGA  GTT  GAT  GCC  TCT  CTC  AAT  GAA                    1824
Ala  Pro  Thr  Leu  Pro  Asp  Tyr  Glu  Gly  Val  Asp  Ala  Ser  Leu  Asn  Glu
               595                     600                          605

ACT  GCC  ACC  ACA  ATA  ACT  GTA  TTG  TTG  AGA  CCA  GCA  CAA  GCC  AAA  GGT                    1872
Thr  Ala  Thr  Thr  Ile  Thr  Val  Leu  Leu  Arg  Pro  Ala  Gln  Ala  Lys  Gly
610                      615                     620

GCT  CCT  ATC  AGT  GCT  TAT  CAG  ATT  GTT  GTG  GAA  GAA  CTG  CAC  CCA  CAC                    1920
Ala  Pro  Ile  Ser  Ala  Tyr  Gln  Ile  Val  Val  Glu  Glu  Leu  His  Pro  His
625                      630                     635                          640

CGA  ACC  AAG  AGA  GAA  GCC  GGA  GCC  ATG  GAA  TGC  TAC  CAG  GTT  CCT  GTC                    1968
```

```
Arg  Thr  Lys  Arg  Glu  Ala  Gly  Ala  Met  Glu  Cys  Tyr  Gln  Val  Pro  Val
               645                      650                      655

ACA  TAC  CAA  AAT  GCC  ATG  AGT  GGG  GGT  GCA  CCG  TAT  TAC  TTT  GCT  GCA        2016
Thr  Tyr  Gln  Asn  Ala  Met  Ser  Gly  Gly  Ala  Pro  Tyr  Tyr  Phe  Ala  Ala
               660                      665                      670

GAA  CTA  CCC  CCG  GGA  AAC  CTA  CCT  GAG  CCT  GCC  CCG  TTC  ACT  GTG  GGT        2064
Glu  Leu  Pro  Pro  Gly  Asn  Leu  Pro  Glu  Pro  Ala  Pro  Phe  Thr  Val  Gly
               675                      680                      685

GAC  AAT  CGG  ACC  TAC  CAA  GGC  TTT  TGG  AAC  CCT  CCT  TTG  GCT  CCG  CGC        2112
Asp  Asn  Arg  Thr  Tyr  Gln  Gly  Phe  Trp  Asn  Pro  Pro  Leu  Ala  Pro  Arg
               690                      695                      700

AAA  GGA  TAC  AAC  ATC  TAT  TTC  CAG  GCG  ATG  AGC  AGT  GTG  GAG  AAG  GAA        2160
Lys  Gly  Tyr  Asn  Ile  Tyr  Phe  Gln  Ala  Met  Ser  Ser  Val  Glu  Lys  Glu
705            710                      715                      720

ACT  AAA  ACC  CAG  TGC  GTA  CGC  ATT  GCT  ACA  AAA  GCA  GCA  ACA  GAA  GAA        2208
Thr  Lys  Thr  Gln  Cys  Val  Arg  Ile  Ala  Thr  Lys  Ala  Ala  Thr  Glu  Glu
               725                      730                      735

CCA  GAA  GTG  ATC  CCA  GAT  CCC  GCC  AAG  CAG  ACA  GAC  AGA  GTG  GTG  AAA        2256
Pro  Glu  Val  Ile  Pro  Asp  Pro  Ala  Lys  Gln  Thr  Asp  Arg  Val  Val  Lys
               740                      745                      750

ATA  GCA  GGA  ATT  AGT  GCT  GGA  ATT  TTG  GTG  TTC  ATC  CTC  CTT  CTC  CTA        2304
Ile  Ala  Gly  Ile  Ser  Ala  Gly  Ile  Leu  Val  Phe  Ile  Leu  Leu  Leu  Leu
755            760                      765

GTT  GTC  ATA  TTA  ATT  GTA  AAA  AAG  AGC  AAA  CTT  GCT  AAA  AAA  CGC  AAA        2352
Val  Val  Ile  Leu  Ile  Val  Lys  Lys  Ser  Lys  Leu  Ala  Lys  Lys  Arg  Lys
770            775                      780

GAT  GCC  ATG  GGG  AAT  ACC  CGG  CAG  GAG  ATG  ACT  CAC  ATG  GTG  AAT  GCA        2400
Asp  Ala  Met  Gly  Asn  Thr  Arg  Gln  Glu  Met  Thr  His  Met  Val  Asn  Ala
785                 790                      795                      800

ATG  GAT  CGA  AGT  TAT  GCT  GAT  CAG  AGC  ACT  CTG  CAT  GCA  GAA  GAT  CCT        2448
Met  Asp  Arg  Ser  Tyr  Ala  Asp  Gln  Ser  Thr  Leu  His  Ala  Glu  Asp  Pro
               805                      810                      815

CTT  TCC  ATC  ACC  TTC  ATG  GAC  CAA  CAT  AAC  TTT  AGT  CCA  AGA  TAT  GAG        2496
Leu  Ser  Ile  Thr  Phe  Met  Asp  Gln  His  Asn  Phe  Ser  Pro  Arg  Tyr  Glu
               820                      825                      830

AAC  CAC  AGT  GCT  ACA  GCA  GAG  TCC  AGT  CGC  CTT  CTA  GAC  GTA  CCT  CGC        2544
Asn  His  Ser  Ala  Thr  Ala  Glu  Ser  Ser  Arg  Leu  Leu  Asp  Val  Pro  Arg
               835                      840                      845

TAC  CTC  TGT  GAG  GGG  ACG  GAA  TCC  CCT  TAC  CAG  ACA  GGA  CAG  CTG  CAT        2592
Tyr  Leu  Cys  Glu  Gly  Thr  Glu  Ser  Pro  Tyr  Gln  Thr  Gly  Gln  Leu  His
850                      855                      860

CCA  GCC  ATC  AGG  GTA  GCT  GAT  TTA  CTG  CAG  CAC  ATT  AAT  CTC  ATG  AAG        2640
Pro  Ala  Ile  Arg  Val  Ala  Asp  Leu  Leu  Gln  His  Ile  Asn  Leu  Met  Lys
865                      870                      875                      880

ACA  TCA  GAC  AGC  TAT  GGG  TTC  AAA  GAG  GAA  TAT  GAG  AGC  TTT  TTT  GAA        2688
Thr  Ser  Asp  Ser  Tyr  Gly  Phe  Lys  Glu  Glu  Tyr  Glu  Ser  Phe  Phe  Glu
               885                      890                      895

GGA  CAG  TCA  GCA  TCT  TGG  GAT  GTA  GCT  AAA  AAA  GAT  CAA  AAT  AGA  GCA        2736
Gly  Gln  Ser  Ala  Ser  Trp  Asp  Val  Ala  Lys  Lys  Asp  Gln  Asn  Arg  Ala
               900                      905                      910

AAA  AAC  CGA  TAT  GGA  AAC  ATT  ATA  GCA  TAT  GAT  CAC  TCC  AGA  GTG  ATT        2784
Lys  Asn  Arg  Tyr  Gly  Asn  Ile  Ile  Ala  Tyr  Asp  His  Ser  Arg  Val  Ile
               915                      920                      925

TTG  CAA  CCC  GTA  GAG  GAT  GAT  CCT  TCC  TCA  GAT  TAT  ATT  AAT  GCC  AAC        2832
Leu  Gln  Pro  Val  Glu  Asp  Asp  Pro  Ser  Ser  Asp  Tyr  Ile  Asn  Ala  Asn
930                      935                      940

TAT  ATT  GAT  GGC  TAC  CAG  AGA  CCA  AGT  CAT  TAC  ATT  GCA  ACC  CAA  GGT        2880
Tyr  Ile  Asp  Gly  Tyr  Gln  Arg  Pro  Ser  His  Tyr  Ile  Ala  Thr  Gln  Gly
945            950                      955                      960

CCC  GTT  CAT  GAA  ACA  GTG  TAT  GAT  TTC  TGG  AGG  ATG  ATT  TGG  CAA  GAA        2928
```

```
Pro Val His Glu Thr Val Tyr Asp Phe Trp Arg Met Ile Trp Gln Glu
            965                 970                 975

CAA TCT GCT TGC ATT GTG ATG GTT ACA AAT TTA GTT GAG GTT GGC CGG    2976
Gln Ser Ala Cys Ile Val Met Val Thr Asn Leu Val Glu Val Gly Arg
            980                 985                 990

GTT AAA TGC TAT AAA TAT TGG CCT GAT GAT ACT GAA GTT TAT GGT GAC    3024
Val Lys Cys Tyr Lys Tyr Trp Pro Asp Asp Thr Glu Val Tyr Gly Asp
            995                 1000                1005

TTC AAA GTA ACG TGT GTA GAA ATG GAA CCA CTT GCT GAA TAT GTA GTT    3072
Phe Lys Val Thr Cys Val Glu Met Glu Pro Leu Ala Glu Tyr Val Val
    1010                1015                1020

AGG ACA TTC ACC CTG GAA AGG AGG GGG TAC AAT GAA ATC CGT GAA GTT    3120
Arg Thr Phe Thr Leu Glu Arg Arg Gly Tyr Asn Glu Ile Arg Glu Val
1025                1030                1035                1040

AAA CAG TTC CAT TTC ACG GGC TGG CCT GAC CAT GGA GTG CCC TAC CAT    3168
Lys Gln Phe His Phe Thr Gly Trp Pro Asp His Gly Val Pro Tyr His
                1045                1050                1055

GCT ACA GGG CTG CTT TCC TTT ATC CGG CGA GTC AAG TTA TCA AAC CCT    3216
Ala Thr Gly Leu Leu Ser Phe Ile Arg Arg Val Lys Leu Ser Asn Pro
            1060                1065                1070

CCC AGT GCT GGC CCC ATC GTT GTA CAT TGC AGT GCT GGT GCT GGA CGA    3264
Pro Ser Ala Gly Pro Ile Val Val His Cys Ser Ala Gly Ala Gly Arg
            1075                1080                1085

ACT GGC TGC TAC ATT GTG ATT GAC ATC ATG CTA GAC ATG GCT GAA AGA    3312
Thr Gly Cys Tyr Ile Val Ile Asp Ile Met Leu Asp Met Ala Glu Arg
    1090                1095                1100

GAG GGT GTT GTT GAT ATT TAC AAT TGT GTC AAA GCC TTA AGA TCT CGG    3360
Glu Gly Val Val Asp Ile Tyr Asn Cys Val Lys Ala Leu Arg Ser Arg
1105                1110                1115                1120

CGT ATT AAT ATG GTC CAG ACA GAG GAA CAG TAC ATT TTT ATT CAT GAT    3408
Arg Ile Asn Met Val Gln Thr Glu Glu Gln Tyr Ile Phe Ile His Asp
                1125                1130                1135

GCC ATT TTA GAA GCC TGC TTA TGT GGA GAA ACT GCC ATA CCT GTC TGT    3456
Ala Ile Leu Glu Ala Cys Leu Cys Gly Glu Thr Ala Ile Pro Val Cys
            1140                1145                1150

GAA TTT AAA GCT GCA TAT TTT GAT ATG ATT AGA ATA GAC TCC AGA ACT    3504
Glu Phe Lys Ala Ala Tyr Phe Asp Met Ile Arg Ile Asp Ser Gln Thr
            1155                1160                1165

AAC TCT TCA CAT CTC AAG GAT GAA TTT CAG ACT CTG AAT TCA GTC ACC    3552
Asn Ser Ser His Leu Lys Asp Glu Phe Gln Thr Leu Asn Ser Val Thr
    1170                1175                1180

CCT CGA CTA CAA GCT GAA GAC TGC AGT ATA GCG TGC CTG CCA AGG AAC    3600
Pro Arg Leu Gln Ala Glu Asp Cys Ser Ile Ala Cys Leu Pro Arg Asn
1185                1190                1195                1200

CAT GAC AAG AAC CGT TTC ATG GAC ATG CTG CCA CCT GAC AGA TGT CTG    3648
His Asp Lys Asn Arg Phe Met Asp Met Leu Pro Pro Asp Arg Cys Leu
                1205                1210                1215

CCT TTT TTA ATT ACA ATT GAT GGG GAG AGC AGT AAC TAC ATC AAT GCT    3696
Pro Phe Leu Ile Thr Ile Asp Gly Glu Ser Ser Asn Tyr Ile Asn Ala
            1220                1225                1230

GCT CTT ATG GAC AGC TAC AGG CAA CCA GCT GCT TTC ATC GTC ACA CAA    3744
Ala Leu Met Asp Ser Tyr Arg Gln Pro Ala Ala Phe Ile Val Thr Gln
            1235                1240                1245

TAC CCT CTG CCA AAC ACT GTA AAA GAC TTC TGG AGA TTA GTG TAT GAT    3792
Tyr Pro Leu Pro Asn Thr Val Lys Asp Phe Trp Arg Leu Val Tyr Asp
1250                1255                1260

TAT GGC TGT ACC TCC ATT GTG ATG TTA AAC GAA GTC GAC TTG TCC CAG    3840
Tyr Gly Cys Thr Ser Ile Val Met Leu Asn Glu Val Asp Leu Ser Gln
1265                1270                1275                1280

GGC TGC CCT CAG TAC TGG CCA GAG GAA GGG ATG CTA CGA TAT GGC CCC    3888
```

|  |  |  |  |  |  |  |  |  |  |  |  |  |  |  |  |
|---|---|---|---|---|---|---|---|---|---|---|---|---|---|---|---|
| Gly | Cys | Pro | Gln | Tyr | Trp | Pro | Glu | Glu | Gly | Met | Leu | Arg | Tyr | Gly | Pro |
|  |  |  |  | 1285 |  |  |  | 1290 |  |  |  |  | 1295 |  |  |

| ATC | CAA | GTG | GAA | TGT | ATG | TCT | TGT | TCA | ATG | GAC | TGT | GAT | GTG | ATC | AAC | 3936 |
|---|---|---|---|---|---|---|---|---|---|---|---|---|---|---|---|---|
| Ile | Gln | Val | Glu | Cys | Met | Ser | Cys | Ser | Met | Asp | Cys | Asp | Val | Ile | Asn |  |
|  |  |  | 1300 |  |  |  |  | 1305 |  |  |  |  | 1310 |  |  |  |

| CGG | ATT | TTT | AGG | ATA | TGC | AAT | CTA | ACA | AGA | CCA | CAG | GAA | GGT | TAT | CTG | 3984 |
|---|---|---|---|---|---|---|---|---|---|---|---|---|---|---|---|---|
| Arg | Ile | Phe | Arg | Ile | Cys | Asn | Leu | Thr | Arg | Pro | Gln | Glu | Gly | Tyr | Leu |  |
|  |  |  | 1315 |  |  |  |  | 1320 |  |  |  |  | 1325 |  |  |  |

| ATG | GTG | CAA | CAG | TTT | CAG | TAC | CTA | GGA | TGG | GCT | TCT | CAT | CGA | GAA | GTG | 4032 |
|---|---|---|---|---|---|---|---|---|---|---|---|---|---|---|---|---|
| Met | Val | Gln | Gln | Phe | Gln | Tyr | Leu | Gly | Trp | Ala | Ser | His | Arg | Glu | Val |  |
|  |  | 1330 |  |  |  |  | 1335 |  |  |  |  | 1340 |  |  |  |  |

| CCT | GGA | TCC | AAA | AGG | TCA | TTC | TTG | AAA | CTG | ATA | CTT | CAG | GTG | GAA | AAG | 4080 |
|---|---|---|---|---|---|---|---|---|---|---|---|---|---|---|---|---|
| Pro | Gly | Ser | Lys | Arg | Ser | Phe | Leu | Lys | Leu | Ile | Leu | Gln | Val | Glu | Lys |  |
| 1345 |  |  |  |  | 1350 |  |  |  |  | 1355 |  |  |  |  | 1360 |  |

| TGG | CAG | GAG | GAA | TGC | GAG | GAA | GGG | GAA | GGC | CGG | ACG | ATT | ATC | CAC | TGC | 4128 |
|---|---|---|---|---|---|---|---|---|---|---|---|---|---|---|---|---|
| Trp | Gln | Glu | Glu | Cys | Glu | Glu | Gly | Glu | Gly | Arg | Thr | Ile | Ile | His | Cys |  |
|  |  |  |  | 1365 |  |  |  |  | 1370 |  |  |  |  | 1375 |  |  |

| CTA | AAT | GGT | GGC | GGG | CGA | AGT | GGC | ATG | TTC | TGT | GCT | ATA | GGC | ATC | GTT | 4176 |
|---|---|---|---|---|---|---|---|---|---|---|---|---|---|---|---|---|
| Leu | Asn | Gly | Gly | Gly | Arg | Ser | Gly | Met | Phe | Cys | Ala | Ile | Gly | Ile | Val |  |
|  |  |  | 1380 |  |  |  |  | 1385 |  |  |  |  | 1390 |  |  |  |

| GTT | GAA | ATG | GTG | AAA | CGG | CAA | AAT | GTT | GTC | GAT | GTT | TTC | CAT | GCA | GTA | 4224 |
|---|---|---|---|---|---|---|---|---|---|---|---|---|---|---|---|---|
| Val | Glu | Met | Val | Lys | Arg | Gln | Asn | Val | Val | Asp | Val | Phe | His | Ala | Val |  |
|  |  |  | 1395 |  |  |  |  | 1400 |  |  |  |  | 1405 |  |  |  |

| AAG | ACA | CTG | AGG | AAC | AGC | AAG | CCA | AAC | ATG | GTG | GAA | GCC | CCG | GAG | CAA | 4272 |
|---|---|---|---|---|---|---|---|---|---|---|---|---|---|---|---|---|
| Lys | Thr | Leu | Arg | Asn | Ser | Lys | Pro | Asn | Met | Val | Glu | Ala | Pro | Glu | Gln |  |
| 1410 |  |  |  |  | 1415 |  |  |  |  | 1420 |  |  |  |  |  |  |

| TAC | CGT | TTC | TGC | TAT | GAT | GTA | GCT | TTG | GAG | TAC | CTG | GAA | TCA | TCT |  | 4317 |
|---|---|---|---|---|---|---|---|---|---|---|---|---|---|---|---|---|
| Tyr | Arg | Phe | Cys | Tyr | Asp | Val | Ala | Leu | Glu | Tyr | Leu | Glu | Ser | Ser |  |  |
| 1425 |  |  |  | 1430 |  |  |  |  | 1435 |  |  |  |  |  |  |  |

| TAGTTGGGTG | AGACTCTTTA | AAGTGCATCC | ATGAAGAAAC | CTGTCCATCT | ATTGAGCCAG | 4377 |
|---|---|---|---|---|---|---|
| CAGCTGTTGT | ACCTGTTACA | CTTGTGCAGA | AAGATTTTAA | TGTGGGGGGT | GGGAGACTTT | 4437 |
| TACATTTGAG | AGGTAAAAGT | ATTTTTTTA | TGAAGTTGTG | TATCTTAATA | AAAAGAACTG | 4497 |
| AATTAGTTTT | TATTACTATA | TTAAAGCATC | AACATTTCAT | GCCACATAAA | ATTATATTTA | 4557 |
| ATAAGAACCA | GATTGAAATG | AGAACGTATT | GGTGTTTGTA | CAGTGAACAT | GCCACCTTTT | 4617 |
| TCCATGGTTT | CAGGTAGTGC | AGCTACCACA | TGTT |  |  | 4651 |

(2) INFORMATION FOR SEQ ID NO:5:

(i) SEQUENCE CHARACTERISTICS:
        (A) LENGTH: 78 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:5:

|  |  |  |  |  |  |  |  |  |  |  |  |  |  |  |  |
|---|---|---|---|---|---|---|---|---|---|---|---|---|---|---|---|
| Pro | Pro | Thr | Asn | Leu | His | Leu | Glu | Ala | Asn | Pro | Asp | Thr | Gly | Val | Leu |
| 1 |  |  |  | 5 |  |  |  |  | 10 |  |  |  |  | 15 |  |
| Thr | Val | Ser | Trp | Glu | Arg | Ser | Thr | Thr | Pro | Asp | Ile | Thr | Gly | Tyr | Arg |
|  |  |  | 20 |  |  |  |  | 25 |  |  |  |  | 30 |  |  |
| Ile | Thr | Thr | Thr | Pro | Thr | Asn | Gly | Gln | Gln | Gly | Asn | Ser | Leu | Glu | Glu |
|  |  |  | 35 |  |  |  |  | 40 |  |  |  |  | 45 |  |  |
| Val | Val | His | Ala | Asp | Gln | Ser | Ser | Cys | Thr | Phe | Asp | Asn | Leu | Ser | Pro |
|  |  | 50 |  |  |  |  | 55 |  |  |  |  | 60 |  |  |  |
| Gly | Leu | Glu | Tyr | Asn | Val | Ser | Val | Tyr | Thr | Val | Lys | Asp | Asp |  |  |
| 65 |  |  |  | 70 |  |  |  |  | 75 |  |  |  |  |  |  |

(2) INFORMATION FOR SEQ ID NO:6:

(i) SEQUENCE CHARACTERISTICS:
        (A) LENGTH: 156 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:6:

```
Gly Gly Cys Leu Phe Asp Glu Pro Tyr Ser Thr Cys Gly Tyr Ser Gln
 1               5                  10                      15

Ala Asp Glu Asp Asp Phe Asn Trp Glu Gln Val Asn Thr Leu Thr Lys
             20                  25                  30

Pro Thr Ser Asp Pro Trp Met Pro Ser Gly Ser Phe Met Leu Val Asn
             35                  40                  45

Thr Ser Gly Lys Pro Glu Gly Gln Arg Ala His Leu Leu Leu Pro Gln
         50                  55                  60

Leu Lys Glu Asn Asp Thr His Cys Ile Asp Phe His Tyr Phe Val Ser
 65                  70                  75                  80

Ser Lys Ser Asn Ala Ala Pro Gly Leu Leu Asn Val Tyr Val Lys Val
                 85                  90                  95

Asn Asn Gly Pro Leu Gly Asn Pro Ile Trp Asn Ile Ser Gly Asp Pro
             100                 105                 110

Thr Arg Thr Trp His Arg Ala Glu Leu Ala Ile Ser Thr Phe Trp Pro
             115                 120                 125

Asn Phe Tyr Gln Val Ile Phe Glu Val Val Thr Ser Gly His Gln Gly
             130                 135                 140

Tyr Leu Ala Ile Asp Glu Val Lys Val Leu Gly His
145                 150                 155
```

(2) INFORMATION FOR SEQ ID NO:7:

(i) SEQUENCE CHARACTERISTICS:
        (A) LENGTH: 154 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:7:

```
Cys Lys Phe Gly Trp Gly Ser Gln Lys Thr Val Cys Asn Trp Gln His
 1               5                  10                      15

Asp Ile Ser Ser Asp Leu Lys Trp Ala Val Leu Asn Ser Lys Thr Gly
             20                  25                  30

Pro Val Gln Asp His Thr Gly Asp Gly Asn Phe Ile Tyr Ser Glu Ala
             35                  40                  45

Asp Glu Arg His Glu Gly Arg Ala Ala Arg Leu Met Ser Pro Val Val
         50                  55                  60

Ser Ser Ser Arg Ser Ala His Cys Leu Thr Phe Trp Tyr His Met Asp
 65                  70                  75                  80

Gly Ser His Val Gly Thr Leu Ser Ile Lys Leu Lys Tyr Glu Met Glu
                 85                  90                  95

Glu Asp Phe Asp Gln Thr Leu Trp Thr Val Ser Gly Asn Gln Gly Asp
             100                 105                 110

Gln Trp Lys Glu Ala Arg Val Val Leu His Lys Thr Met Lys Gln Tyr
             115                 120                 125

Gln Val Ile Val Glu Gly Thr Val Gly Lys Gly Ser Ala Gly Gly Ile
```

130                         135                         140

Ala   Val   Asp   Asp   Ile   Ile   Ile   Ala   Asn   His
145                           150

( 2 ) INFORMATION FOR SEQ ID NO:8:

( i ) SEQUENCE CHARACTERISTICS:
        ( A ) LENGTH: 1452 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:8:

Met   Arg   Thr   Leu   Gly   Thr   Cys   Leu   Ala   Thr   Leu   Ala   Gly   Leu   Leu   Leu
1                       5                           10                          15

Thr   Ala   Ala   Gly   Glu   Thr   Phe   Ser   Gly   Cys   Leu   Phe   Asp   Glu   Pro
                  20                        25                        30

Tyr   Ser   Thr   Cys   Gly   Tyr   Ser   Gln   Ser   Glu   Gly   Asp   Asp   Phe   Asn   Trp
            35                        40                        45

Glu   Gln   Val   Asn   Thr   Leu   Thr   Lys   Pro   Thr   Ser   Asp   Pro   Trp   Met   Pro
      50                        55                        60

Ser   Gly   Ser   Leu   Met   Leu   Val   Asn   Ala   Ser   Gly   Arg   Pro   Glu   Gly   Gln
65                        70                        75                              80

Arg   Ala   His   Leu   Leu   Leu   Pro   Gln   Leu   Lys   Glu   Asn   Asp   Thr   His   Cys
                        85                        90                        95

Ile   Asp   Phe   His   Tyr   Phe   Val   Ser   Ser   Lys   Ser   Asn   Ser   Pro   Pro   Gly
                  100                       105                       110

Leu   Leu   Asn   Val   Tyr   Val   Lys   Val   Asn   Asn   Gly   Pro   Leu   Gly   Asn   Pro
            115                       120                       125

Ile   Trp   Asn   Ile   Ser   Gly   Asp   Pro   Thr   Arg   Thr   Trp   Asn   Arg   Ala   Glu
      130                       135                       140

Leu   Ala   Ile   Ser   Thr   Phe   Trp   Pro   Asn   Phe   Tyr   Gln   Val   Ile   Phe   Glu
145                       150                       155                             160

Val   Ile   Thr   Ser   Gly   His   Gln   Gly   Tyr   Leu   Ala   Ile   Asp   Glu   Val   Lys
                        165                       170                       175

Val   Leu   Gly   His   Pro   Cys   Thr   Arg   Thr   Pro   His   Phe   Leu   Arg   Ile   Gln
                  180                       185                       190

Asn   Val   Glu   Val   Asn   Ala   Gly   Gln   Phe   Ala   Thr   Phe   Gln   Cys   Ser   Ala
            195                       200                       205

Ile   Gly   Arg   Thr   Val   Ala   Gly   Asp   Arg   Leu   Trp   Leu   Gln   Gly   Ile   Asp
      210                       215                       220

Val   Arg   Asp   Ala   Pro   Leu   Lys   Glu   Ile   Lys   Val   Thr   Ser   Ser   Arg   Arg
225                       230                       235                             240

Phe   Ile   Ala   Ser   Phe   Asn   Val   Val   Asn   Thr   Thr   Lys   Arg   Asp   Ala   Gly
                        245                       250                       255

Lys   Tyr   Arg   Cys   Met   Ile   Arg   Thr   Glu   Gly   Gly   Val   Gly   Ile   Ser   Asn
                  260                       265                       270

Tyr   Ala   Glu   Leu   Val   Val   Lys   Glu   Pro   Pro   Val   Pro   Ile   Ala   Pro   Pro
            275                       280                       285

Gln   Leu   Ala   Ser   Val   Gly   Ala   Thr   Tyr   Leu   Trp   Ile   Gln   Leu   Asn   Ala
      290                       295                       300

Asn   Ser   Ile   Asn   Gly   Asp   Gly   Pro   Ile   Val   Ala   Arg   Glu   Val   Glu   Tyr
305                       310                       315                             320

Cys   Thr   Ala   Ser   Gly   Ser   Trp   Asn   Asp   Arg   Gln   Pro   Val   Asp   Ser   Thr
                        325                       330                       335

```
Ser  Tyr  Lys  Ile  Gly  His  Leu  Asp  Pro  Asp  Thr  Glu  Tyr  Glu  Ile  Ser
               340                 345                      350

Val  Leu  Leu  Thr  Arg  Pro  Gly  Glu  Gly  Thr  Gly  Ser  Pro  Gly  Pro
355            355                 360                 365

Ala  Leu  Arg  Thr  Arg  Thr  Lys  Cys  Ala  Asp  Pro  Met  Arg  Gly  Pro  Arg
     370                      375                 380

Lys  Leu  Glu  Val  Val  Glu  Val  Lys  Ser  Arg  Gln  Ile  Thr  Ile  Arg  Trp
385                 390                      395                           400

Glu  Pro  Phe  Gly  Tyr  Asn  Val  Thr  Arg  Cys  His  Ser  Tyr  Asn  Leu  Thr
               405                      410                           415

Val  His  Tyr  Cys  Tyr  Gln  Val  Gly  Gly  Gln  Glu  Gln  Val  Arg  Glu  Glu
               420                 425                      430

Val  Ser  Trp  Asp  Thr  Glu  Asn  Ser  His  Pro  Gln  His  Thr  Ile  Thr  Asn
               435                 440                      445

Leu  Ser  Pro  Tyr  Thr  Asn  Val  Ser  Val  Lys  Leu  Ile  Leu  Met  Asn  Pro
     450                      455                 460

Glu  Gly  Arg  Lys  Glu  Ser  Gln  Glu  Leu  Ile  Val  Gln  Thr  Asp  Glu  Asp
465                 470                      475                           480

Leu  Pro  Gly  Ala  Val  Pro  Thr  Glu  Ser  Ile  Gln  Gly  Ser  Thr  Phe  Glu
               485                 490                      495

Glu  Lys  Ile  Phe  Leu  Gln  Trp  Arg  Glu  Pro  Thr  Gln  Thr  Tyr  Gly  Val
               500                 505                      510

Ile  Thr  Leu  Tyr  Glu  Ile  Thr  Tyr  Lys  Ala  Val  Ser  Ser  Phe  Asp  Pro
          515                      520                 525

Glu  Ile  Asp  Leu  Ser  Asn  Gln  Ser  Gly  Arg  Val  Ser  Lys  Leu  Gly  Asn
     530                      535                 540

Glu  Thr  His  Phe  Leu  Phe  Phe  Gly  Leu  Tyr  Pro  Gly  Thr  Thr  Tyr  Ser
545                      550                 555                           560

Phe  Thr  Ile  Arg  Ala  Ser  Thr  Ala  Lys  Gly  Phe  Gly  Pro  Pro  Ala  Thr
               565                 570                      575

Asn  Gln  Phe  Thr  Thr  Lys  Ile  Ser  Ala  Pro  Ser  Met  Pro  Ala  Tyr  Glu
               580                 585                      590

Leu  Glu  Thr  Pro  Leu  Asn  Gln  Thr  Asp  Asn  Thr  Val  Thr  Val  Met  Leu
          595                 600                      605

Lys  Pro  Ala  His  Ser  Arg  Gly  Ala  Pro  Val  Ser  Val  Tyr  Gln  Ile  Val
610                           615                      620

Val  Glu  Glu  Glu  Arg  Pro  Arg  Arg  Thr  Lys  Lys  Thr  Thr  Glu  Ile  Leu
625                      630                 635                           640

Lys  Cys  Tyr  Pro  Val  Pro  Ile  His  Phe  Gln  Asn  Ala  Ser  Leu  Leu  Asn
               645                      650                           655

Ser  Gln  Tyr  Tyr  Phe  Ala  Ala  Glu  Phe  Pro  Ala  Asp  Ser  Leu  Gln  Ala
               660                 665                      670

Ala  Gln  Pro  Phe  Thr  Ile  Gly  Asp  Asn  Lys  Thr  Tyr  Asn  Gly  Tyr  Trp
          675                      680                 685

Asn  Thr  Pro  Leu  Leu  Pro  Tyr  Lys  Ser  Tyr  Arg  Ile  Tyr  Phe  Gln  Ala
     690                      695                 700

Ala  Ser  Arg  Ala  Asn  Gly  Glu  Thr  Lys  Ile  Asp  Cys  Val  Gln  Val  Ala
705                      710                      715                      720

Thr  Lys  Gly  Ala  Ala  Thr  Pro  Lys  Pro  Val  Pro  Glu  Pro  Glu  Lys  Gln
               725                 730                      735

Thr  Asp  His  Thr  Val  Lys  Ile  Ala  Gly  Val  Ile  Ala  Gly  Ile  Leu  Leu
               740                 745                      750

Phe  Val  Ile  Ile  Phe  Leu  Gly  Val  Val  Leu  Val  Met  Lys  Lys  Arg  Lys
```

-continued

```
                        755                           760                            765
    Leu  Ala  Lys  Lys  Arg  Lys  Glu  Thr  Met  Ser  Ser  Thr  Arg  Gln  Glu  Met
              770                      775                      780
    Thr  Val  Met  Val  Asn  Ser  Met  Asp  Lys  Ser  Tyr  Ala  Glu  Gln  Gly  Thr
    785                 790                      795                                800
    Asn  Cys  Asp  Glu  Ala  Phe  Ser  Phe  Met  Asp  Thr  His  Asn  Leu  Asn  Gly
                        805                      810                      815
    Arg  Ser  Val  Ser  Ser  Pro  Ser  Ser  Phe  Thr  Met  Lys  Thr  Asn  Thr  Leu
                   820                      825                      830
    Ser  Thr  Ser  Val  Pro  Asn  Ser  Tyr  Tyr  Pro  Asp  Glu  Thr  His  Thr  Met
              835                      840                      845
    Ala  Ser  Asp  Thr  Ser  Ser  Leu  Val  Gln  Ser  His  Thr  Tyr  Lys  Lys  Arg
    850                      855                      860
    Glu  Pro  Ala  Asp  Val  Pro  Tyr  Gln  Thr  Gly  Gln  Leu  His  Pro  Ala  Ile
    865                      870                      875                           880
    Arg  Val  Ala  Asp  Leu  Leu  Gln  His  Ile  Thr  Gln  Met  Lys  Cys  Ala  Glu
                        885                      890                      895
    Gly  Tyr  Gly  Phe  Lys  Glu  Glu  Tyr  Glu  Ser  Phe  Phe  Glu  Gly  Gln  Ser
                   900                      905                      910
    Ala  Pro  Trp  Asp  Ser  Ala  Lys  Lys  Asp  Glu  Asn  Arg  Met  Lys  Asn  Arg
              915                      920                      925
    Tyr  Gly  Asn  Ile  Ile  Ala  Tyr  Asp  His  Ser  Arg  Val  Arg  Leu  Gln  Thr
    930                      935                      940
    Ile  Glu  Gly  Asp  Thr  Asn  Ser  Asp  Tyr  Ile  Asn  Gly  Asn  Tyr  Ile  Asp
    945                      950                      955                           960
    Gly  Tyr  His  Arg  Pro  Asn  His  Tyr  Ile  Ala  Thr  Gln  Gly  Pro  Met  Gln
                        965                      970                      975
    Glu  Thr  Ile  Tyr  Asp  Phe  Trp  Arg  Met  Val  Trp  His  Glu  Asn  Thr  Ala
                   980                      985                      990
    Ser  Ile  Ile  Met  Val  Thr  Asn  Leu  Val  Glu  Val  Gly  Arg  Val  Lys  Cys
              995                      1000                     1005
    Cys  Lys  Tyr  Trp  Pro  Asp  Asp  Thr  Glu  Ile  Tyr  Lys  Asp  Ile  Lys  Val
              1010                     1015                     1020
    Thr  Leu  Ile  Glu  Thr  Glu  Leu  Leu  Ala  Glu  Tyr  Val  Ile  Arg  Thr  Phe
    1025                     1030                     1035                          1040
    Ala  Val  Glu  Lys  Arg  Gly  Val  His  Glu  Ile  Arg  Glu  Ile  Arg  Gln  Phe
                        1045                     1050                     1055
    His  Phe  Thr  Gly  Trp  Pro  Asp  His  Gly  Val  Pro  Tyr  His  Ala  Thr  Gly
                   1060                     1065                     1070
    Leu  Leu  Gly  Phe  Val  Arg  Gln  Val  Lys  Ser  Lys  Ser  Pro  Pro  Ser  Ala
              1075                     1080                     1085
    Gly  Pro  Leu  Val  Val  His  Cys  Ser  Ala  Gly  Ala  Gly  Arg  Thr  Gly  Cys
    1090                     1095                     1100
    Phe  Ile  Val  Ile  Asp  Ile  Met  Leu  Asp  Met  Ala  Glu  Arg  Glu  Gly  Val
    1105                     1110                     1115                          1120
    Val  Asp  Ile  Tyr  Asn  Cys  Val  Arg  Glu  Leu  Arg  Ser  Arg  Arg  Val  Asn
                        1125                     1130                     1135
    Met  Val  Gln  Thr  Glu  Glu  Gln  Tyr  Val  Phe  Ile  His  Asp  Ala  Ile  Leu
                   1140                     1145                     1150
    Glu  Ala  Cys  Leu  Cys  Gly  Asp  Thr  Ser  Val  Pro  Ala  Ser  Gln  Val  Arg
              1155                     1160                     1165
    Ser  Leu  Tyr  Tyr  Asp  Met  Asn  Lys  Leu  Asp  Pro  Gln  Thr  Asn  Ser  Ser
              1170                     1175                     1180
```

```
Gln  Ile  Lys  Glu  Glu  Phe  Arg  Thr  Leu  Asn  Met  Val  Thr  Pro  Thr  Leu
1185                1190                1195                          1200

Arg  Val  Glu  Asp  Cys  Ser  Ile  Ala  Leu  Leu  Pro  Arg  Asn  His  Glu  Lys
                    1205                1210                          1215

Asn  Arg  Cys  Met  Asp  Ile  Leu  Pro  Pro  Asp  Arg  Cys  Leu  Pro  Phe  Leu
                    1220                1225                1230

Ile  Thr  Ile  Asp  Gly  Glu  Ser  Ser  Asn  Tyr  Ile  Asn  Ala  Ala  Leu  Met
               1235                1240                     1245

Asp  Ser  Tyr  Lys  Gln  Pro  Ser  Ala  Phe  Ile  Val  Thr  Gln  His  Pro  Leu
               1250                1255                     1260

Pro  Asn  Thr  Val  Lys  Asp  Phe  Trp  Arg  Leu  Val  Leu  Asp  Tyr  His  Cys
1265                1270                1275                          1280

Thr  Ser  Val  Val  Met  Leu  Asn  Asp  Val  Asp  Pro  Ala  Gln  Leu  Cys  Pro
                    1285                1290                          1295

Gln  Tyr  Trp  Pro  Glu  Asn  Gly  Val  His  Arg  His  Gly  Pro  Ile  Gln  Val
                    1300                1305                     1310

Glu  Phe  Val  Ser  Ala  Asp  Leu  Glu  Glu  Asp  Ile  Ile  Ser  Arg  Ile  Phe
               1315                1320                     1325

Arg  Ile  Tyr  Asn  Ala  Ala  Arg  Pro  Gln  Asp  Gly  Tyr  Arg  Met  Val  Gln
          1330                     1335                1340

Gln  Phe  Gln  Phe  Leu  Gly  Trp  Pro  Met  Tyr  Arg  Asp  Thr  Pro  Val  Ser
1345                1350                1355                          1360

Lys  Arg  Ser  Phe  Leu  Lys  Leu  Ile  Arg  Gln  Val  Asp  Lys  Trp  Gln  Glu
                    1365                1370                          1375

Glu  Tyr  Asn  Gly  Gly  Glu  Gly  Pro  Thr  Val  Val  His  Cys  Leu  Asn  Gly
               1380                1385                     1390

Gly  Gly  Arg  Ser  Gly  Thr  Phe  Cys  Ala  Ile  Ser  Ile  Val  Cys  Glu  Met
          1395                     1400                1405

Leu  Arg  His  Gln  Arg  Thr  Val  Asp  Val  Phe  His  Ala  Val  Lys  Thr  Leu
     1410                1415                1420

Arg  Asn  Asn  Lys  Pro  Asn  Met  Val  Asp  Leu  Leu  Asp  Gln  Tyr  Lys  Phe
1425                1430                1435                          1440

Cys  Tyr  Glu  Val  Ala  Leu  Glu  Tyr  Leu  Asn  Ser  Gly
                    1445                1450
```

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:9:

GAGCCGCGGC TCGAGTTAAC CGCCATGGAT GTGGCGGCCG     40

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:10:

GCTCACAGCT AGTTCAGCCC     20

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:11:

```
CTACACCCAC  ATCTAACGAA  CCGTGAAGCA  GGG                                33
```